US012715870B2

(12) United States Patent
Kong et al.

(10) Patent No.: US 12,715,870 B2
(45) Date of Patent: Aug. 25, 2026

(54) HETEROCYCLIC COMPOUND AS BCL-2 INHIBITOR

(71) Applicant: Beijing Innocare Pharma Tech Co., Ltd., Beijing (CN)

(72) Inventors: Norman Xianglong Kong, Nanjing (CN); Chao Zhou, Nanjing (CN); Zhixiang Zheng, Nanjing (CN)

(73) Assignee: Beijing Innocare Pharma Tech Co., Ltd., Beijing (CN)

(*) Notice: Subject to any disclaimer, the term of this patent is extended or adjusted under 35 U.S.C. 154(b) by 567 days.

(21) Appl. No.: 18/019,701

(22) PCT Filed: Aug. 2, 2021

(86) PCT No.: PCT/CN2021/109991

§ 371 (c)(1),
(2) Date: Feb. 3, 2023

(87) PCT Pub. No.: WO2022/028353

PCT Pub. Date: Feb. 10, 2022

(65) Prior Publication Data

US 2023/0271959 A1 Aug. 31, 2023

(30) Foreign Application Priority Data

Aug. 6, 2020 (CN) ......................... 202010782972.6

(51) Int. Cl.
*A61P 35/02* (2006.01)
*C07D 471/04* (2006.01)

(52) U.S. Cl.
CPC ............ *C07D 471/04* (2013.01); *A61P 35/02* (2018.01)

(58) Field of Classification Search
CPC ........ C07D 471/04; A61P 35/02; A61P 35/00; A61K 31/437; A61K 31/496
See application file for complete search history.

(56) References Cited

U.S. PATENT DOCUMENTS

2011/0124628 A1 5/2011 Bruncko et al.

FOREIGN PATENT DOCUMENTS

| | | | | |
|---|---|---|---|---|
| CN | 106749233 A | 5/2017 | | |
| WO | WO-2010/065865 A2 | 6/2010 | | |
| WO | WO-2010/138588 A2 | 12/2010 | | |
| WO | WO-2011149492 A1 * | 12/2011 | | A61P 37/00 |
| WO | WO-2012/058392 A1 | 5/2012 | | |
| WO | WO-2014/158528 A1 | 10/2014 | | |
| WO | WO-2017/212431 A1 | 12/2017 | | |
| WO | WO-2018/009444 A1 | 1/2018 | | |
| WO | WO-2018/027097 A1 | 2/2018 | | |
| WO | WO-2020/103921 A1 | 5/2020 | | |
| WO | WO-2021/116929 A1 | 6/2021 | | |

OTHER PUBLICATIONS

Birkenshaw et al. (Nature Communications 2019:2385: pp. 1-10). (Year: 2019).*

Cang et al., ABT—199 (venetoclax) and BCL-2 inhibitors in clinical development, Journal of Hematology & Oncology, 2015, vol. 8, Article No. 129, pp. 1-8 DOI:10.1186/s13045-015-0224-3.

Liu et al., "Development of high potent and selective Bcl-2 inhibitors bearing the structural elements of natural product artemisinin." European Journal of Medicinal Chemistry 159 (2018):149-165.

Extended European Search Report for EP Application No. 21852552.5 dated Aug. 2, 2024.

Chen et al., "Total synthesis and structure revision of chrysamide B", Organic Chemistry Frontiers 5(23): 3402-3405 (2018).

Ku et al. "Development of a convergent large-scale synthesis for Venetoclax, a first-in-class BCL-2 selective inhibitor." The Journal of Organic Chemistry 84(8) (2019): 4814-4829.

Lorentz-Petersen et al., "Iridium-catalyzed condensation of amines and vicinal diols to substituted piperazines", European Journal of Organic Chemistry 2012(34): 6752-6759 (2012).

Souers et al., "ABT-199, a Potent and Selective BCL-2 Inhibitor, Achieves Antitumor Activity While Sparing Platelets," Nature Medicine, 19(2): 202-208 (2013).

Valentin et al., "The rise of apoptosis: targeting apoptosis in hematologic malignancies", Blood, The Journal of the American Society of Hematology 132(12): 1248-1264 (2018).

(Continued)

*Primary Examiner* — Ernst V Arnold
(74) *Attorney, Agent, or Firm* — Foley Hoag LLP; Dana M. Gordon; Shejla S. Pollozi

(57) ABSTRACT

The present invention relates to a compound, a pharmaceutical composition containing thereof, preparation methods therefor, and use thereof as BCL-2 inhibitors. The compound is a compound represented by formula (I), or an isomer, prodrug, solvate, stable isotopic derivative or pharmaceutically acceptable salt thereof. The invention also relates to use of the compound for treating or preventing diseases mediated by BCL-2, such as tumors, and to a method for using the same for treating described diseases.

(I)

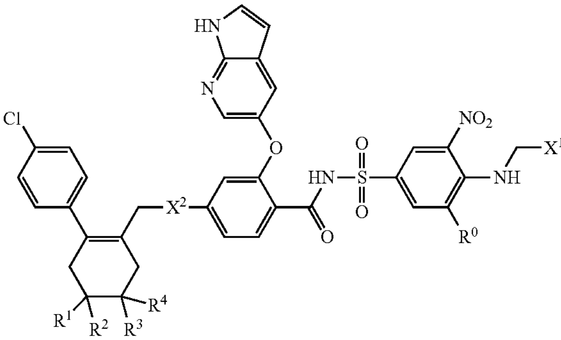

6 Claims, No Drawings

(56) References Cited

OTHER PUBLICATIONS

Zeitlin et al., "Expanding circle of inhibition: small-molecule inhibitors of Bcl-2 as anticancer cell and antiangiogenic agents", Journal of Clinical Oncology 26(25): 4180-4188 (2008).
Li et al., "A Review of Developments of the Selective BCL-2 Inhibitor Venetoclax," Journal of Inner Mongolia Medical University 39.3 (2017): 283-287.
Drug Label for VENCLEXTA®, revised Jun. 2022, 57 pages.
Center for Drug Evaluation and Research, Application No. 208573Orig1s000 for VENCLEXTA® (generic Venetoclax), Oct. 29, 2015, 75 pages.

* cited by examiner

HETEROCYCLIC COMPOUND AS BCL-2 INHIBITOR

RELATED APPLICATIONS

This application is the U.S. national phase of International Patent Application No. PCT/CN21/109991, filed Aug. 2, 2021; which claims the benefit of priority to China Patent Application No. 202010782972.6, filed Aug. 6, 2020.

TECHNICAL FIELD

The present invention relates to compounds, pharmaceutical compositions containing them, and their use as B-cell lymphoma-2 (BCL-2) inhibitors. More specifically, the present invention provides novel compounds as BCL-2 inhibitors, pharmaceutical compositions containing described compounds and the use of described compounds in the treatment or prevention of BCL-2-mediated diseases and dysfunctions. Such diseases are tumors, for example. The present invention also relates to methods for preparing described compounds.

BACKGROUND ART

The BCL-2 protein family is one of the core regulatory mechanisms of apoptosis (also called as programmed cell death), which can receive and transmit internal intracellular signals or external environmental stress signals, such as nutritional or hypoxic stress, DNA damage, excessive activation of carcinogenesis genes, endoplasmic reticulum stress, etc., mainly plays a leading role in the intrinsic apoptosis pathway (Intrinsic pathway). BCL-2 (B-cell lymphoma-2) protein was first discovered in 1986 and is expressed by the BCL-2 gene. The BCL-2 gene is a proto-oncogene, and the proteins it expresses are called BCL-2 family proteins. There are totally 27 BCL-2 family proteins in the human body, which can be divided into 3 subclasses according to function and sequence analysis. The first subclass is anti-apoptotic, including BCL-XL, BCL-2, BCL-W, MCL-1, BFL-1, which are mainly localized on mitochondria and protect mitochondria from adversity damage. The other two subclasses are apoptosis-promoting, and one subclass is the ultimate executor of mitochondrial damage, including BAX and BAK. The rest belong to the BH3 subclass, which can directly sense various cellular stress signals. A dynamic balance of interactions between proteins that antagonize and promote apoptosis determines the life and death fate of cells. BCL-2 protein, which antagonizes apoptosis, is closely related to tumors. About 50% of tumors (such as leukemia, rectal cancer, prostate cancer, etc.) have abnormal overexpression of BCL-2 family proteins, wherein the abnormal activity of BCL-2 is widely present in hematological tumours. Multiple signaling pathways such as JAK-STAT, NFkB, and UPP (ubiquitin-proteasome) can cause the overexpression of BCL-2 protein that antagonizes apoptosis.

The high expression of BCL-2 family anti-apoptotic proteins is related to the drug resistance of various tumors. For example, the overexpression of BCL-2 anti-apoptotic proteins can enable tumor cells to escape apoptosis caused by anti-tumor drugs, thereby causing drug resistance. Studies have shown that inhibition of BCL-2 family proteins can inhibit tumor angiogenesis, thereby inhibiting tumor metastasis (Benjamin, D.; Isaac, J. et al. J. Clin. Oncol. 2008, 26(25), 4180). Therefore, the targeted inhibition of BCL-2 family anti-apoptotic proteins can inhibit the occurrence, development and drug resistance of tumors.

Although more than 20 small-molecule inhibitors targeting the BCL-2 family have been reported, very few of them have been entered clinical trials. There is only one partial response out of 26 chronic lymphocytic leukemia (CLL) patients receiving Teva's Obatoclax's treatment. At the same time, it has strong neurotoxicity. The development of Obatoclax was terminated in 2013. AbbVie's Navitoclax (ABT-263), shows 50% of excellent response in Phase I dose escalation in patients with relapsed or refractory lymphoid malignancies, but also shows very strong targeted toxicity related to BCL-XL: such as thrombocytopenia and severe anemia. Venetoclax (ABT-199), developed by AbbVie and Roche together, is a highly selective BCL-2 inhibitor (Andrew, J.; Joel, D. et al. Nature Medicine, 2013, 19(2), 202). The objective response rate (ORR) and the complete remission rate (CR) were improved greatly in the treatment of relapsed/refractory chronic lymphocytic leukemia (CLL), mantle cell lymphoma (MCL), multiple myeloma (MM), etc. by combination therapy with Ibrutinib (Valentin, R.; Grablow, S. et al. Blood, 2018, 132(12), 1248). Nevertheless, there are toxic side effects such as leukopenia and thrombocytopenia, anemia, diarrhea, dizziness, fatigue, susceptibility to infection, and serious toxic side effects such as pneumonia, anemia, high fever, etc. Therefore, it is necessary to develop BCL-2 selective inhibitors with high activity and less toxic side effects.

SUMMARY OF THE INVENTION

The present invention provides a compound of formula (I), and the isomers, prodrugs, solvates, stable isotopic derivatives or pharmaceutically acceptable salts thereof:

(I)

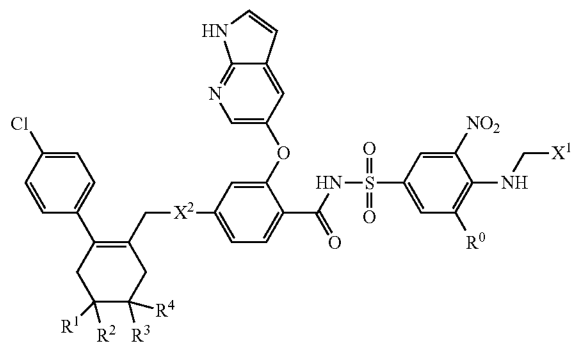

wherein:

$X^1$ is selected from an optionally substituted 6-membered saturated heterocyclic group containing one or two heteroatoms selected from N, O, S, wherein the optional substituent is selected from a 4-membered saturated heterocyclic group containing one or two heteroatoms selected from N, O and S; preferably, $X^1$ is selected from an optionally substituted 6-membered saturated heterocyclic group containing one or two heteroatoms selected from N, O, wherein the optional substituent is selected from oxetanyl; further preferably, $X^1$ is selected from 1,4-dioxanyl, tetrahydropyranyl, N-oxetanyl piperidinyl, N-oxetanylmorpholinyl; most preferably, $X^1$ is selected from (S)-1,4-dioxan-2-yl, (R)-1,4-dioxan-2-yl, tetrahydropyran-4-yl, 1-(oxetan-3-yl)piperidin-4-yl, (S)-4-(oxetan-3-yl)morpholin-2-yl;

$X^2$ is selected from a 5-6 membered heterocyclylene group containing one or two N atoms, wherein the ring of the heterocyclylene group can be optionally substituted by one or two C1-C4 alkyl groups; preferably, $X^2$ is selected from a 6-membered heterocyclylene group containing one or two N atoms, wherein the ring of the heterocyclylene group can be optionally substituted by one or two C1-C4 alkyl groups; further preferably, $X^2$ is selected from

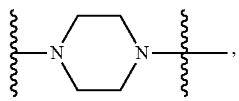

wherein, the ring can be optionally substituted by one C1-C4 alkyl; most preferably, $X^2$ is selected from

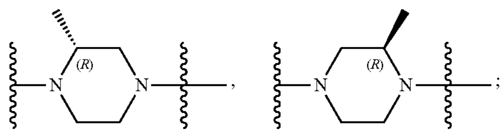

$R^0$ is selected from hydrogen, halogen; Preferably, $R^0$ is selected from hydrogen, fluorine, chlorine; Most preferably, $R^0$ is selected from hydrogen, fluorine;

$R^1$, $R^2$, $R^3$, $R^4$ are each independently selected from hydrogen, C1-C6 alkyl, wherein $R^1$ and $R^2$ or $R^3$ and $R^4$ can form a 3-6 membered cycloalkyl together with the carbon atom to which they are attached; preferably, $R^1$, $R^2$, $R^3$, $R^4$ are each independently selected from hydrogen, C1-C4 alkyl, wherein $R^1$ and $R^2$ or $R^3$ and $R^4$ can form a 3-4 membered cycloalkyl together with the carbon atom to which they are attached; more preferably, $R^1$, $R^2$, $R^3$, $R^4$ are each independently selected from hydrogen or methyl and $R^1$, $R^2$, $R^3$, $R^4$ are not all hydrogen, wherein $R^1$ and $R^2$ or $R^3$ and $R^4$ can be combined with the carbon atom to which they are attached to form a cyclopropyl group; most preferably, $R^1$, $R^2$, $R^3$, $R^4$ are each independently selected from hydrogen or methyl and $R^1$, $R^2$, $R^3$, $R^4$ are not all hydrogen, wherein $R^3$ and $R^4$ together with the carbon atom to which they are attached may form a cyclopropyl group.

Preferably, the present application relates to a compound of formula (I) as recited above, and the isomers, prodrugs, solvates, stable isotopic derivatives or pharmaceutically acceptable salts thereof, wherein:

$X^1$ is selected from optionally substituted 6-membered saturated heterocyclic groups containing one or two heteroatoms selected from N, O, wherein the optional substituents are selected from oxetanyl groups;

$X^2$ is selected from a 6-membered heterocyclylene group containing one or two N atoms; wherein, the ring of the 6-membered heterocyclylene group can be optionally substituted by one or two C1-C4 alkyl groups;

$R^0$ is selected from hydrogen, halogen;

$R^1$, $R^2$, $R^3$, $R^4$ are each independently selected from hydrogen, C1-C4 alkyl, wherein $R^1$ and $R^2$ or $R^3$ and $R^4$ together with the carbon atoms to which they are attached can form a 3- to 4-membered cycloalkyl group.

More preferably, the present application relates to a compound of formula (I) as recited above, and the isomers, prodrugs, solvates, stable isotopic derivatives or pharmaceutically acceptable salts thereof, wherein:

$X^1$ is selected from optionally substituted 6-membered saturated heterocyclic groups containing one or two heteroatoms selected from N, O, wherein the optional substituents are selected from oxetanyl groups;

$X^2$ is

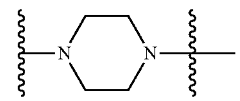

wherein the ring of $X^2$ can be optionally substituted by one C1-C4 alkyl group;

$R^0$ is selected from hydrogen, fluorine, chlorine;

$R^1$, $R^2$, $R^3$, $R^4$ are each independently selected from hydrogen, C1-C4 alkyl, wherein $R^1$ and $R^2$ or $R^3$ and $R^4$ together with the carbon atoms to which they are attached can form a 3- to 4-membered cycloalkyl group.

Further preferably, the present application relates to a compound of formula (I) as recited above, and the isomers, prodrugs, solvates, stable isotopic derivatives or pharmaceutically acceptable salts thereof, wherein:

$X^1$ is selected from 1,4-dioxanyl, tetrahydropyranyl, N-oxetanylpiperidinyl, N-oxetanylmorpholinyl;

$X^2$ is

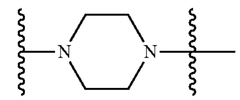

wherein the ring of $X^2$ can be optionally substituted by one C1-C4 alkyl group;

$R^0$ is selected from hydrogen, fluorine, chlorine;

$R^1$, $R^2$, $R^3$, $R^4$ are each independently selected from hydrogen or methyl and $R^1$, $R^2$, $R^3$, $R^4$ are not all hydrogen, wherein $R^1$ and $R^2$ or $R^3$ and $R^4$ together with the carbon atom to which they are attached may form a cyclopropyl group.

Further preferably, the present application relates to a compound of formula (I) as recited above, and the isomers, prodrugs, solvates, stable isotopic derivatives or pharmaceutically acceptable salts thereof, wherein:

$X^1$ is selected from 1,4-dioxanyl, tetrahydropyranyl, N-oxetanylpiperidinyl, N-oxetanylmorpholinyl;

$X^2$ is selected from

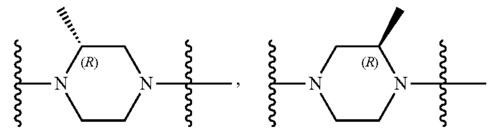

$R^0$ is selected from hydrogen, fluorine;

$R^1$, $R^2$, $R^3$, $R^4$ are each independently selected from hydrogen or methyl and $R^1$, $R^2$, $R^3$, $R^4$ are not all hydrogen, wherein $R^1$ and $R^2$ or $R^3$ and $R^4$ together with the carbon atom to which they are attached may form a cyclopropyl group.

Further preferably, the present application relates to a compound of formula (I) as recited above, and the isomers, prodrugs, solvates, stable isotopic derivatives or pharmaceutically acceptable salts thereof, wherein:

$X^1$ is selected from (S)-1,4-dioxan-2-yl, (R)-1,4-dioxan-2-yl, tetrahydropyran-4-yl, 1-(oxetan-3-yl)piperidin-4-yl, (S)-4-(oxetan-3-yl)morpholin-2-yl;

$X^2$ is selected from

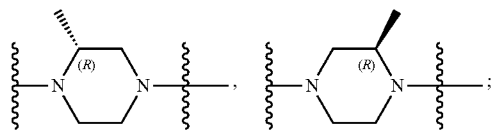

$R^0$ is selected from hydrogen, fluorine;

$R^1$, $R^2$, $R^3$, $R^4$ are each independently selected from hydrogen or methyl and $R^1$, $R^2$, $R^3$, $R^4$ are not all hydrogen, wherein $R^3$ and $R^4$ together with the carbon atom to which they are attached may form a cyclopropyl group.

Further preferably, the present application relates to a compound of formula (I) as recited above, and the isomers, prodrugs, solvates, stable isotopic derivatives or pharmaceutically acceptable salts thereof, which is selected from the group consisting of:

1

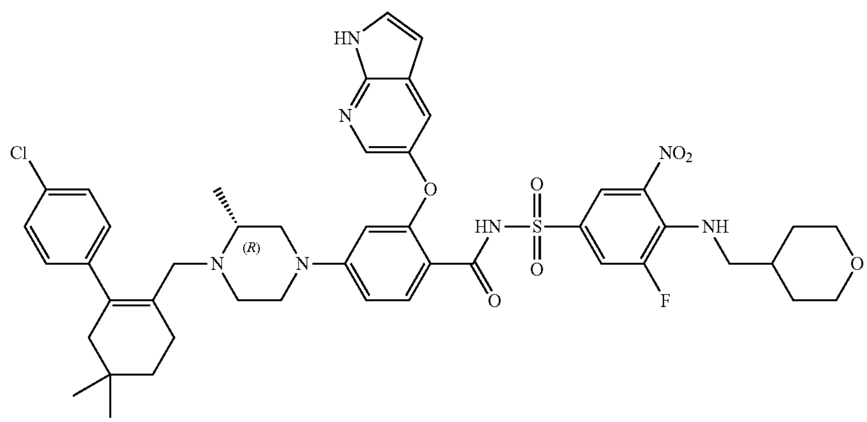

2

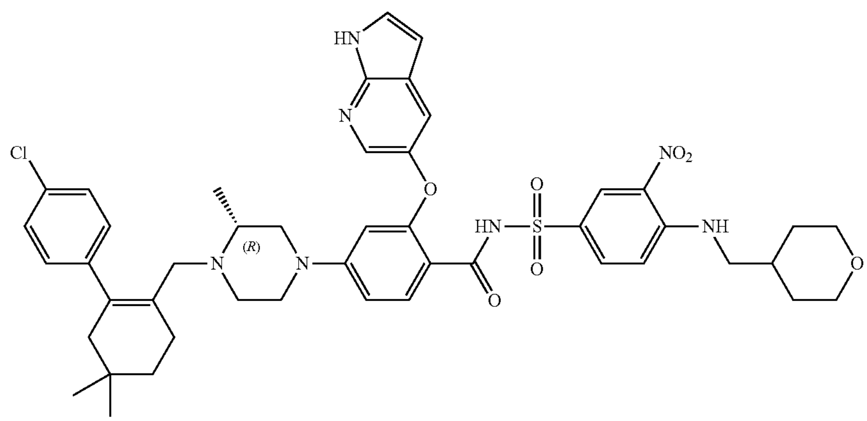

-continued
3
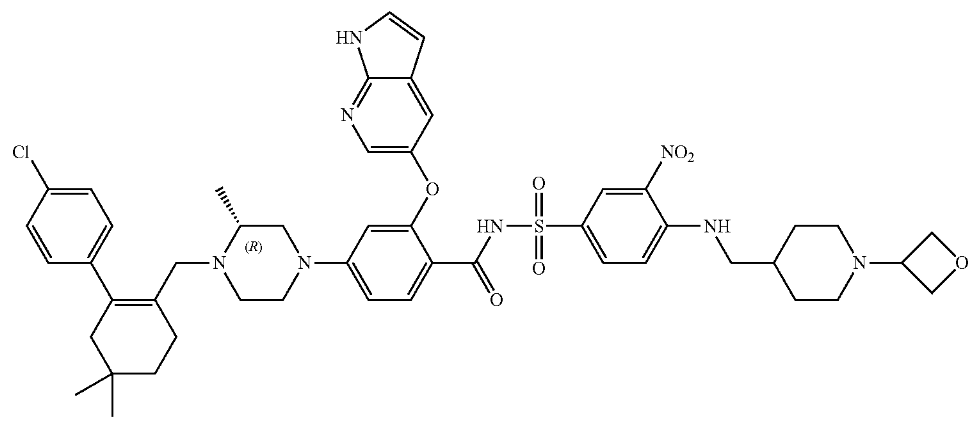
4
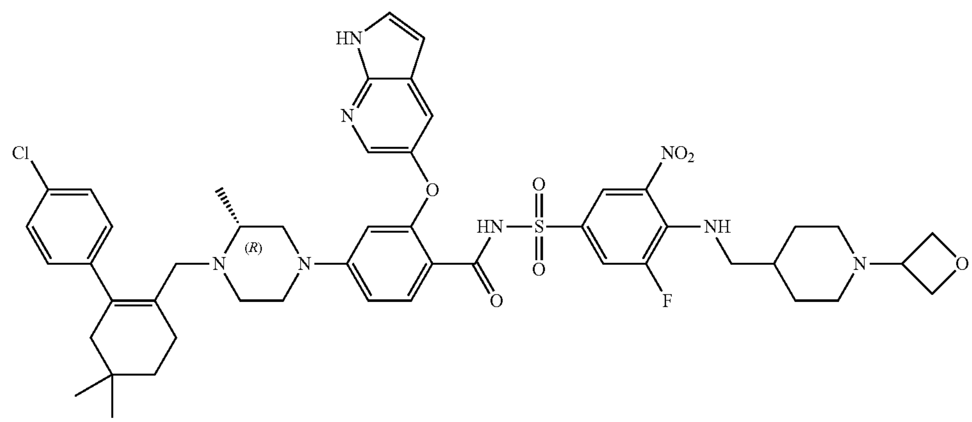
5
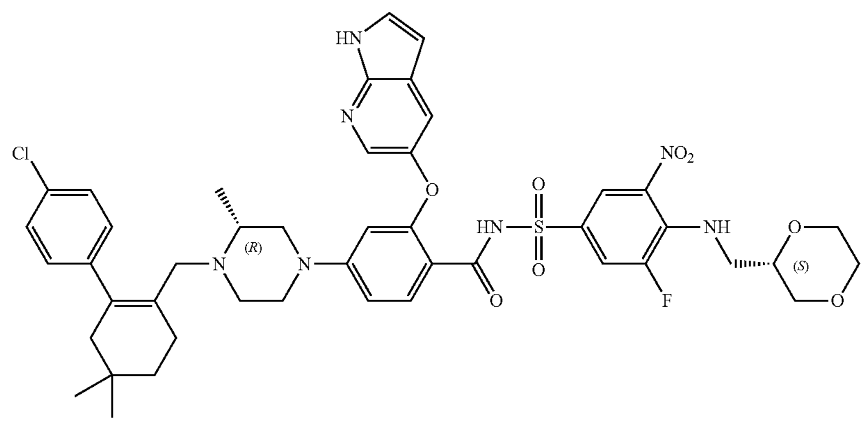

-continued
6
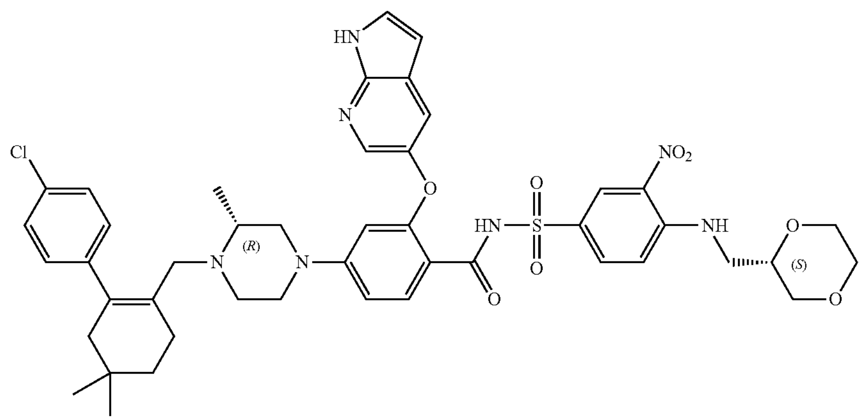
8
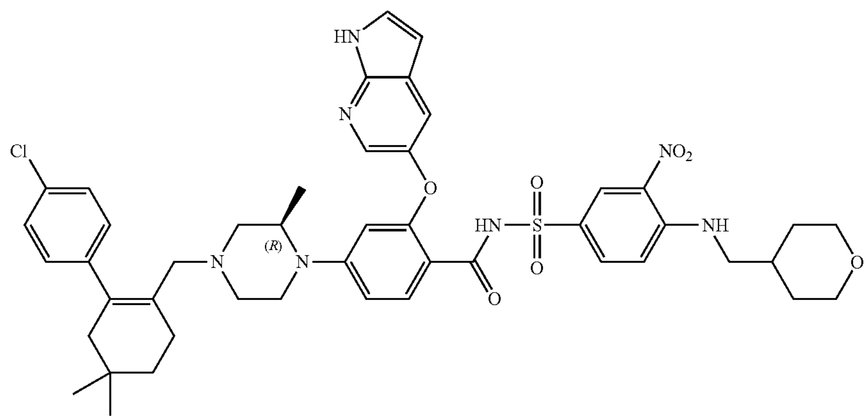
9
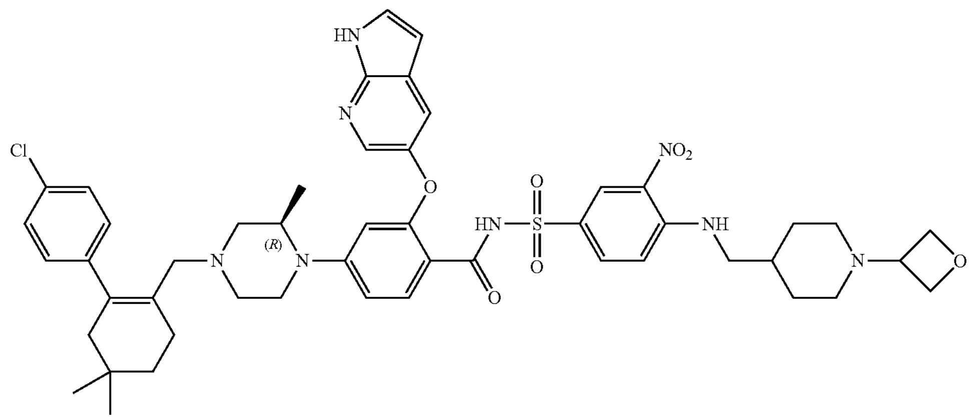

-continued
10
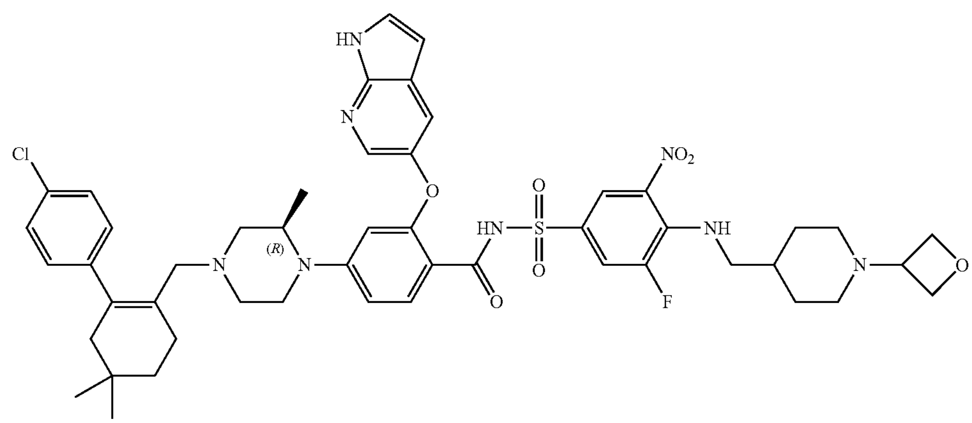
11
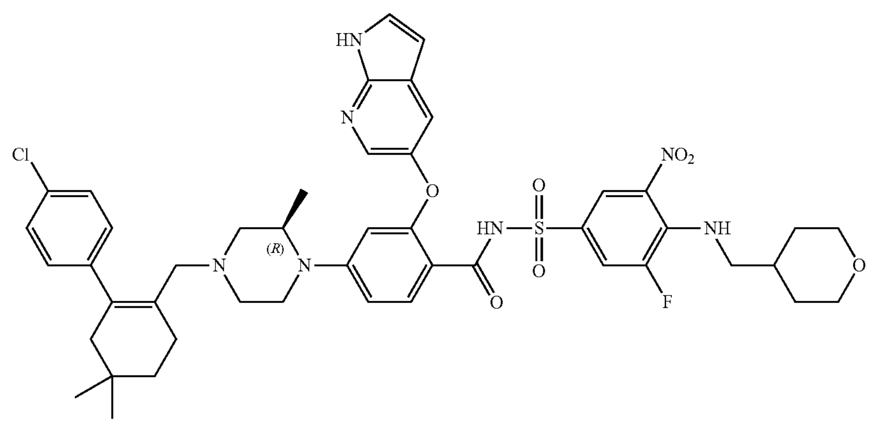
12
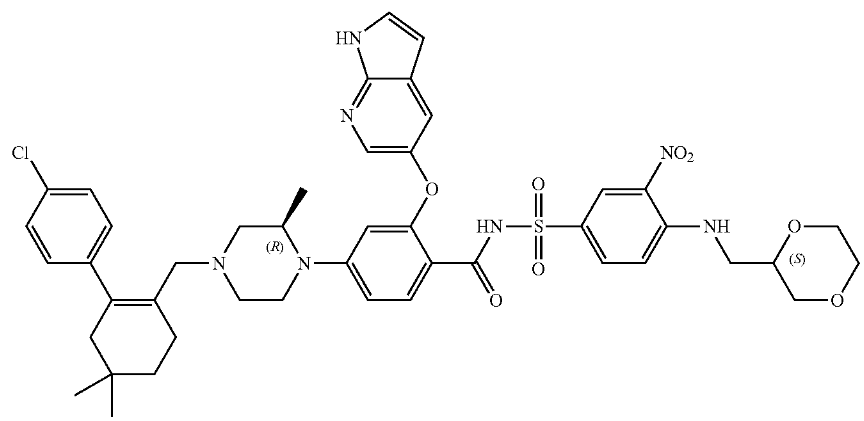

-continued
14
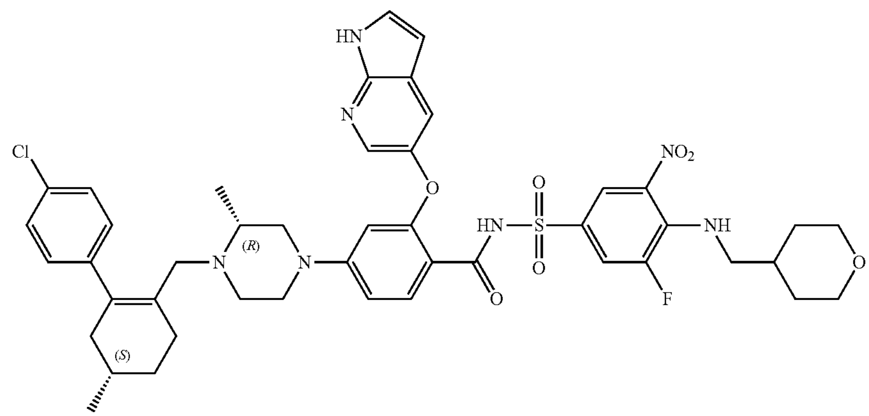
15
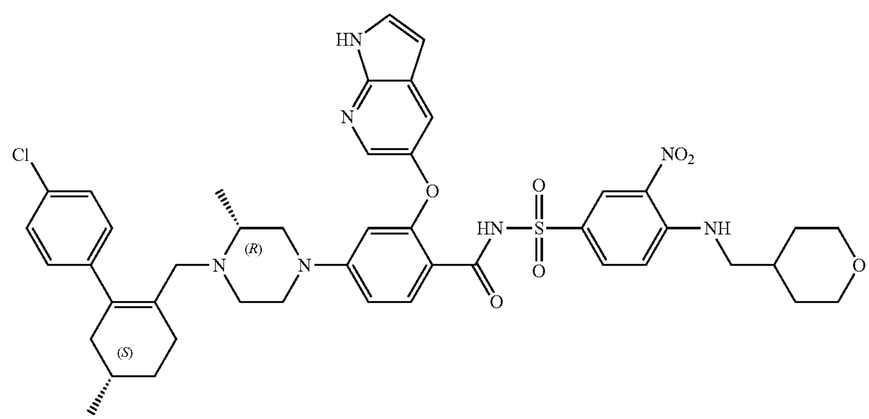
16
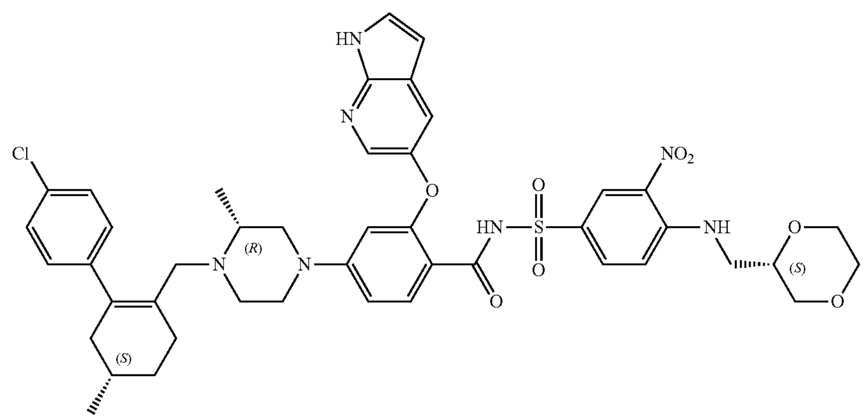
17
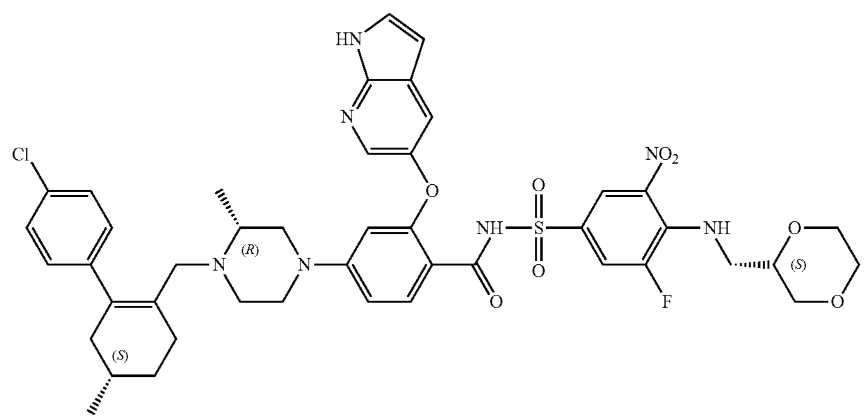

-continued
18
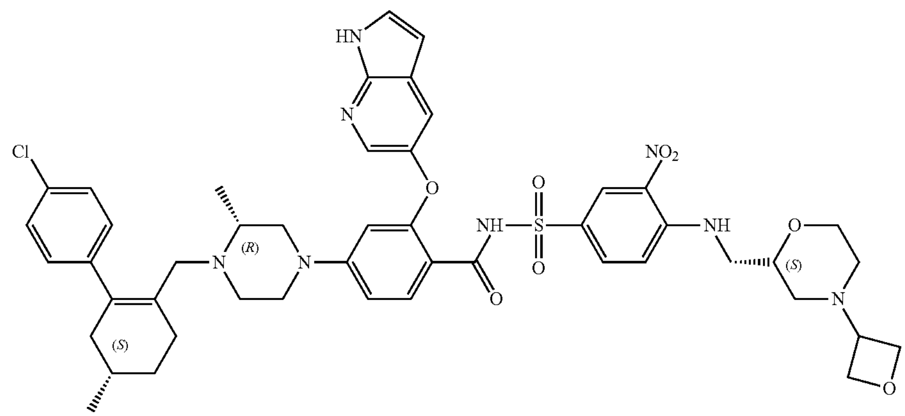
19
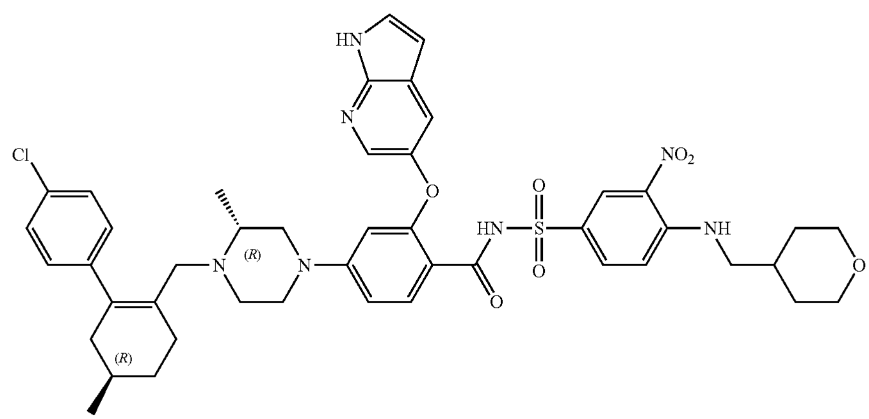
20
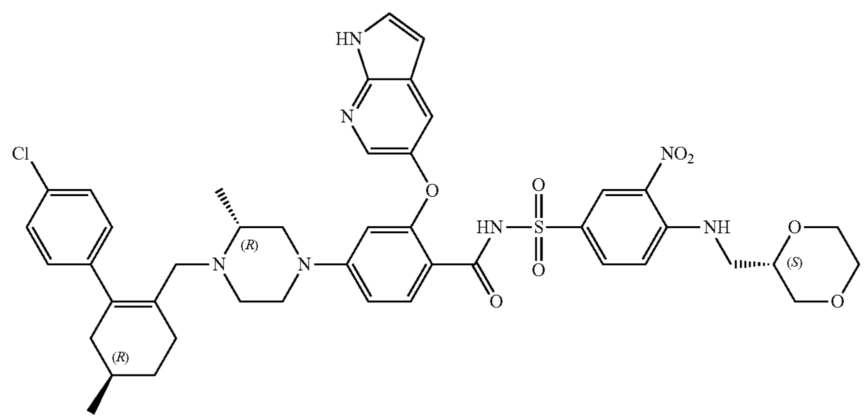
21
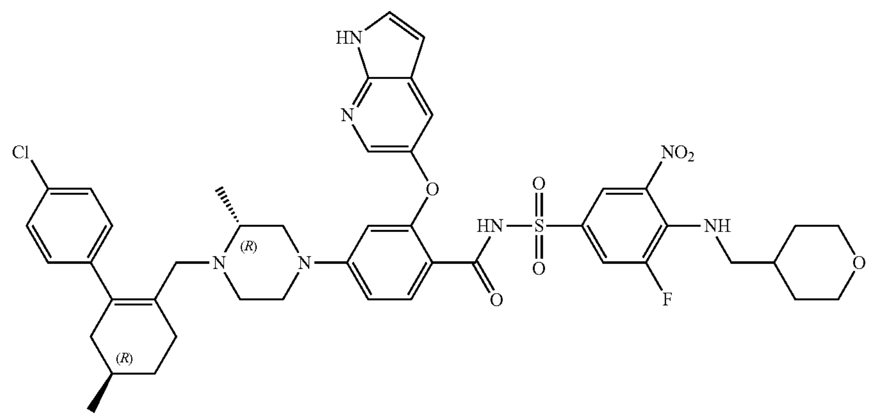

-continued
22
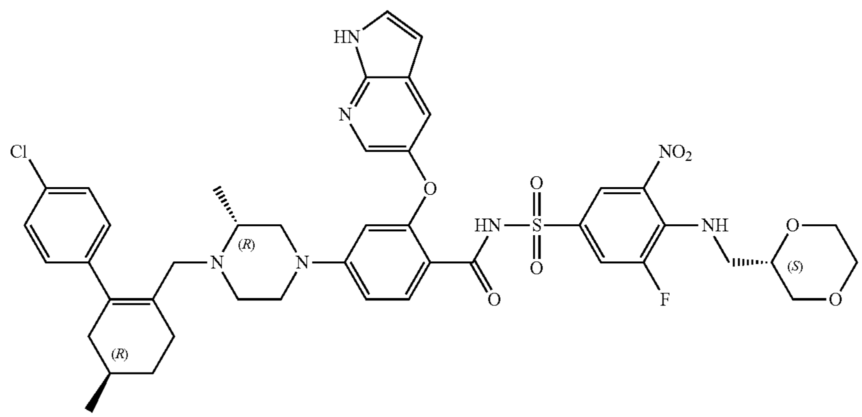
23
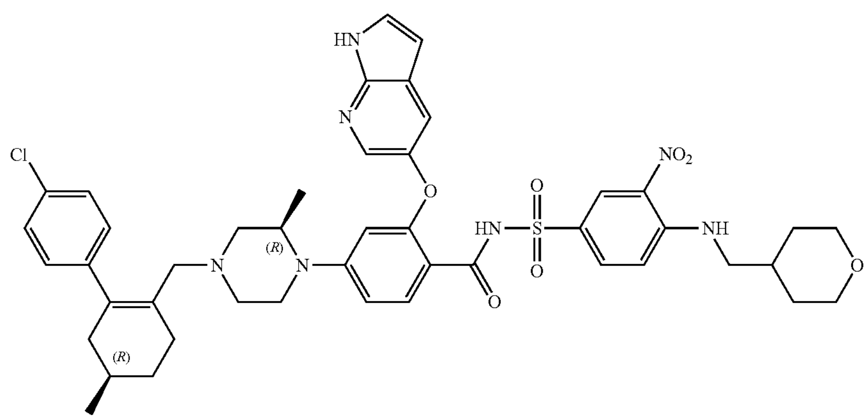
24
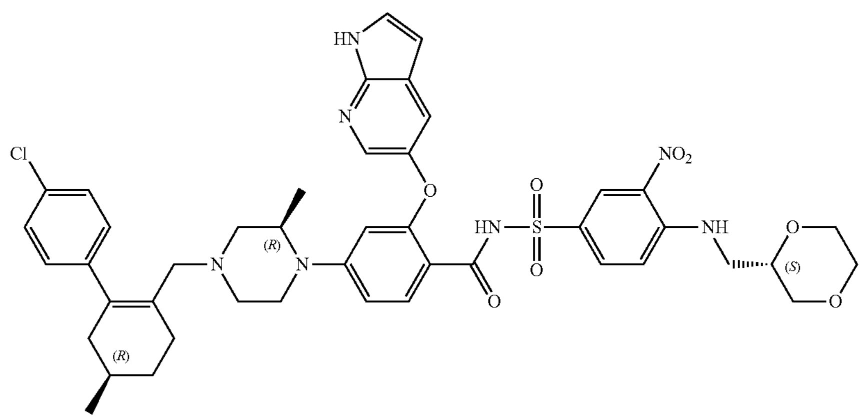
25
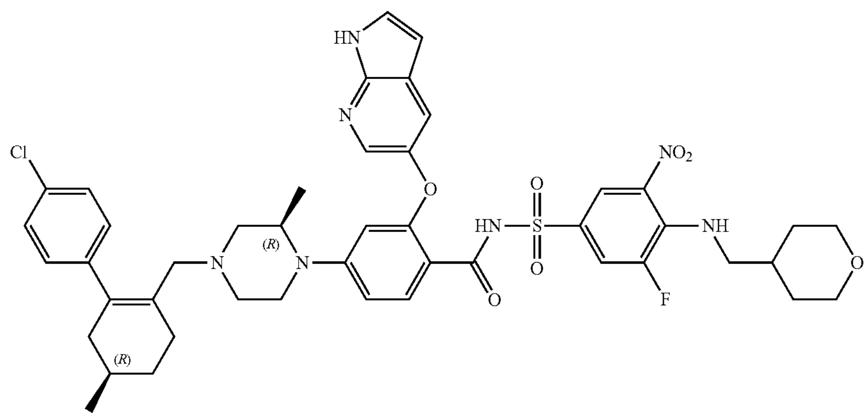

-continued
26
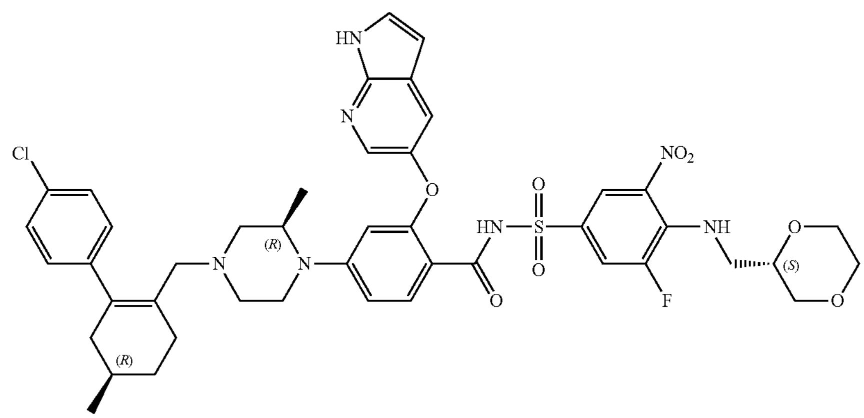
27
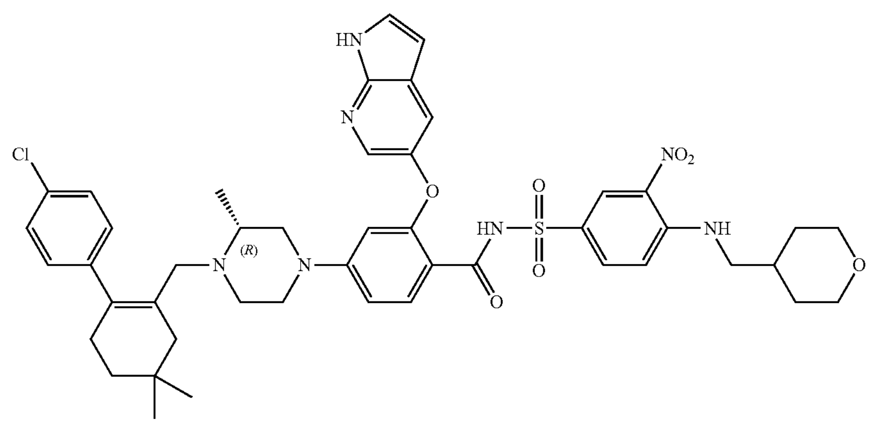
28
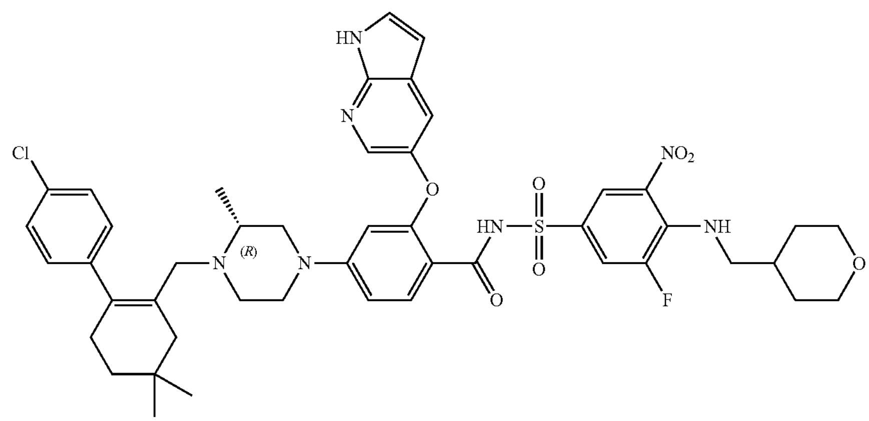

-continued
29
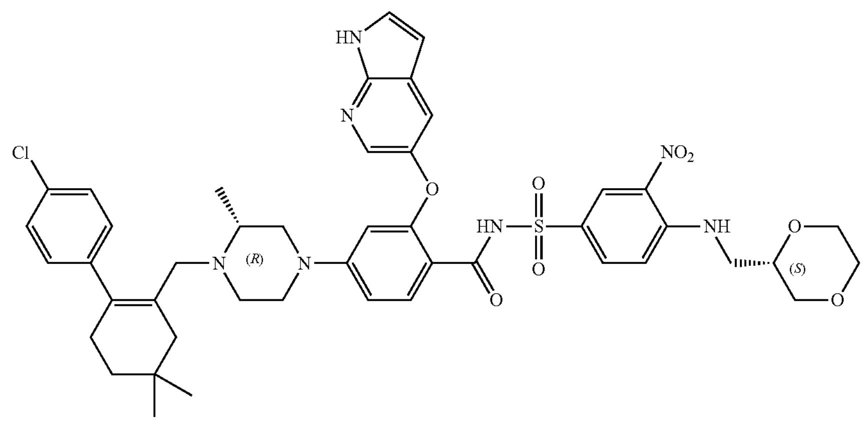
30
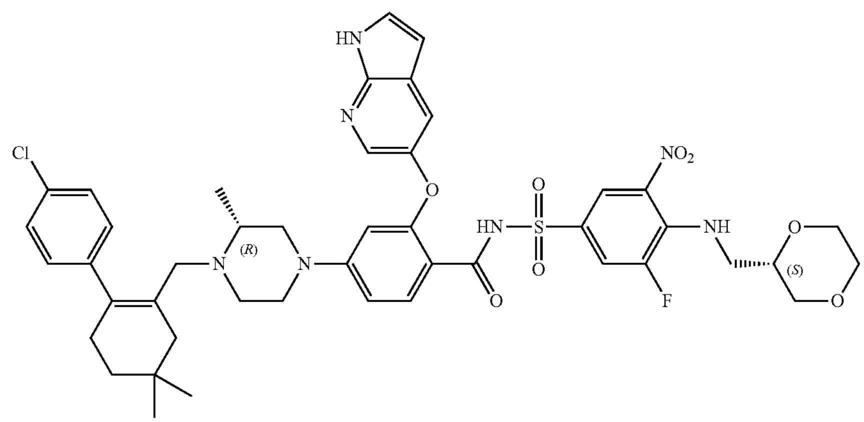
31
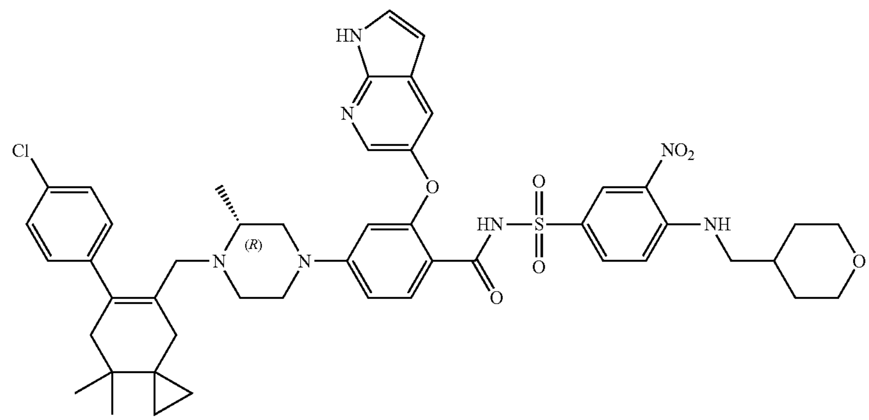

-continued
32
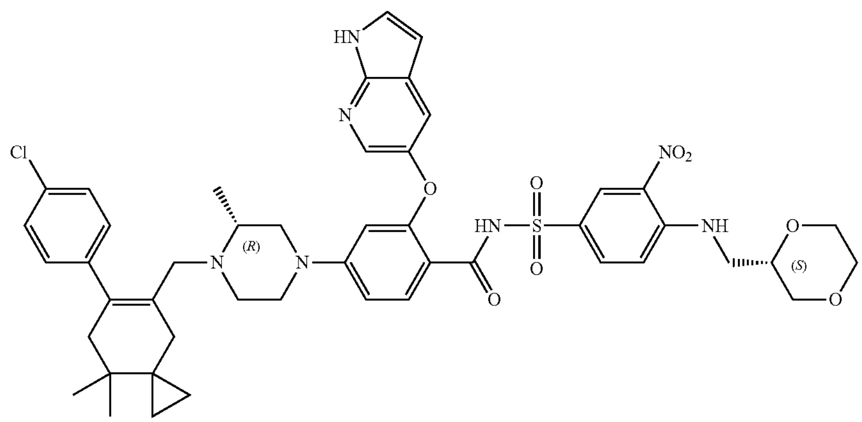
33
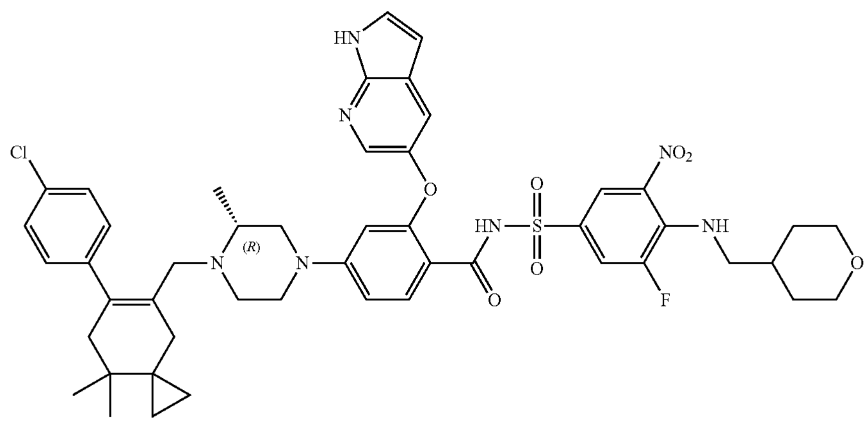
34
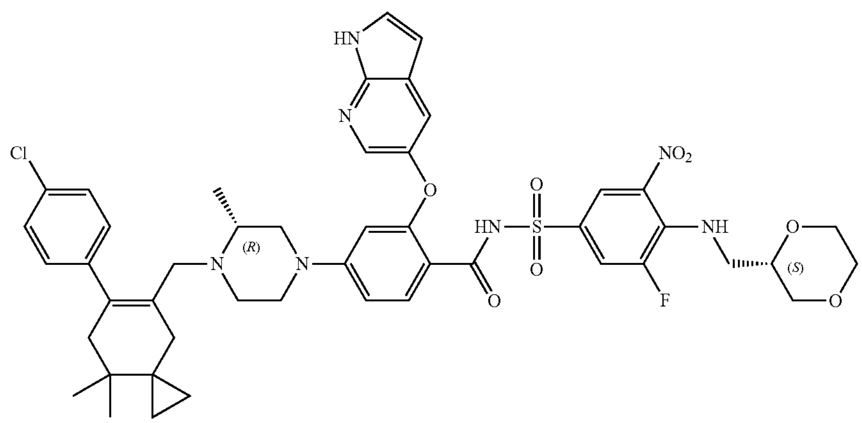

-continued
35
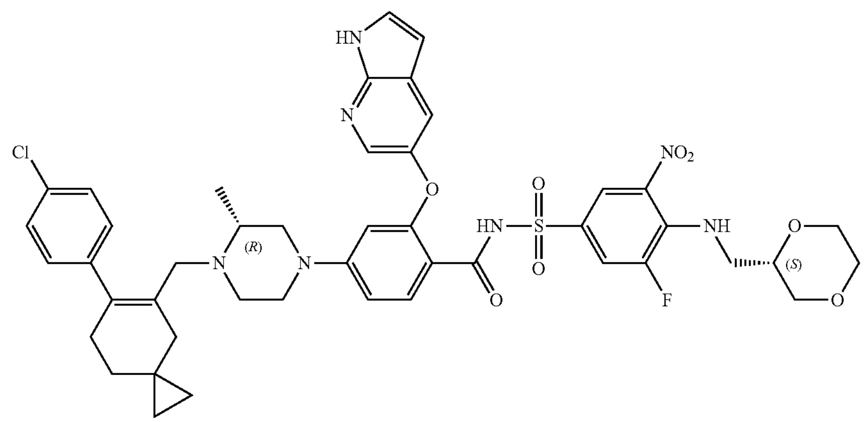
36
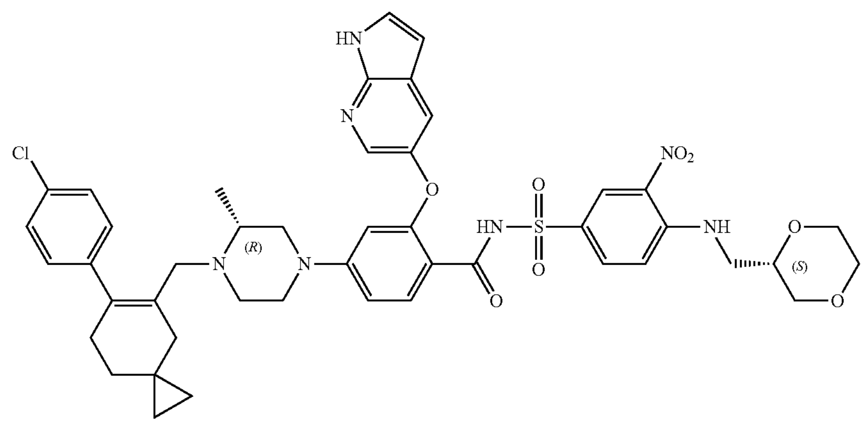
37
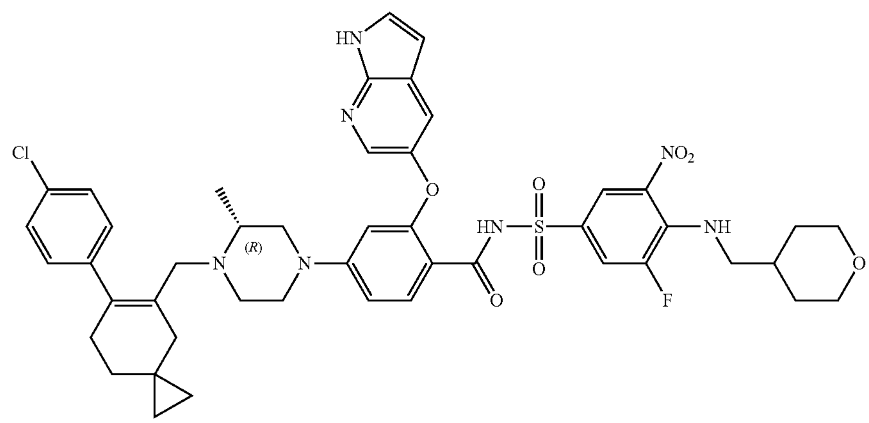

-continued
38
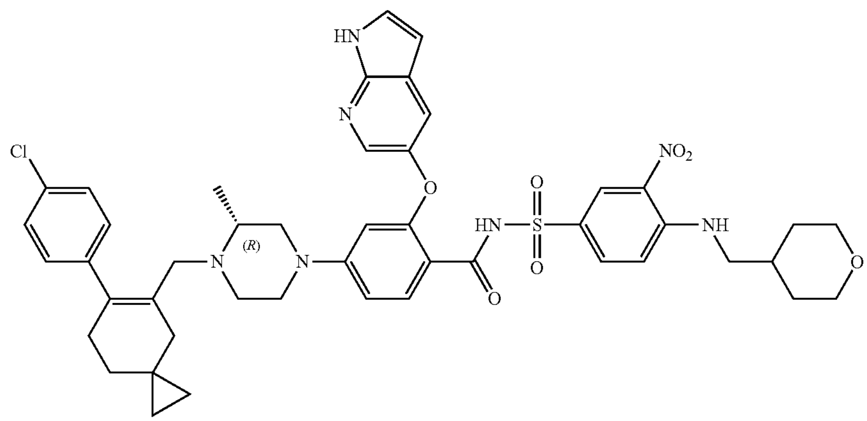
39
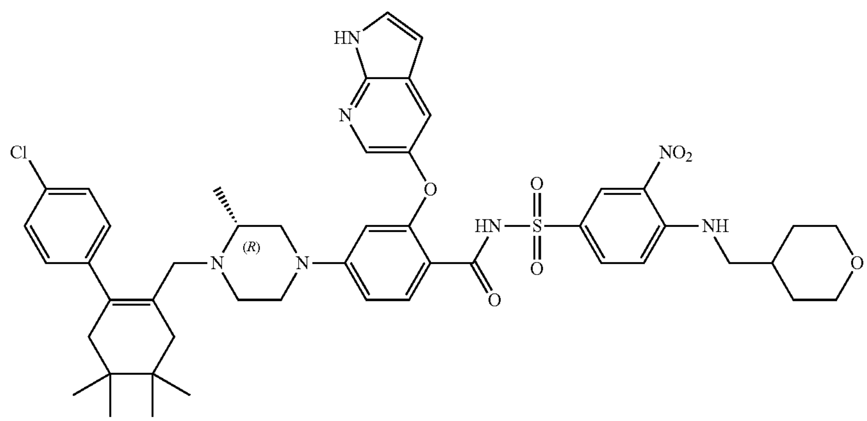
40
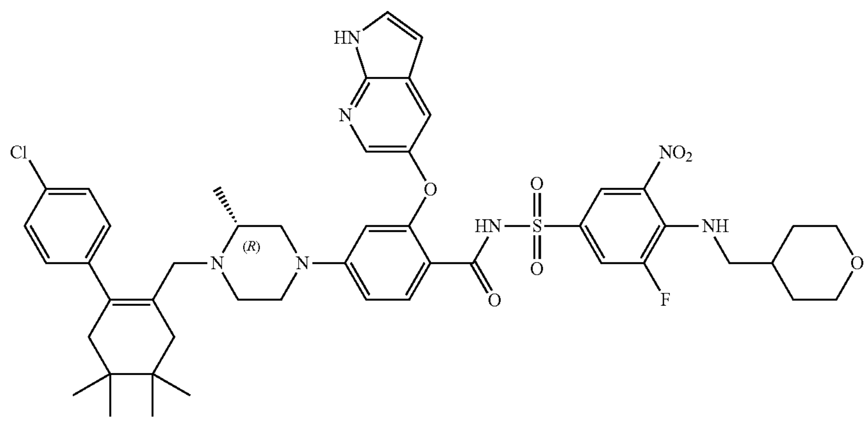

-continued
41
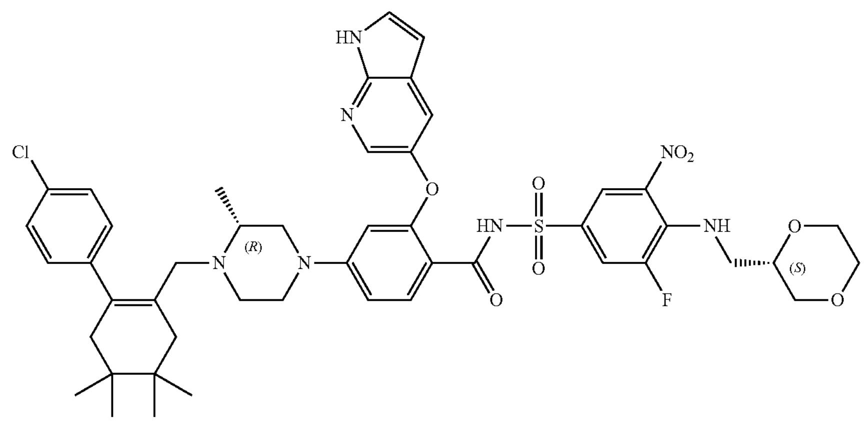
42
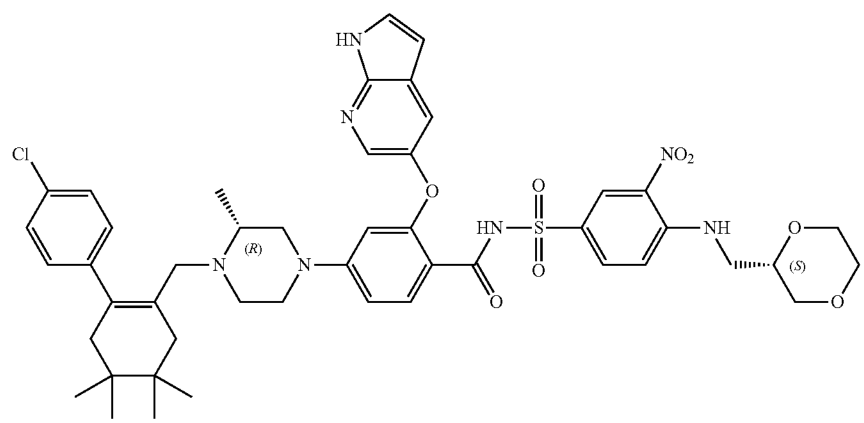
43
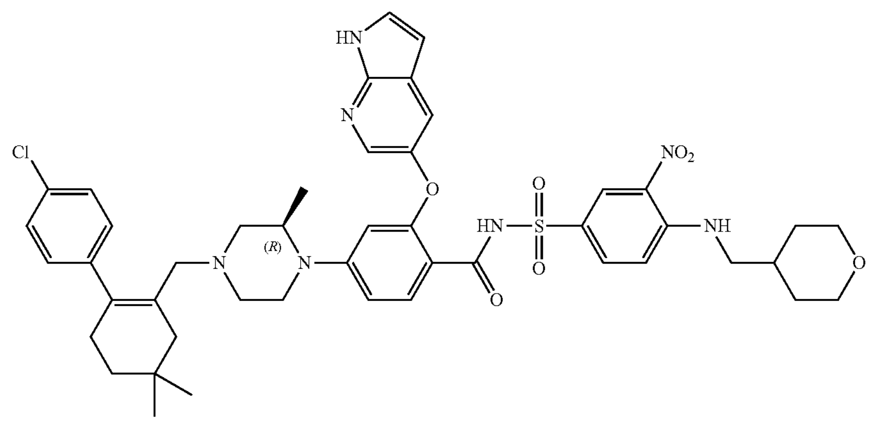

-continued
44
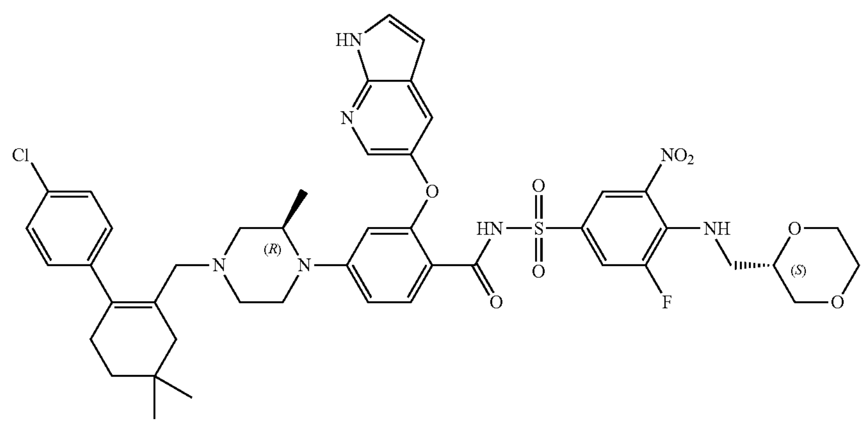
45
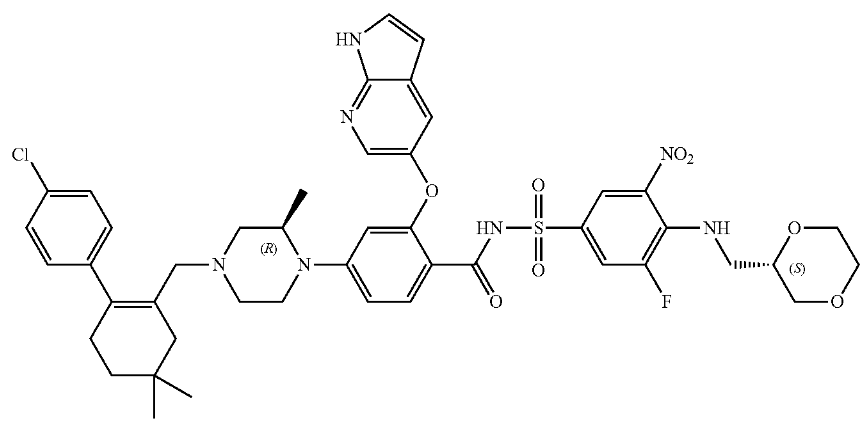
46
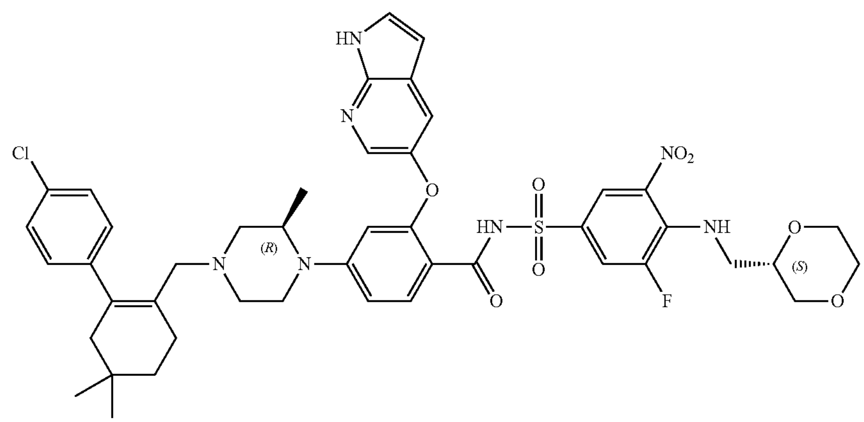

-continued

52

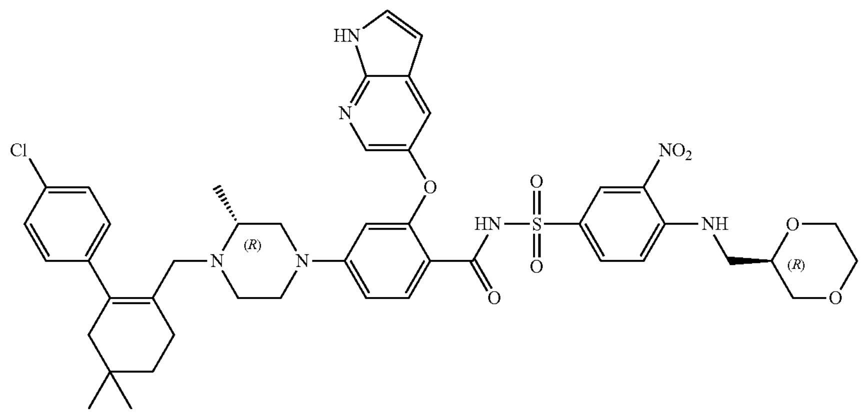

54

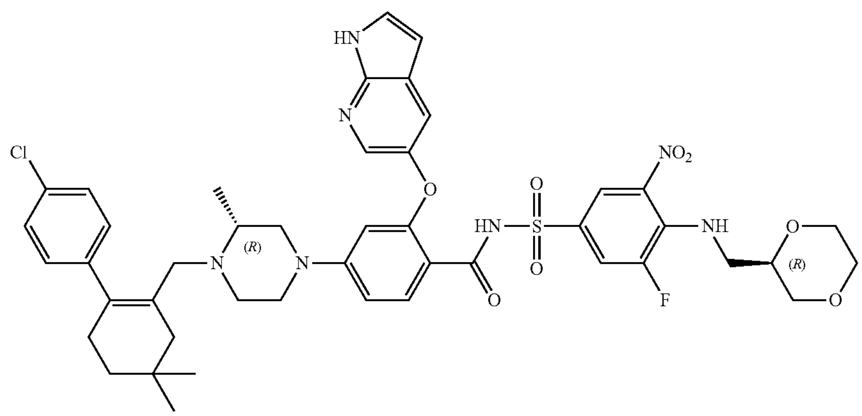

55

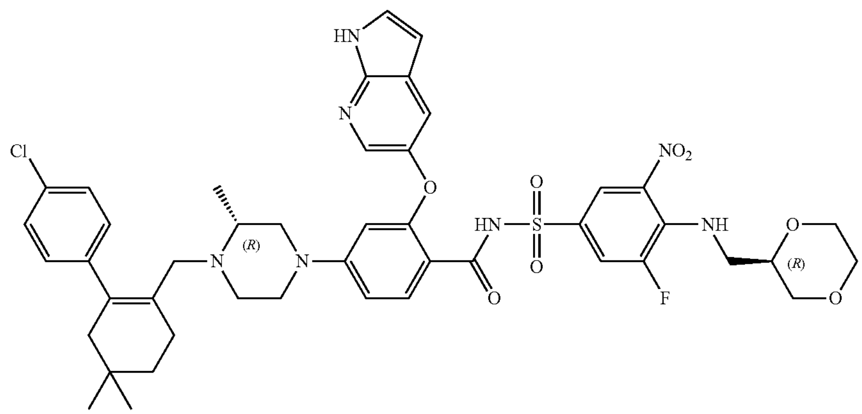

The present invention also relates to use of compounds of formula (I), isomers, prodrugs, solvates, stable isotope derivatives or pharmaceutically acceptable salts thereof according to any one of the embodiments of the present invention in the manufacture of a medicament as BCL-2 inhibitor.

The present invention also relates to use of a compound of formula (I) or an isomer, prodrug, solvate, stable isotope derivative or a pharmaceutically acceptable salt thereof according to any one of the embodiments of the present invention in the manufacture of a medicament for the treatment or prevention of BCL-2-mediated diseases such as tumors, the tumor is selected from hematological malignancies (especially acute lymphoblastic leukemia), lung cancer, breast cancer, ovarian cancer, prostate cancer, rectal cancer, pancreatic cancer, glioma.

The present invention further relates to a pharmaceutical composition comprising a compound of formula (I) or an isomer, prodrug, solvate, stable isotopic derivative or a pharmaceutically acceptable salt thereof, optionally one or more other BCL-2 inhibitors, and one or more pharmaceutically acceptable carriers, diluents and excipients.

The present invention also relates to the use of the pharmaceutical composition according to the present invention in the manufacture of a medicament for the treatment or prevention of BCL-2-mediated diseases, such as tumors, which are selected from hematological malignancies (especially acute lymphoblastic leukemia), lung cancer, breast cancer, ovarian cancer, prostate cancer, rectal cancer, pancreatic cancer, glioma.

The present invention also relates to a method of treating or preventing diseases mediated by BCL-2, comprising administering to a patient in need thereof a therapeutically effective amount of the compound or an isomer, prodrug, solvate, stable isotopic derivative or a pharmaceutically acceptable salt thereof as described in any one of the embodiments of the present invention; or pharmaceutical compositions of the present invention, said diseases such as tumors are selected from hematological malignancies (especially acute lymphoblastic leukemia), lung cancer, breast cancer, ovarian cancer, prostate cancer, rectal cancer, pancreatic cancer, glioma.

Another aspect of the present invention relates to a compound or an isomer, prodrug, solvate, stable isotope derivative or pharmaceutically acceptable salt thereof as described in any one of the embodiments of the present invention, for use in treating or preventing diseases mediated by BCL-2, such as tumors selected from hematological malignancies (especially acute lymphoblastic leukemia), lung cancer, breast cancer, ovarian cancer, prostate cancer, rectal cancer, pancreatic cancer, glioma.

Another aspect of the present invention relates to a pharmaceutical composition comprising a compound of formula (I) or an isomer, prodrug, solvate, stable isotope derivative or pharmaceutically acceptable salt thereof as described in any one of the embodiments of the present invention, optionally one or more other BCL-2 inhibitors, and one or more pharmaceutically acceptable carriers, diluents and excipients, for use in treating or preventing diseases mediated by BCL-2, such as tumors selected from hematological malignancies (especially acute lymphoblastic leukemia), lung cancer, breast cancer, ovarian cancer, prostate cancer, rectal cancer, pancreatic cancer, glioma.

Another aspect of the present invention relates to a compound of formula (I) or an isomer, prodrug, solvate, stable isotope derivative or pharmaceutically acceptable salt thereof as described in any one of the embodiments of the present invention for the treatment and/or prevention of BCL-2-mediated diseases. The BCL-2-mediated disease is such as tumors, the tumor is selected from hematological malignancies (especially acute lymphoblastic leukemia), lung cancer, breast cancer, ovarian cancer, prostate cancer, rectal cancer, pancreatic cancer, glioma.

According to the present invention, the medicament can be in any pharmaceutical dosage form, including but not limited to tablets, capsules, solutions, lyophilized dosage forms, and injections.

The pharmaceutical formulations of the present invention may be administered in dosage unit form containing a predetermined amount of active ingredient per dosage unit. Such a unit may contain, for example, from 0.5 mg to 1 gram, preferably from 1 mg to 700 mg, particularly preferably from 5 mg to 300 mg, of a compound of the invention, depending on the condition to be treated, the method of administration and the age, weight and condition of the patient. The formulations can be administered in dosage unit form containing a predetermined quantity of active ingredient per dosage unit. Preferred dosage unit formulations are those containing a daily dose or sub-dose, as indicated above, or a corresponding fraction thereof, of an active ingredient. Furthermore, pharmaceutical formulations of this type can be prepared using methods well known in the pharmaceutical art.

The pharmaceutical formulations of the present invention may be suitable for administration by any desired suitable method, such as oral (including buccal or sublingual), rectal, nasal, topical (including buccal, sublingual or transdermal), vaginal or parenteral (including subcutaneous, intramuscular, intravenous or intradermal) methods of administration. Such formulations can be prepared, for example, by combining the active ingredient with one or more excipients or one or more adjuvants, using all methods known in the art of pharmaceutical field.

Preparation Scheme

The present invention also provides methods for preparing the compounds.

scheme 1

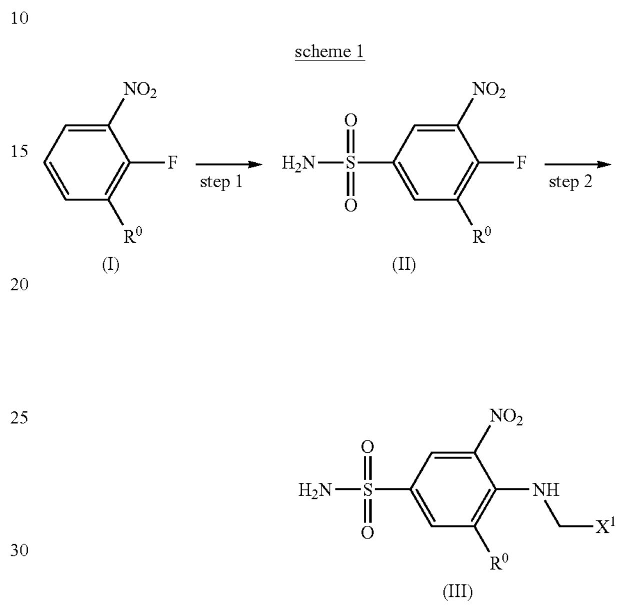

(I) (II)

(III)

The definitions of $R^0$ and $X^1$ are as described above;

Step 1:

Compound (I) was dissolved in chlorosulfonic acid, heated in an oil bath (120-150° C.) and reacted for 10-20 hours, cooled to room temperature, quenched with ice water, extracted with ethyl acetate, and the organic phase was dried and concentrated to give the crude product which was dissolved into anhydrous tetrahydrofuran, aqueous ammonia is added dropwise at low temperature (−80~-60° C.), and stirring is continued for 1-5 hours, the reaction mixture is acidified with hydrochloric acid to give compound (II);

Step 2:

Compound (II) and the corresponding amine were dissolved in a solvent (such as acetonitrile), a base (such as triethylamine or diisopropylethylamine, etc.) was added, and under the protection of an inert gas (such as nitrogen or argon), the reaction mixture was stirred at temperature of 25-60° C. for 10-20 hours to give compound (Ill); scheme 2 scheme 2

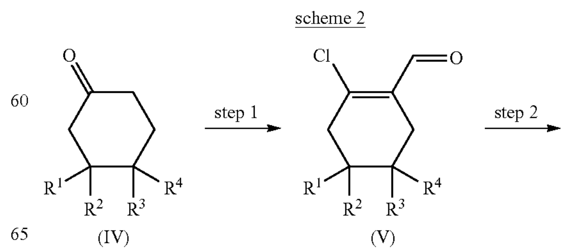

(IV) (V)

-continued

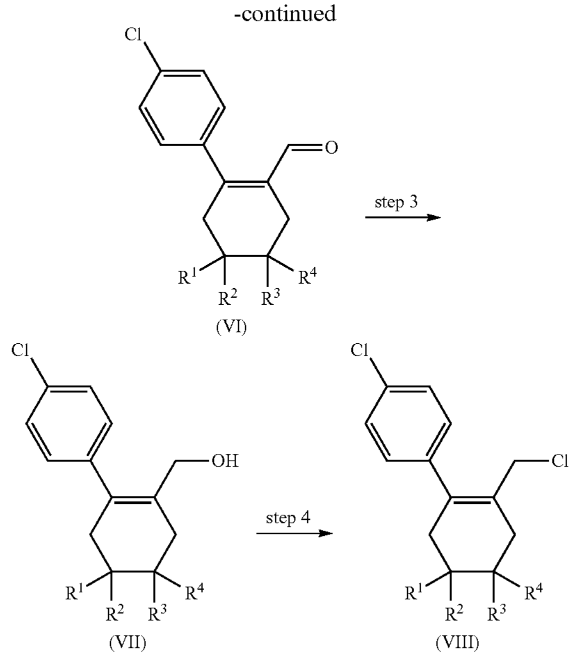

(VI)

(VII) (VIII)

The definitions of $R^1$, $R^2$, $R^3$, and $R^4$ are described above;

Step 1:

Phosphorus oxychloride was added dropwise to the solution of N,N-dimethylformamide in dichloromethane in an ice bath under nitrogen protection. After the addition, the mixture was stirred at room temperature for 30 minutes, cooled to 0° C. again, and the solution of compound (IV) in dichloromethane was added dropwise to the above mixture, and kept at the temperature from room temperature to 60° C. for 10-24 hours to give compound (V);

Step 2:

Under nitrogen protection, compound (V), p-chlorobenzeneboronic acid, bases such as potassium carbonate, a phase transfer catalyst such as tetra-n-butylammonium bromide and a catalyst such as palladium acetate were added to a solvent such as water. The system is evacuated and replaced with nitrogen for three times, heated to 40-100° C. and reacted for 2-10 hours to give compound (VI);

Step 3:

Compound (VI) was dissolved in a solvent such as tetrahydrofuran and methanol, a reducing agent such as sodium borohydride was added, and the mixture was stirred at room temperature for 1-5 hours to give compound (VII);

Step 4:

Compound (VII) was dissolved in a solvent such as dichloromethane, a chlorinating reagent such as thionyl chloride was added, and the mixture was stirred at room temperature for 10-24 hours to give compound (Vill).

Scheme 3

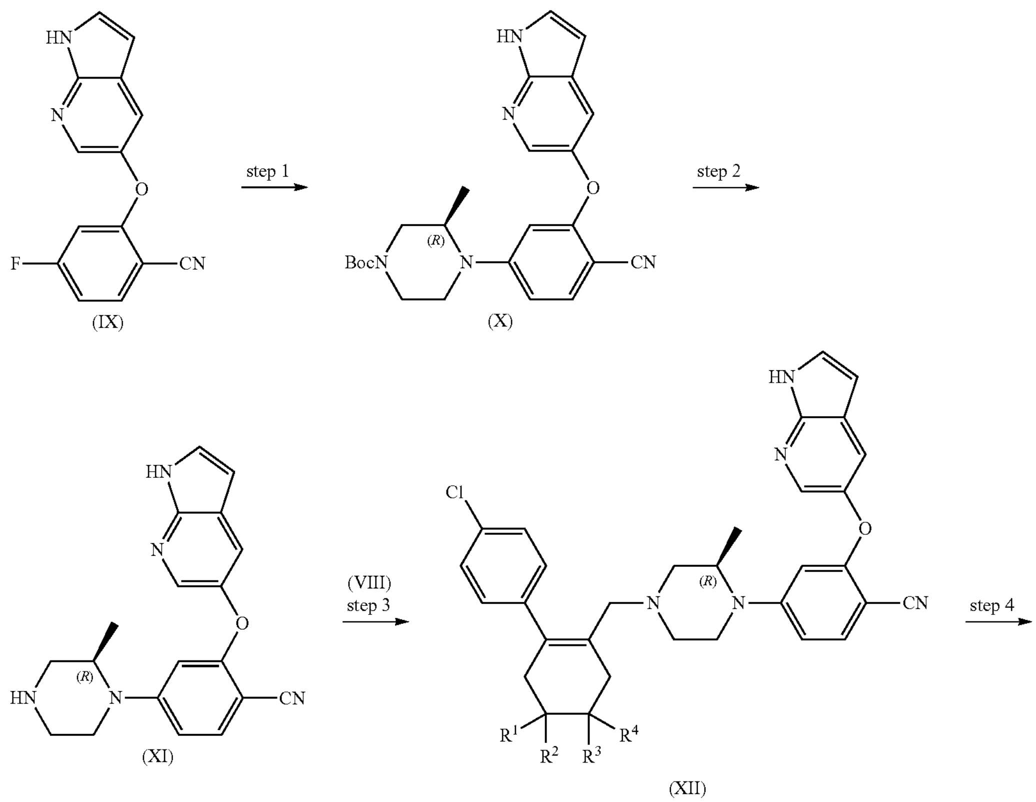

(IX) (X)

(XI) (XII)

-continued

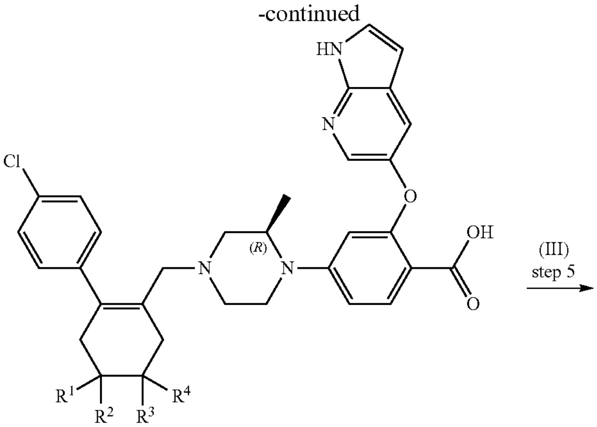

(XIII)

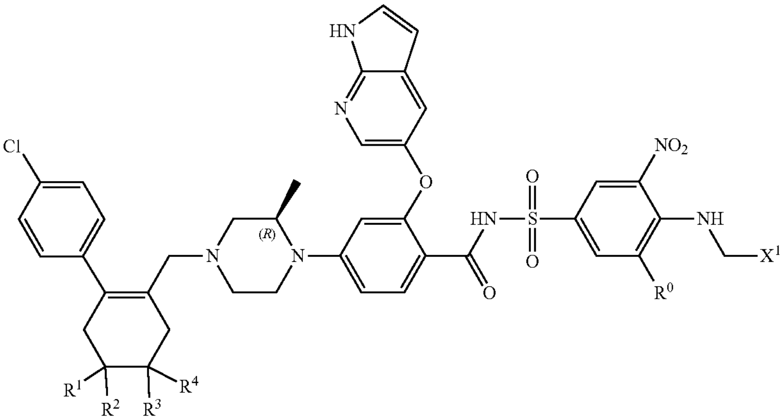

(XIV)

The definitions of $R^0$, $R^1$, $R^2$, $R^3$, $R^4$, and $X^1$ are described above;

Step 1:

Compound (IX) (the synthesis can be referred to: WO 2017212431) (0.51 g, 2.00 mmol) and (R)-tert-butyl 3-methylpiperazine-1-carboxylate were dissolved in a solvent such as dimethyl sulfoxide, a base such as dipotassium hydrogen phosphate was added at room temperature, and the reaction mixture was stirred at the temperature of 90-120° C. for 12-48 hours to give compound (X);

Step 2:

Compound (X) was added to a solution of an acid such as hydrogen chloride in 1,4-dioxane, and the mixture was stirred at room temperature for 1-3 hours to give compound (XI);

Step 3:

Compound (XI) and compound (VIII) were dissolved in a solvent such as acetonitrile, a base such as N,N-diisopropylethylamine was added, heated to 60-90° C., and stirred for 2-8 hours to give compound (XII);

Step 4:

Compound (XII) was dissolved in a solvent such as 2-butanol, a base such as sodium hydroxide was added, heated to 90-120° C. and the mixture was stirred for 12-36 hours, and then acidified with an acid such as hydrochloric acid to give compound (XIII);

Step 5:

Compound (XIII), compound (III), a condensation agent such as 1-ethyl-(3-dimethylaminopropyl)carbodiimide hydrochloride, a base such as 4-dimethylaminopyridine were dissolved in a solvent such as dichloromethane, and the mixture was stirred at room temperature for 12-36 hours to give compound (XIV).

Scheme 4

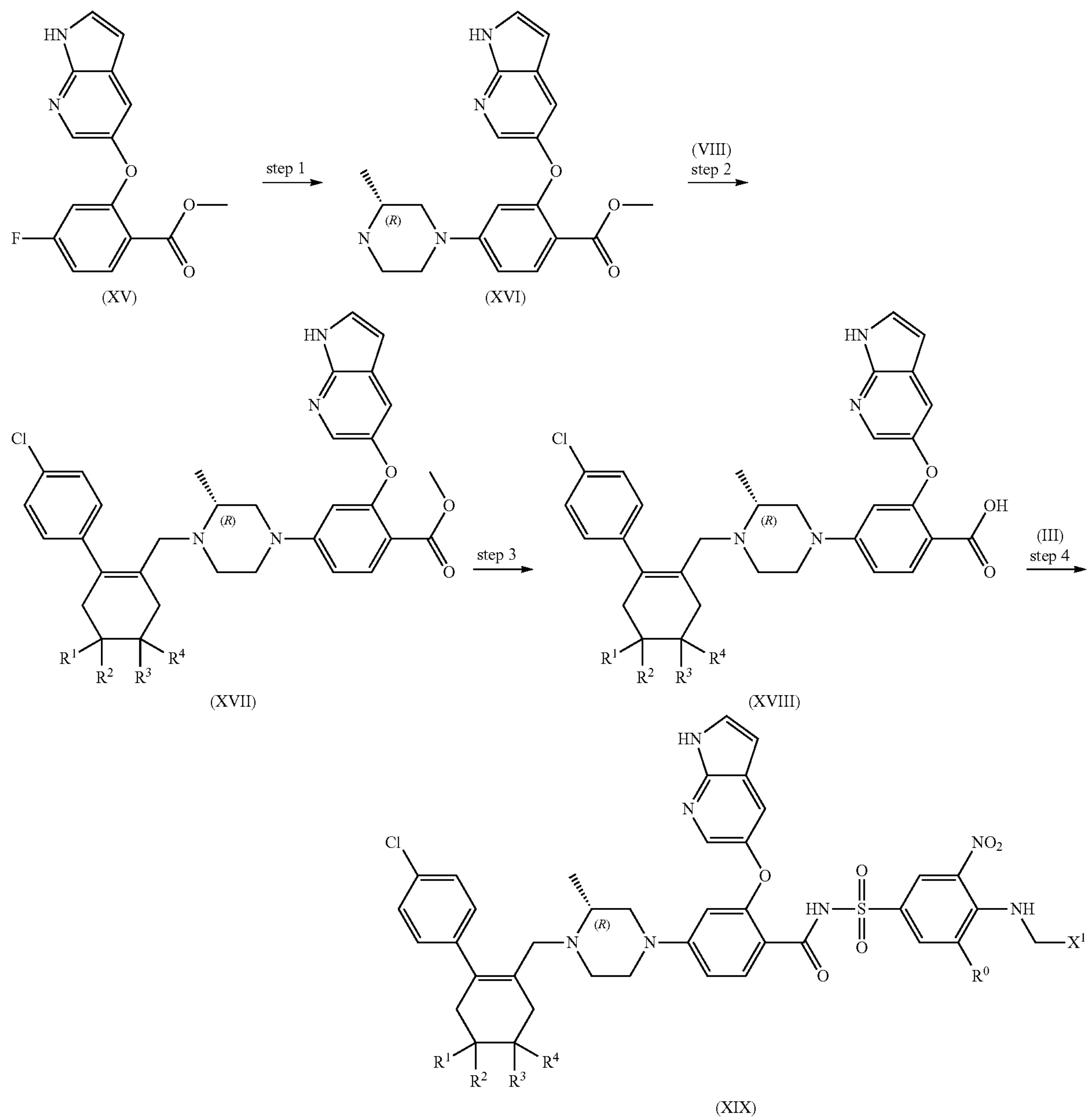

(XV) (XVI) (XVII) (XVIII) (XIX)

The definitions of $R^0$, $R^1$, $R^2$, $R^3$, $R^4$ and $X^1$ are described above;

Step 1:

Compound (XV) (the synthesis can be referred to: *Journal of Organic Chemistry,* 84(8), 4814-4829; 2019) (0.51 g, 2.00 mmol) and (R)-2-methylpiperazine were dissolved in a solvent such as dimethylpiperazine, a base such as N,N-diisopropylethylamine was added at room temperature, and the mixture was stirred at a temperature of 50-100° C. for 12-24 hours to give compound (XVI);

Step 2:

Compound (XVI) and compound (VIII) were dissolved in a solvent such as acetonitrile, a base such as N,N-diisopropylethylamine was added, the mixture was heated to 50-90° C. and stirred for 8-24 hours to give compound (XVII);

Step 3:

Compound (XVII) was dissolved in a solvent such as water, methanol and tetrahydrofuran, a base such as lithium hydroxide was added, the mixture was heated to 50-90° C. and stirred for 1-5 hours. Then the mixture was acidified with an acid such as hydrochloric acid to give compound (XVIII);

Step 4:

Compound (XVIII), compound (III), a condensation agent such as 1-ethyl-(3-dimethylaminopropyl)carbodiimide hydrochloride, a base such as 4-dimethylaminopyridine were dissolved in a solvent such as dichloromethane. The mixture was stirred at room temperature for 12-36 hours to give compound (XIX).

DETAILED DESCRIPTION OF THE INVENTION

Definitions

Unless stated to the contrary, the following terms used in the specifications and claims have the following meanings. Groups not specifically defined in the present invention have the meanings generally represented in the art known to those skilled in the art.

The "Cx-Cy" used in the present invention represents a range of carbon atoms, where x and y are both integers, for example, C3-C8 cycloalkyl refers to a cycloalkyl group having 3-8 carbon atoms, —C0-C2 alkyl refers to an alkyl group having 0-2 carbon atoms, wherein —CO alkyl refers to a chemical single bond.

In the present invention, the term "alkyl" refers to saturated aliphatic hydrocarbon groups, including linear and branched chain groups of 1 to 20 carbon atoms, for example, linear and branched chain groups of 1 to 18 carbon atoms, 1 to 12 carbon atoms, 1 to 8 carbon atoms, 1 to 6 carbon atoms, or 1 to 4 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, and various branched isomers thereof, etc. Alkyl groups can be optionally substituted or unsubstituted.

In the present invention, the term "cycloalkyl" refers to a saturated monocyclic or polycyclic hydrocarbon group comprising 3 to 12 ring atoms, such as 3 to 12, 3 to 10, 3 to 8 or 3 to 6 ring atoms, or can be a 3-, 4-, 5-, or 6-membered ring. Non-limiting examples of monocyclic groups include cyclopropyl, cyclobutyl, cyclopentyl, cyclohexyl, cycloheptyl, cyclooctyl, and the like. Cycloalkyl groups can be optionally substituted or unsubstituted.

In the present invention, the term "heterocyclyl" refers to a saturated or partially unsaturated monocyclic or polycyclic hydrocarbon group comprising 3 to 20 ring atoms, for example, 3 to 16, 3 to 12, 3 to 10, 3 to 8, or 3 to 6 ring atoms, one or more of the ring atom is selected from heteroatoms such as nitrogen, oxygen, or S(O)m (where m is an integer from 0 to 2), excluding the ring moiety of —O—O—, —O—S— or —S—S—, the remaining ring atoms being carbon. It preferably contains 3 to 12 ring atoms, of which 1 to 4 are heteroatoms, more preferably the heterocyclyl ring contains 3 to 10 ring atoms, more preferably 3 to 8 ring atoms, most preferably a 5- or 6-membered ring, of which 1-4 ring atoms are heteroatoms, more preferably 1-3 ring atoms are heteroatoms, and most preferably 1-2 ring atoms are heteroatoms. Non-limiting examples of monocyclic heterocyclyl groups include oxetanyl, pyrrolidinyl, piperidinyl, 4-piperidinyl, piperazinyl, 1,4-dioxanyl, morpholinyl, 2-morpholinyl, 4-morpholinyl, thiomorpholinyl, pyranyl, tetrahydropyranyl, 4-tetrahydropyranyl, homopiperazinyl, dioxanyl, 2-dioxanyl, etc. Polycyclic heterocyclyls include spiro, fused and bridged heterocyclyls. Heterocyclyl groups can be optionally substituted or unsubstituted.

In the present invention, the term "heterocyclylene" refers to a substituted or unsubstituted heterocyclyl having two terminal monovalent group cores, obtained by removing one hydrogen atom from each of the two terminal atoms. The heterocyclyl group has the meanings set forth above. Non-limiting examples of "heterocyclylene" include pyrrolidylene, piperidinylene, piperazinylene, morpholinylene, and the like.

In the present invention, the term "halogen" refers to fluorine, chlorine, bromine or iodine.

In the present invention, "optional" or "optionally" means that the subsequently described event or circumstance can, but not necessarily occur, and the description includes instances where the event or circumstance occurs or instances where it does not. For example, "a heterocyclic group optionally substituted with an alkyl group" means that an alkyl group may, but no necessarily, be present, and the description includes the case where the heterocyclic group is substituted with an alkyl group and the case where the heterocyclic group is not substituted with an alkyl group.

In the present invention, "substituted" means that one or more hydrogen atoms in a group, preferably up to 5, more preferably 1 to 3 hydrogen atoms, independently of each other, are substituted by the corresponding number of substituents. It goes without saying that the substituents are only in their possible chemical positions, and the person skilled in the art can determine (either experimentally or theoretically) possible or impossible substitutions without undue effort. For example, amino or hydroxyl groups with free hydrogens may be unstable when combined with carbon atoms with unsaturated (eg, olefinic) bonds.

The substituents include, but are not limited to, the various groups as described above.

The compounds claimed in the present invention include not only the compounds themselves, but also isomers, prodrugs, solvates, stable isotope derivatives or pharmaceutically acceptable salts thereof.

The "pharmaceutical composition" of the present invention refers to a mixture comprising one or more of the compounds of the present application, isomers, prodrugs, solvates, stable isotope derivatives or pharmaceutically acceptable salts thereof and other chemical components. Other components such as pharmaceutically acceptable carriers, diluents and excipients. The purpose of the pharmaceutical composition is to facilitate the administration to the organism, facilitate the absorption of the active ingredient and then exert the biological activity.

When used in the specification, the term "comprising" includes "consisting of."

The "room temperature" in the present invention refers to 15-30° C.

The "stable isotopic derivatives" of the present invention include: isotopically substituted derivatives obtained by replacing any hydrogen atom in formula (I) with 1-5 deuterium atoms, isotopically substituted derivatives obtained by replacing any carbon atom in formula (I) with 1-3 carbon-14 atoms, or isotopically substituted derivatives obtained by replacing any oxygen atom in formula (I) with 1-3 oxygen-18 atoms.

"Pharmaceutically acceptable salts" according to the present invention have been discussed in Berge, et al., "Pharmaceutically acceptable salts", J. Pharm. Sci., 66, 1-19 (1977) and are apparent to medicinal chemists. The salts are substantially non-toxic and provide the desired pharmacokinetic properties, palatability, absorption, distribution, metabolism or excretion and the like.

The pharmaceutically acceptable salts of the present invention can be synthesized by general chemical methods.

In general, salts can be prepared by reacting the free base or acid with equivalent or excess of acid (inorganic or organic) or base in a suitable solvent or solvent composition.

The "prodrug" in the present invention refers to a compound which transforms into the original active compound after metabolism in the body. Typically, a prodrug is an inactive substance, or is less active than the active parent compound, but can provide ease of manipulation, administration, or improved metabolic properties.

The "isomers" as used herein refers to the tautomers, mesomers, racemates, enantiomers, diastereomers of the compound of formula (I) of the present invention and mixtures thereof. All these isomers, including stereoisomers and geometric isomers, are included in the present invention. The geometric isomers include cis and trans isomers.

The "solvate" as used herein refers to the association of one or more solvent molecules with a compound of the present invention or a salt thereof. Examples of solvents that form pharmaceutically acceptable solvates include, but are not limited to, water, isopropanol, ethanol, methanol, ethyl acetate, acetic acid, and the like.

The present invention includes any polymorphs of the compounds or salts thereof, as well as any hydrates or other solvates.

In the present invention, the term "patient" generally refers to mammals, especially humans.

In the present invention, the term "tumor" includes benign tumors and malignant tumors, such as cancer.

In the present invention, the term "cancer" includes various tumors mediated by BCL-2, including, but not limited to, hematological malignancies (especially acute lymphoblastic leukemia), lung cancer, breast cancer, ovarian cancer, prostate cancer, rectal cancer, pancreatic cancer, brain glioma.

In the present invention, the term "therapeutically effective amount" is meant to include the amount of the compound of the present invention effective to treat or prevent BCL-2 mediated diseases.

EXAMPLES

The present invention is further described below by way of examples, but the present invention is not meant to be limited by the scope of the described examples. The experimental methods that do not specify specific conditions in the following examples are performed according to conventional methods and conditions, or selected according to the product description.

The structures of all compounds of the present invention can be identified by nuclear magnetic resonance ($^1$H NMR) and/or mass spectrometry (MS).

$^1$H NMR chemical shifts (6) are reported in ppm (parts per million). NMR is performed on a Bruker AVANCE III-400 MHz spectrometer. Suitable solvents are selected from deuterated chloroform ($CDCl_3$), deuterated methanol ($CD_3OD$), deuterated dimethyl sulfoxide (DMSO-$d^6$), etc., with tetramethylsilane as internal standard (TMS).

Low resolution mass spectra (MS) is determined by an Agilent 1260 HPLC/6120 mass spectrometer using an Agilent ZORBAX XDB-C18, 4.6×50 mm, 3.5 μm.

Gradient elution condition 1:0: 95% solvent A1 and 5% solvent B1, 1-2: 5% solvent A1 and 95% solvent B1; 2.01-2.50: 95% solvent A1 and 5% solvent B1. Percentage is the volume percent of a solvent in the total solvent volume. Solvent A1: 0.01% formic acid aqueous solution; solvent B1: 0.01% formic acid in acetonitrile; the percentage is the volume percentage of the solute in the solution.

The thin layer silica gel plate is Yantai Huanghai HSGF254 or Qingdao GF254 silica gel plate. Yantai Yellow Sea 100-200 or 200-300 mesh silica gel is generally used as a carrier in column chromatography.

Preparative liquid chromatography (prep-HPLC) is performed by use of Waters SQD2 mass spectrometer-guided high-pressure liquid chromatography, XBridge-C18; 30×150 mm preparative column, 5 μm;

Method 1: acetonitrile-water (0.2% formic acid), flow rate 25 mL/min;

Method 2: acetonitrile-water (0.8% ammonium bicarbonate), flow rate 25 mL/min;

The known starting materials of the present invention can be synthesized by adopting or following methods known in the art, or can be purchased from Acros Organics, Aldrich Chemical Company, Accela ChemBio Inc, Shanghai Bide Medicine, Shanghai Allatin Chemical, Shanghai Meryer Chemical, J&K Scientific, Energy Chemical and other companies. Venetoclax was purchased from Wuxi labnetwork (Wuhan) Chemical Technology Co., Ltd.

If there is no special instruction in the examples, the solvent used in the reaction is an anhydrous solvent, wherein the anhydrous tetrahydrofuran is achieved by treating commercially available tetrahydrofuran by use of sodium block as the water scavenger, benzophenone as the indicator, and refluxing under argon protection until the solution shows blue-purple, then the anhydrous tetrahydrofuran is collected by distillation, and stored at room temperature under argon protection. Other anhydrous solvents are purchased from Energy Chemicals and J&K Scientific. The transfer and use of all anhydrous solvents should be carried out under argon protection unless otherwise specified.

Unless otherwise specified in the examples, the reactions were all carried out in an argon atmosphere or a nitrogen atmosphere.

Argon or nitrogen atmosphere means that the reaction flask is connected to an argon or nitrogen balloon with a volume of about 1 L.

Hydrogen atmosphere means that the reaction flask is connected to a hydrogen balloon with a volume of about 1 L.

The hydrogenation reaction is usually evacuated and filled with hydrogen, and the operation is repeated 3 times.

Unless otherwise specified in the examples, the reaction temperature is room temperature, and the temperature range is 15° C.-30° C.

The monitoring of the reaction progress in the examples adopts thin layer chromatography (TLC), and the systems of the eluents used in the reaction are A: dichloromethane and methanol system; B: petroleum ether and ethyl acetate system. The volume ratio of the solvent is adjusted according to the polarity of the compound.

The eluent system for column chromatography and the eluents for thin layer chromatography used to purify the compound include A: dichloromethane and methanol system; B: petroleum ether and ethyl acetate system. The volume ratio of the solvent is adjusted according to the polarity of the compound and can also be adjusted by adding a small amount of triethylamine and an acidic or basic reagent.

Intermediate 1

3-Fluoro-5-nitro-4-(((tetrahydro-2H-pyran-4-yl)methyl)amino)benzensulfonamide

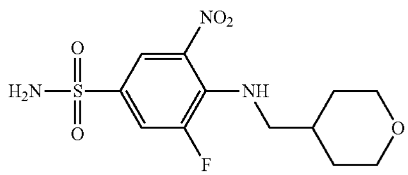

1

Step 1

3,4-Difluoro-5-nitrobenzenesulfonamide 1,2-Difluoro-3-nitrobenzene (10.00 g, 62.89 mmol) was dissolved in chlorosulfonic acid (21 mL). The mixture was heated to 150° C. and stirred under reflux for 10 hours. After cooled to room temperature, a saturated aqueous sodium bicarbonate solution was added to the reaction mixture in an ice bath to adjust the pH to about 7. The reaction mixture was extracted with dichloromethane (100 mL×3), and the organic phase was washed with brine (100 mL×2), dried over anhydrous sodium sulfate, filtered and concentrated to obtain the crude product 3,4-difluoro-5-nitrobenzenesulfonyl chloride. In a 1000 mL three-necked flask, isopropanol (200 mL) and aqueous ammonia (5 mL, 37%) were added and the mixture was stirred at −78° C. for 10 minutes. The crude 3,4-difluoro-5-nitrobenzenesulfonyl chloride obtained was dissolved in isopropanol (30 mL). The resulting solution was slowly added dropwise into the above mixture of isopropanol and aqueous ammonia at −78° C. The mixture was then stirred at −78° C. for two hours after the addition. Dilute hydrochloric acid (1 N) was added to the reaction mixture to adjust the pH to about 6. The reaction mixture was warmed to room temperature, concentrated under reduced pressure to remove most of the isopropanol solvent. Water was added and the solid was precipitated out. The crude solid product was obtained by filtration. The crude product was triterated with dichloromethane to obtain the target product 3,4-difluoro-5-nitrobenzenesulfonamide (4.90 g, yellow solid). Yield: 33%.

$^1$H NMR (400 MHz, DMSO-$d^6$) δ 8.38-8.36 (m, 1H), 8.29-8.26 (m, 1H), 7.84 (s, 2H).

Step 2

3-Fluoro-5-nitro-4-(((tetrahydro-2H-pyran-4-yl)methyl)amino)benzenesulfonamide 3,4-difluoro-5-nitrobenzenesulfonamide (1.55 g, 6.51 mmol), (tetrahydro-2H-pyran-4-yl)methanamine (0.89 g, 7.73 mmol), N,N-diisopropylethylamine (3.91 g, 30.31 mmol) and acetonitrile (20.0 mL) were mixed and stirred at 40° C. for 2 hours. The solvents were evaporated. The residue was quenched with 50 mL of water, and extracted with ethyl acetate (60 mL×2). The combined organic phase was washed with brine (50 mL×3). The organic phase was dried with anhydrous sodium sulfate, filtered and dried under reduced pressure to give the crude product. The rude product was purified by column chromatography (petroleum ether/ethyl acetate=1:1) to give the target product 3-fluoro-5-nitro-4-(((tetrahydro-2H-pyran-4-yl)methyl)amino) benzenesulfonamide (1.66 g, yellow solid). Yield: 76%.

MS m/z (ESI): 334 [M+1];

$^1$H NMR (400 MHz, DMSO-$d^6$) δ 8.33-8.30 (m, 2H), 7.76-7.74 (m, 1H), 7.45 (s, 2H), 3.86-3.84 (m, 2H), 3.50-3.45 (m, 2H), 3.29-3.23 (m, 3H), 1.59-1.57 (m, 2H), 1.25-1.20 (m, 2H).

The synthesis of intermediate 2 can be referred to that of intermediate 1.

| Example and name | structure | MS & $^1$H NMR |
|---|---|---|
| Intermediate 2 (S)-4-(((1,4-dioxan-2-yl)methyl)amino)-3-fluoro-5-nitrobenzene sulfonamide | 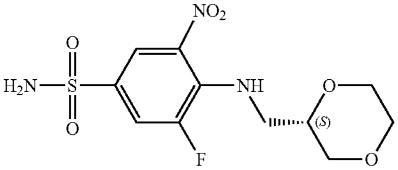 | MS m/z (ESI): 336 [M + 1]; $^1$H NMR (400 MHz, $CD_3OD$) δ 8.47 (s, 1H), 7.74-7.70 (m, 1H), 3.84-3.78 (m, 3H), 3.75-3.69 (m, 3H), 3.62-3.58 (m, 2H), 3.43-3.40 (m, 1H). |

Intermediate 3

3-Fluoro-5-nitro-4-(((1-(3-oxetanyl)piperidin-4-yl)methyl)amino)benzenesulfonamide

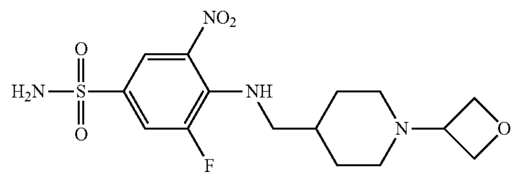

3

Step 1

3-Fluoro-5-nitro-4-((piperidin-4-ylmethyl)amino)benzenesulfonamide

Tert-butyl 4-(((2-fluoro-6-nitro-4-sulfamoylphenyl)amino)methyl)piperidin-1-carboxylate (refer to the synthetic procedure of Intermediate 1 for the synthesis) (0.49 g, 1.12 mmol), trifluoroacetic acid (3 mL) and dichloromethane (9 mL) were mixed, and stirred at room temperature for half the hour. The solvent was evaporated. The residue was adjusted to neutral with triethylamine, and the solvent was evaporated again to obtain crude 3-fluoro-5-nitro-4-((piperidin-4-ylmethyl)amino) benzenesulfonamide (0.35 g, yellow oil). This crude was used directly in the next reaction without further purification. MS m/z (ESI): 333 [M+1].

Step 2

3-Fluoro-5-nitro-4-(((1-(3-oxetanyl)piperidin-4-yl) methyl) amino)benzenesulfonamide 3-Fluoro-5-nitro-4-((piperidin-4-ylmethyl)amino)benzenesulfonamide (0.35 g, 1.05 mmol), oxetan-3-one (0.23 g, 3.15 mmol), sodium cyanoborohydride (0.23 g, 5.23 mmol) and methanol (8 mL) were mixed and stirred at room temperature for 1.5 hours. The mixture was quenched with 10 mL of water and extracted with ethyl acetate (10 mL×2). The combined organic phase was washed with brine (10 mL). The organic phase was dried over anhydrous sodium sulfate, filtered and dried by rotary evaporation. The residue was purified by column chromatography (petroleum ether/ethyl acetate=3:1) to obtain the desired product 3-fluoro-5-nitro-4-(((1-(3-oxetanyl)piperidin-4-yl)methyl)amino)benzenesulfonamide (0.32 g, yellow solid). Yield: 78%.

MS m/z (ESI): 389 [M+1];

$^1$H NMR (400 MHz, CD3OD) δ 8.47-8.46 (m, 1H), 7.72-7.70 (m, 1H), 4.68-4.65 (m, 2H), 4.60-4.59 (m, 2H), 3.57-3.55 (m, 2H), 3.49-3.45 (m, 1H), 2.83-2.80 (m, 2H), 1.89-1.78 (m, 3H), 1.42-1.20 (m, 4H).

Intermediate 4

(R)-4'-Chloro-6-(chloromethyl)-3-methyl-2,3,4,5-tetrahydro-1,1'-biphenyl

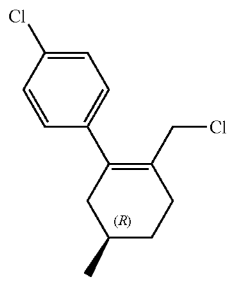

Step 1

(R)-2-Chloro-4-methylcyclohex-1-ene-1-carbaldehyde

N,N-Dimethylformamide (0.59 g, 8.00 mmol) was dissolved in dichloromethane (10 mL) and cooled to 0° C. in an ice bath, phosphoryl trichloride (0.92 g, 6.00 mmol) was added dropwise. The reaction mixture was stirred at 0° C. for 30 minutes, then warmed to room temperature and stirred for another 3 hours. The reaction mixture was cooled to 0° C., the solution of (R)-3-methylcyclohexan-1-one (reference for the synthesis: Tetrahedron 73 (2017) 3202-3212) (0.45 g, 4.0 mmol) in dichloromethane (5 mL) was added slowly. The reaction mixture was warmed slowly to room temperature and stirred for 18 hours. The reaction mixture was quenched by adding saturated aqueous sodium bicarbonate (10 mL), concentrated to remove dichloromethane, and ethyl acetate (25 mL) and water (15 mL) were added. The organic phase was separated, and the aqueous phase was extracted with ethyl acetate (25 mL×2). The combined organic phase was washed with brine (20 mL×2), dried over anhydrous sodium sulfate, filtered and concentrated to obtain the target compound (R)-2-chloro-4-methylcyclohex-1-ene-1-carbaldehyde (0.45 g, light yellow liquid) as a crude product.

MS m/z(ESI): 159 & 161 [M+1];

$^1$H NMR (400 MHz, $CDCl_3$) δ 10.20 (s, 0.8H), 10.18 (s, 0.2H), 2.63-2.47 (m, 2H), 2.29-2.26 (m, 1H), 2.24-2.15 (m, 1H)), 1.90-1.77 (m, 2H), 1.27-1.21 (m, 1H), 1.03 (d, J=6.4 Hz, 3H).

Step 2

(R)-4'-Chloro-5-methyl-3,4,5,6-tetrahydro-[1,1'-biphenyl]-2-carbaldehyde

To a single-necked flask, (R)-2-chloro-4-methylcyclohex-1-ene-1-carbaldehyde (0.45 g, 2.80 mmol), p-chlorophenylboronic acid (0.44 g, 2.80 mmol), tetrabutyl ammonium bromide (0.91 g, 2.80 mmol), potassium carbonate (1.17 g, 8.50 mmol), palladium acetate (0.16 g, 0.70 mmol) and water (15 mL) were added sequentially. The reaction was flushed with nitrogen for three times, heated to 45° C. and kept at this temperature for 4 hours. The reaction mixture was cooled to room temperature, ethyl acetate (25 mL) was added, the organic phase was separated. The aqueous phase was extracted with ethyl acetate (25 mL), the combined organic extracts were washed with saturated brine (15 mL), dried over anhydrous sodium sulfate and filtered. The filtrate was evaporated and the residue was purified by column chromatography (petroleum ether:ethyl acetate=96:4) to obtain the target compound (R)-4'-chloro-5-methyl-3,4,5,6-tetrahydro-[1,1'-biphenyl]-2-carbaldehyde (0.45 g, pale yellow oil), yield 67.5%.

MS m/z(ESI): 235 & 237 [M+1];

$^1$H NMR (400 MHz, $CDCl_3$) δ 9.41 (s, 0.9H), 9.37 (s, 0.1H), 7.30-7.24 (m, 2H), 7.10-7.08 (m, 2H), 2.54-2.47 (m, 2H)), 2.16-2.03 (m, 2H), 1.82-1.75 (m, 2H), 1.21-1.15 (m, 1H), 0.96 (d, J=6.4 Hz, 3H).

Step 3

(R)-(4'-chloro-5-methyl-3,4,5,6-tetrahydro-[1,1'-biphenyl]-2-yl)methanol (R)-4'-chloro-5-methyl-3,4,5,6-tetrahydro-[1,1'-biphenyl]-2-carbaldehyde (0.23 g, 1.00 mmol) was dissolved in tetrahydrofuran (2 mL) and sodium borohydride (57 mg, 1.50 mmol) was added at 0° C. The mixture was stirred at room temperature for 2 hours. The reaction was quenched by adding dropwise saturated aqueous ammonium chloride (10 mL). The mixture was extracted with ethyl acetate (10 mL) and the organic phase was washed with saturated brine (10 mL), dried, filtered. The filtrate was concentrated to obtain crude (R)-(4'-chloro-5-methyl-3,4,5,6-tetrahydro-[1,1'-biphenyl]-2-yl)methanol (0.24 g, pale yellow oil) which was used directly In the next step without purification. MS m/z (ESI): 237 & 239 [M-17].

Step 4

(R)-4'-chloro-6-(chloromethyl)-3-methyl-2,3,4,5-tetrahydro-1,1'-biphenyl (R)-(4'-chloro-5-methyl-3,4,5,6-tetrahydro-[1,1'-biphenyl]-2-yl)methanol (0.24 g, 1.00 mmol) was dissolved in dichloromethane (2 mL), and thionyl chloride (0.24 g, 1.50 mmol) was added at room temperature. The resulting mixture was stirred for 1 hour. The reaction was quenched by adding saturated aqueous sodium bicarbonate (10 mL) dropwisely. The mixture was extracted with dichloromethane (10 mL). The organic phase was washed with saturated brine (10 mL), dried and filtered. The filtrate was concentrated to obtain the crude (R)-4'-chloro-6-(chloromethyl)-3-methyl-2,3,4,5-tetrahydro-1,1'-biphenyl (0.26 g, pale yellow oil), which was used directly in the next step without purification.

The synthesis of intermediates 5-7 can refer to the synthetic procedure of intermediate 4.

| Example and name | structure | $^1$H NMR |
|---|---|---|
| Intermediate 5 (S)-4'-chloro-6-(chloromethyl)-3-methyl-2,3,4,5-tetrahydro-1,1'-biphenyl | 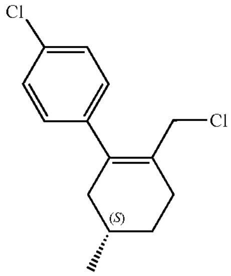 | $^1$H NMR (400 MHz, $CDCl_3$) δ 7.33-7.30 (2H), 7.17-7.14 (m, 2H), 3.90 (s, 2H), 2.41-2.26 (m, 4H), 1.87-1.78 (m, 3H), 1.01 (d, J = 6.4 Hz, 3H). |
| Intermediate 6 4'-chloro-6-(chloromethyl)-4,4-dimethyl-2,3,4,5-tetrahydro-1,1'-biphenyl | 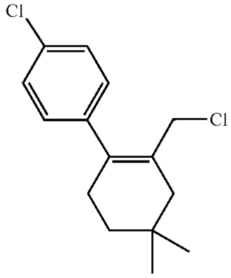 [SMILES: CC1(C)CCC(c2ccc(Cl)cc2)=C(CCl)C1] | $^1$H NMR (400 MHz, $CDCl_3$) δ 7.32 (d, J = 8.4 Hz, 2H), 7.15 (d, J = 8.4 Hz, 2H), 3.88 (s, 2H), 2.32-2.30 (m, 2H), 2.05-2.03 (m, 2H), 1.49-1.47 (m, 2H), 0.99 (s, 6H). |
| Intermediate 7 5-(chloromethyl)-6-(4-chlorophenyl)spiro[2.5]oct-5-ene | 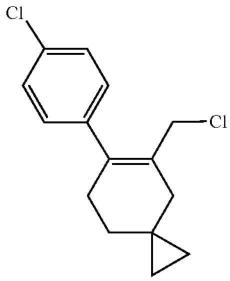 [SMILES: ClCC1=C(c2ccc(Cl)cc2)CCC2(CC2)C1] | $^1$H NMR (400 MHz, $CDCl_3$) δ 7.34-7.31 (m, 2H), 7.22-7.18 (m, 2H), 3.88 (s, 2H), 2.42-2.33 (m, 2H), 2.17-2.11 (m, 2H), 1.56-1.48 (m, 2H), 0.44-0.37 (m, 4H). |

Intermediate 8

5-(Chloromethyl)-6-(4-chlorophenyl)-8,8-dimethyl-spiro[2.5]oct-5-ene

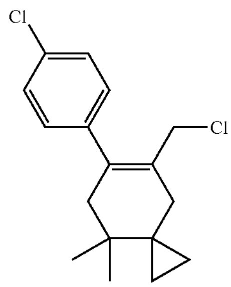 [SMILES: CC1(C)CC(c2ccc(Cl)cc2)=C(CCl)CC12CC2]

Step 1

7,7-Dimethyl-8-methylene-1,4-dioxaspiro[4.5]decane

Methyltriphenylphosphine bromide (14.00 g, 39.20 mmol) was added to anhydrous tetrahydrofuran (120 mL) and the mixture was cooled to −40° C. A solution of n-butyllithium in n-hexane (2.5 M, 39.2 mmol, 15.6 mL) was added dropwise under nitrogen protection. After the addition, the reaction mixture was warmed to room temperature and stirred for 1 hour. Then, 7,7-dimethyl-1,4-dioxaspiro[4.5]decane-8-one (6.00 g, 32.60 mmol) was added dropwise, and the reaction mixture was stirred at room temperature overnight. The reaction was quenched with saturated aqueous ammonium chloride (200 mL) and the aqueous phase was extracted with ethyl acetate (100 mL×2). The organic phases were combined and washed with saturated brine (200 mL). The organic phase was dried over anhydrous sodium sulfate, filtered and the filtrate was concentrated under reduced pressure. The residue was purified by silica gel column chromatography (0-10% ethyl acetate/petroleum ether) to give the product 7,7-dimethyl-8-methylene-1,4-dioxaspiro[4.5]decane (3.80 g, colorless oil). Yield: 64%.

$^1$H NMR (400 MHz, $CDCl_3$) δ 4.73 (s, 2H), 3.98-3.94 (m, 4H), 2.43-2.36 (m, 2H), 1.73-1.68 (m, 2H), 1.62 (s, 2H), 1.16 (s, 6H).

Step 2

4, 4-Dimethyl-7,10-dioxabispiro[2.2.$4^6$.$2^3$]dodecane 7,7-Dimethyl-8-methylene-1,4-dioxaspiro[4.5]decane (0.90 g, 4.94 mmol) was dissolved in dichloromethane (20 mL), and a solution of diethylzinc in toluene (2M, 14.80 mmol, 7.4 mL) was added dropwise under nitrogen protection at 0° C. The reaction mixture was stirred for 0.5 hours after the addition. Then chloroiodomethane (5.20 g, 29.60 mmol) was added dropwise and the reaction mixture was stirred at room temperature overnight. Saturated aqueous ammonium chloride (30 mL) was added to quench the reaction and the organic phase was separated. The aqueous phase was extracted with dichloromethane (30 mL×2), and the combined organic phase was washed with water (30 mL×2) and saturated brine (20 mL). The organic phase was dried over anhydrous sodium sulfate, filtered, and the filtrate was concentrated under reduced pressure to obtain the crude 4,4-dimethyl-7,10-dioxabispiro[2.2.$4^6$.$2^3$]dodecane (1.50 g, yellow oil).

$^1$H NMR (400 MHz, $CDCl_3$) δ 3.96-3.91 (m, 4H), 1.69-1.62 (m, 2H), 1.55 (s, 2H), 1.44-1.40 (m, 2H), 0.83 (s, 6H), 0.50-0.46 (m, 2H), 0.11-0.08 (m, 2H).

Step 3

4, 4-Dimethylspiro[2.5]octan-6-one 4,4-Dimethyl-7,10-dioxabispiro[2.2.$4^6$.$2^3$]dodecane (1.50 g, crude product from step 2, 4.94 mmol) was dissolved in a mixture of hydrochloric acid and tetrahydrofuran (2M, 14.00 mmol, 7 mL) and the mixture was stirred at room temperature for 2 hours. The reaction mixture was quenched by adding saturated aqueous sodium bicarbonate (30 mL) and extracted with ethyl acetate (30 mL). The organic phase was washed with water (30 mL×2) and saturated brine (30 mL) respectively. The organic phase was dried over anhydrous sodium sulfate, filtered, and the filtrate was concentrated under reduced pressure to give crude 4,4-dimethylspiro[2.5]octan-6-one (0.70 g, yellow oil). Yield: 93.2%. MS m/z (ESI): 153 [M+1].

Step 4

6-Chloro-8,8-dimethylspiro[2.5]oct-5-ene-5-carbaldehyde

Phosphorus oxychloride (1.10 g, 6.90 mmol) was added dropwise to a solution of N,N-dimethylformamide (0.67 g, 9.20 mmol) in dichloromethane (30 mL) in an ice bath under nitrogen protection. After the addition, the reaction mixture was stirred at room temperature for 30 minutes, cooled to 0° C. again, and a solution of 4,4-dimethylspiro[2.5]octan-6-one (0.70 g, 4.60 mmol) in dichloromethane (5 mL) was added dropwise. The reaction was carried out at room temperature overnight. Water (30 mL) was added to quench the reaction and the organic phase was separated. The organic phase was washed with saturated aqueous sodium bicarbonate (30 mL) and saturated brine (30 mL), dried over anhydrous sodium sulfate and filtered. The filtrate was concentrated under reduced pressure, and the residue was purified by silica gel column chromatography (100% petroleum ether) to obtain 6-chloro-8,8-dimethylspiro[2.5]oct-5-ene-5-carboxaldehyde (0.34 g, pale yellow oil). Yield: 37.2%. MS m/z (ESI): 199 & 201 [M+1].

Step 5

6-(4-Chlorophenyl)-8,8-dimethylspiro[2.5]oct-5-ene-5-carbaldehyde

Under nitrogen protection, 6-chloro-8,8-dimethylspiro[2.5]oct-5-ene-5-carbaldehyde (0.34 g, 1.70 mmol), p-chlorophenylboronic acid (0.41 g, 2.60 mmol), potassium carbonate (0.70 g, 5.10 mmol), tetra-n-butylammonium bromide (0.55 g, 1.70 mmol) and palladium acetate (77 mg, 0.34 mmol) were added to water (15 mL). The reaction system was evacuated and flushed with nitrogen for three times. The temperature was raised to 50° C. and kept at this temperature for 4 hours. The reaction mixture was cooled to room temperature and extracted with ethyl acetate (20 mL×2). The combined organic phase was washed with saturated brine (20 mL), dried over anhydrous sodium sulfate and filtered. The filtrate was concentrated under reduced pressure. The residue was purified by silica gel column chromatography (0-5% ethyl acetate/petroleum ether) to give 6-(4-chlorophenyl)-8,8-dimethylspiro[2.5]oct-5-ene-5-carbaldehyde (0.18 g, pale yellow oil).

Yield: 38.2%. MS m/z (ESI): 275 & 277 [M+1].

Step 6

(6-(4-Chlorophenyl)-8,8-dimethylspiro[2.5]oct-5-en-5-yl)methanol 6-(4-Chlorophenyl)-8,8-dimethylspiro[2.5]oct-5-ene-5-carbaldehyde (0.18 g, 0.66 mmol) was dissolved in the mixture of tetrahydrofuran-methanol (v/v=6/1, 7 mL), and sodium borohydride (75 mg, 1.78 mmol) was added. The mixture was stirred at room temperature for 2 hours. Saturated aqueous ammonium chloride (20 mL) was added to quench the reaction. The reaction mixture was extracted with ethyl acetate (20 mL×2), the combined organic phase was washed with saturated brine (20 mL), the organic phase was dried over anhydrous sodium sulfate, filtered, The filtrate was concentrated under reduced pressure to give (6-(4-chlorophenyl)-8,8-dimethylspiro[2.5]oct-5-en-5-yl) methanol (0.16 g, colorless oil). Yield: 88.2%. MS m/z (ESI): 260 & 262 [M-17].

Step 7

5-(Chloromethyl)-6-(4-chlorophenyl)-8,8-dimethylspiro[2.5]oct-5-ene (6-(4-Chlorophenyl)-8,8-dimethylspiro[2.5]oct-5-en-5-yl)methanol (0.16 g, 0.58 mmol) was dissolved in dichloromethane (10 mL), thionyl chloride (0.21 g, 1.74 mmol) was added to it. The reaction mixture was stirred at room temperature overnight and concentrated under reduced pressure to give crude 5-(chloromethyl)-6-(4-chlorophenyl)-8,8-dimethyl spiro[2.5]oct-5-ene (0.17 g, yellow oil).

$^1$H NMR (400 MHz, $CDCl_3$) δ 7.36-7.29 (m, 2H), 7.20-7.13 (m, 2H), 3.88 (s, 2H), 2.20-2.11 (m, 2H), 1.64-1.53 (m, 2H)), 0.85 (s, 6H), 0.63-0.57 (m, 2H), 0.24-0.16 (m, 2H).

Intermediate 9

7, 7, 8, 8-Tetramethyl-1,4-dioxaspiro[4.5]decane

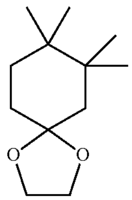

7, 7, 8, 8-Tetramethyl-1,4-dioxaspiro[4.5]decane 4,4-Dimethyl-7,10-dioxabispiro[$2.2.4^6.2^3$]dodecane (see step 2 of Intermediate 8) (4.30 g, 21.9 mmol) and platinum dioxide (1.00 g, 4.40 mmol) were added into acetic acid (30 mL). The reaction mixture was evacuated and replaced with hydrogen, then heated to 40° C. and kept overnight. Then the reaction mixture was cooled to room temperature, diluted with ethyl acetate (30 mL) and filtered through celite. The filter cake was washed with ethyl acetate (20 mL), and the filtrate was concentrated under reduced pressure to obtain the crude 7,7,8,8-tetramethyl-1,4-dioxaspiro[4.5]decane (4.50 g, colorless oil). MS m/z (ESI): 199 [M+1].

The synthesis of intermediate 10 can be referred to the synthesis of intermediate 8.

| Example and name | structure | Ms or $^1$H NMR |
|---|---|---|
| Intermediate 10 4'-chloro-6-(chloromethyl)-3,3,4,4-tetramethyl-2,3,4,5-tetrahydro-1,1'-biphenyl | 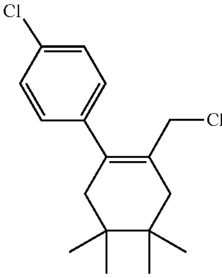 [SMILES: CC1(C)CC(CCl)=C(c2ccc(Cl)cc2)CC1(C)C] | $^1$H NMR (400 MHz, $CDCl_3$) δ 7.33-7.30 (m, 2H), 7.16-7.11 (m, 2H), 3.88 (s, 2H), 2.14-2.06 (m, 4H), 0.95 (s, 6H), 0.93 (s, 6H). |

Example 1

(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-3-methylpiperazin-1-yl)-N-((3-fluoro-5-nitro-4-(((tetrahydro-2H-pyran-4-yl)methyl)amino)phenyl)sulfonyl)benzamide

1

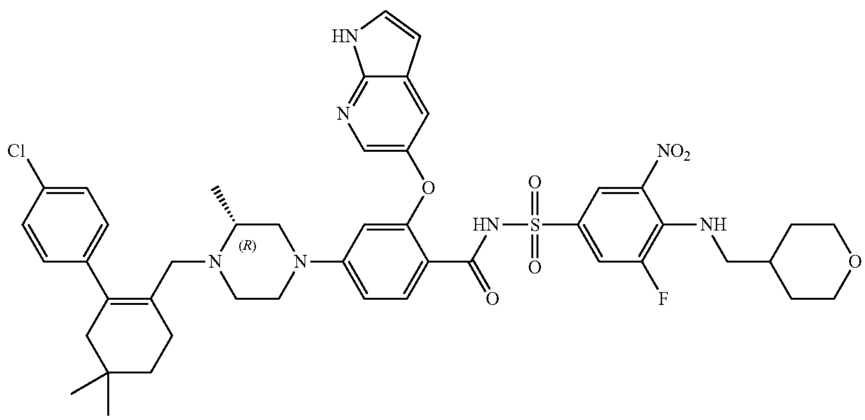

Step 1

(R)-Methyl 2-((1H-pyrrolo[2,3-b]pyridin-5-yl)oxy)-4-(3-methylpiperazin-1-yl)benzoate Methyl 2-((1H-pyrrolo[2,3-b]pyridin-5-yl)oxy)-4-fluorobenzoate (synthesis can refer to: *Journal of Organic Chemistry,* 84(8), 4814-4829; 2019) (2.86 g, 10.00 mmol), (R)-2-methylpiperazine (3.00 g, 30.00 mmol), N,N-diisopropylethylamine (3.12 g, 24.18 mmol) and dimethyl sulfoxide (20 mL) were mixed and stirred at 60° C. for 16 hours. The mixture was diluted with 50 mL of water and extracted with ethyl acetate (60 mL×2). The combined organic phase was washed with saturated brine (50 mL×3). The organic phase was dried over anhydrous sodium sulfate, filtrated to remove the desiccant, and the crude product was obtained by removing the solvent under reduced pressure. Purification by column chromatography (dichloromethane/methanol=90:10) gave the target product (R)-Methyl 2-((1H-pyrrolo[2,3-b]pyridin-5-yl)oxy)-4-(3-methylpiperazin-1-yl)benzoate (2.55 g, yellow solid). Yield: 70%, MS m/z (ESI): 367[M+1];

$^1$H NMR (400 MHz, $CDCl_3$) δ 9.92 (s, 1H), 8.19 (d, J=2.4 Hz, 1H), 7.91 (d, J=9.2 Hz, 1H), 7.52 (d, J=2.4 Hz, 1H)), 7.36-7.35 (m, 1H), 6.66-6.63 (m, 1H), 6.43 (d, J=1.6 Hz, 1H), 6.34 (d, J=2.4 Hz, 1H), 3.79 (s, 3H), 3.54-3.48 (m, 2H), 3.05-3.02 (m, 1H), 2.93-2.84 (m, 2H), 2.77-2.71 (m, 1H), 2.42-2.37 (m, 1H), 1.08 (d, J=6.4 Hz, 3H).

Step 2

(R)-Methyl 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-3-methylpiperazin-1-yl)benzoate (R)-Methyl 2-((1H-pyrrolo[2,3-b]pyridin-5-yl)oxy)-4-(3-methylpiperazin-1-yl)benzoate (34 mg, 0.09 mmol), 4'-chloro-6-(chloromethyl)-3,3-dimethyl-2,3,4,5-tetrahydro-1,1'-biphenyl (Synthesis can be referred to: US 20100298323) (30 mg, 0.11 mmol), N,N-diisopropylethylamine (36 mg, 0.28 mmol) and acetonitrile (5.0 mL) were combined, and the mixture was stirred at 60° C. for 16 hours. The mixture was quenched with 10 mL of water and extracted with ethyl acetate (10 mL×2). The combined organic phase was washed with brine (10 mL×2). The organic phase was dried over anhydrous sodium sulfate, filtrated to remove the desiccant, and the crude product was obtained by removing the solvent under reduced pressure. Purification of the crude product by preparative plate (petroleum ether/ethyl acetate=1:1) gave the target product (R)-methyl 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-3-methylpiperazin-1-yl)benzoate (28 mg, colorless oil). Yield: 50%. MS m/z (ESI): 599 & 601 [M+1].

Step 3

(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-3-methylpiperazin-1-yl)benzoic acid (R)-methyl 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-3-methylpiperazin-1-yl)benzoate (28 mg, 0.05 mmol), lithium hydroxide (20 mg, 0.83 mmol), methanol (1 mL), tetrahydrofuran (1 mL) and water (1 mL) were mixed and stirred at 60° C. for 1.5 hours. The mixture was adjusted to neutral with 1 N hydrochloric acid, and extracted with ethyl acetate (10 mL×2). The combined organic phase was washed with brine (10 mL). The organic phase was dried over anhydrous sodium sulfate, filtrated to remove the desiccant, and the crude product (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-3-methylpiperazin-1-yl)benzoic acid (25.6 mg, crude) was obtained by removing the solvent under reduced pressure. This crude product was used directly in the next reaction without purification. MS m/z (ESI): 585 & 587 [M+1].

Step 4

(R)-2-((1H-pyrrolo[2,3-b]pyridin-5-yl)oxy)-4-(4-((4'-chloro-5,5-dimethyl-3, 4,5,6-tetrahydro-[1,1'-biphenyl]-2-yl)methyl)-3-methylpiperazin-1-yl)-N-((3-fluoro-5-nitro-4-(((tetrahydro-2H-pyran-4-yl)methyl)amino)phenyl)sulfonyl)benzamide (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-3-methylpiperazin-1-yl)benzoic acid (26 mg, 0.04 mmol), 3-fluoro-5-nitro-4-(((tetrahydro-2H-pyran-4-yl)methyl)amino)benzenesulfonamide (Intermediate 1) (15 mg, 0.04 mmol), 4-dimethylaminopyridine (11 mg, 0.09 mmol), 1-(3-dimethylaminopropyl)-3-ethylcarbodiimide hydrochloride (17 mg, 0.09 mmol) and dichloromethane (2.5 mL) were combined and the mixture was stirred at room temperature for 16 hours. The mixture was quenched with 10 mL of water and extracted with dichloromethane (10 mL×2). The combined organic phase was washed with saturated brine (10 mL), dried over anhydrous sodium sulfate, filtrated, and the crude product was obtained by removing the solvent under reduced pressure. Purification of the crude product using preparative silica gel plate (dichloromethane/methanol=15:1)] gave the target product (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-3-methylpiperazin-1-yl)-N-((3-fluoro-5-nitro-4-(((tetrahydro-2H-pyran-4-yl)methyl)amino)phenyl)sulfonyl)benzamide 1 (15.7 mg, yellow solid). Yield: 38%.

MS m/z(ESI): 900&902[M+1];

$^1$H NMR (400 MHz, $CD_3OD$) δ 8.49 (s, 1H), 8.08-8.05 (m, 1H), 7.71-7.64 (m, 2H), 7.50 (s, 1H), 7.44 (d, J=3.6 Hz, 1H), 7.36-7.34 (m, 2H), 7.09-7.07 (m, 2H), 6.77 (d, J=8.0 Hz, 1H), 6.42-6.36 (m, 2H), 4.04-3.93 (m, 3H), 3.71-3.67 (m, 2H), 3.52-3.38 (m, 5H), 3.28-3.26 (m, 2H), 3.08-3.02 (m, 1H), 2.96-2.93 (m, 1H), 2.65-2.63 (m, 1H), 2.24-2.15 (m, 2H), 2.06-2.04 (m, 1H), 1.93-1.89 (m, 1H), 1.85 (d, J=4.0 Hz, 3H), 1.70-1.64 (m, 3H), 1.58-1.56 (m, 2H), 1.39-1.28 (m, 2H), 1.01 (s, 3H), 0.90 (s, 3H).

The synthetic procedures of Examples 2 to 7 can be referred to the procedure of Example 1.

| Example and name | structure | MS & $^1$H NMR |
|---|---|---|
| Example 2<br>(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-3-methylpiperazin-1-yl)-N-((3-nitro-4-(((tetrahydro-2H-pyran-4-yl)methyl)amino)phenyl)sulfonyl) benzamide | 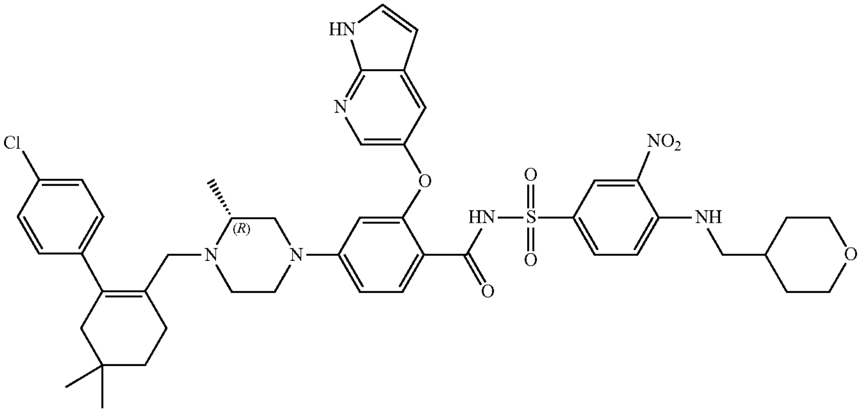 | MS m/z (ESI): 882 & 884 [M + 1];<br>$^1$H NMR (400 MHz, $CDCl_3$) δ 12.19 (s, 1H), 9.76 (s, 1H), 8.83 (d, J = 2.4 Hz, 1H), 8.54-8.51 (m, 1H), 8.14-8.08 (m, 2H), 7.97 (d, J = 8.8 Hz, 1H), 7.63-7.61 (m, 1H), 7.32 (s, 1H), 7.30 (s, 1H), 6.95-6.92 (m, 3H), 6.73-6.71 (m, 1H), 6.61 (d, J = 8.4 Hz, 1H), 6.01 (s, 1H), 4.04-3.93 (m, 3H), 3.71-3.67 (m, 3H), 3.52-3.38 (m, 5H), 3.28-3.26 (m, 3H), 2.62-2.60 (m, 1H), 2.24-2.15 (m, 2H), 2.06-2.04 (m, 1H), 1.93-1.89 (m, 1H), 1.85 (d, J = 4.0 Hz, 3H), 1.76-1.73 (m, 3H), 1.48-1.40 (m, 4H), 0.96 (s, 3H), 0.94 (s, 3H). |
| Examle 3<br>(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl) methyl)-3-methylpiperazin-1-yl)-N-((3--nitro-4(((1-(3-oxetanyl)piperidin-4-yl) methyl)amino)phenyl)sulfonyl) benzamide | 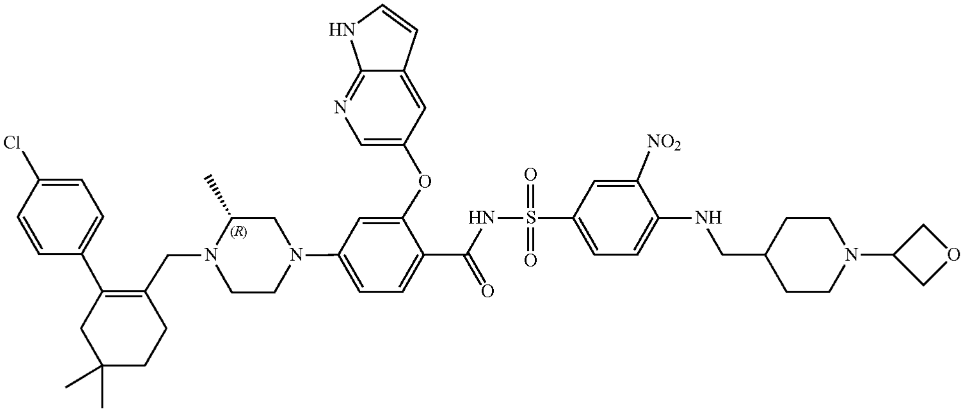 | MS m/z (ESI): 937 & 939 [M + 1];<br>$^1$H NMR (400 MHz, $CD_3OD$) δ 8.59 (d, J = 2.0 Hz, 1H), 7.93-7.91 (m, 1H), 7.82-7.79 (m, 1H), 7.56 (d, J = 8.8 Hz, 1H), 7.42 (s, 1H), 7.34 (d, J = 3.2 Hz, 1H), 7.27-7.25 (m, 2H), 7.00-6.98 (m, 2H), 6.91 (d, J = 9.6 Hz, 1H), 6.69-6.67 (m, 1H), 6.33-6.21 (m, 1H), 6.24 (s, 1H), 4.28-4.25 (m, 1H), 3.96-3.93 (m, 1H), 3.56-3.52 (m, 2H), 3.43-3.40 (m, 3H), 3.32-3.30 (m, 2H), 3.21-3.11 (m, 5H), 3.03-2.95 (m, 2H), 2.78-2.75 (m, 3H), 2.55-2.52 (m, 1H), 2.14-1.93 (m, 7H), 1.49-1.46 (m, 3H), 1.23-1.18 (m, 4H), 0.93 (s, 3H), 0.90 (s, 3H). |

-continued

| Example and name | structure | MS & $^1$H NMR |
|---|---|---|
| Example 4<br>(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-3-methylpiperazin-1-yl)-N-((3-fluoro-5-nitro-4-(((1-(3-oxetanyl)piperidin-4-yl)methyl)amino)phenyl)sulfonyl)benzamide | 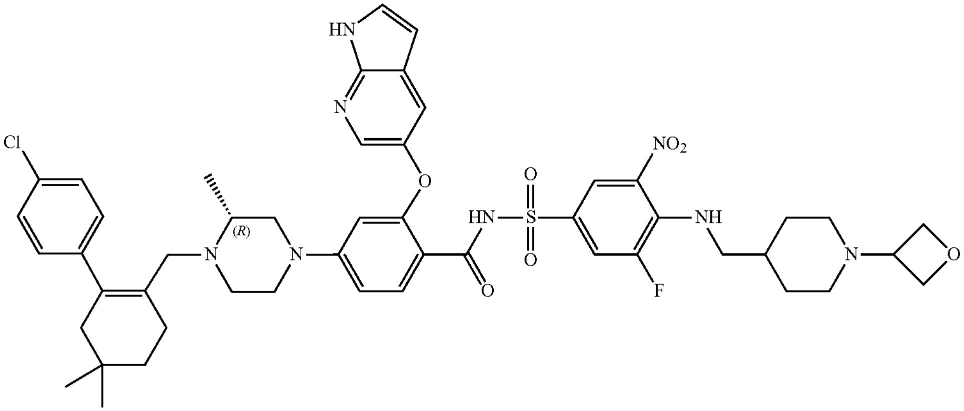 | MS m/z (ESI): 955 & 957 [M + 1]; $^1$H NMR (400 MHz, $CD_3OD$) δ 8.40 (s, 1H), 8.02-8.00 (m, 1H), 7.67-7.63 (m, 1H), 7.56 (d, J = 8.8 Hz, 1H), 7.42 (s, 1H), 7.34 (d, J = 3.2 Hz, 1H), 7.27-7.25 (m, 2H), 6.98-6.97 (m, 2H), 6.68 (d, J = 8.8 Hz, 1H), 6.34 (s, 1H), 6.26 (s, 1H), 4.28-4.25 (m, 1H), 3.96-3.93 (m, 1H), 3.49-3.40 (m, 7H), 3.21-3.11 (m, 5H), 3.03-2.97 (m, 2H), 2.78-2.75 (m, 3H), 2.53-2.52 (m, 1H), 2.15-1.93 (m, 7H), 1.42-1.38 (m, 3H), 1.23-1.18 (m, 4H), 0.92 (s, 3H), 0.90 (s, 3H). |
| Example 5<br>N-((4-((((S)-1,4-dioxan-2-yl)methyl)amino)-3-nitrophenyl)sulfonyl)-2-((1H-pyrrolo[2,3-b]pyridin-5-yl)oxy)-4-((R)-4-((4'-chloro-5,5-dimethyl-3,4,5,6-tetrahydro[1,1'-biphenyl]-2-yl)methyl)-3-methylpiperazin-1-yl)benzamide | 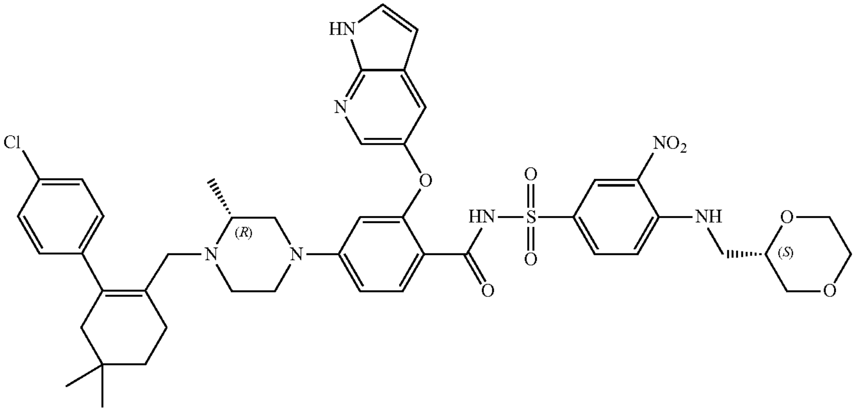 | MS m/z (ESI): 884 & 886 [M + 1]; $^1$H NMR (400 MHz, $CDCl_3$) δ 10.10 (s, 1H), 9.25 (s, 1H), 8.87 (s, 1H), 8.60 (s, 1H), 8.20-8.14 (m, 2H), 7.94 (d, J = 8.8 Hz, 1H), 7.67 (s, 1H), 7.44 (s, 1H), 7.22 (d, J = 8.0 Hz, 2H), 6.92-6.83 (m, 3H), 6.54 (s, 2H), 5.98 (s, 1H), 3.85-3.65 (m, 7H), 3.49-3.09 (m, 7H), 2.82-2.79 (m, 1H),2.64-2.48 (m, 4H), 2.29-2.15 (m, 3H), 1.97-1.94 (m, 3H), 1.41-1.37 (m, 2H), 0.92 (s, 3H), 0.91 (s, 3H). |

-continued

| Example and name | structure | MS & $^1$H NMR |
| --- | --- | --- |
| Example 6 N-((4-((((S)-1,4-dioxan-2-yl) methyl)amino)-3-fluoro-5-nitrophenyl)sulfonyl)-2-((1H-pyrrolo[2,3-b]pyridin-5-yl)oxy)-4-((R)-4-((4'-chloro-5,5-dimethyl-3,4,5,6-tetrahydro-[1,1'-biphenyl]-2-yl)methyl)-3-methylpiperazin-1-yl) benzamide | 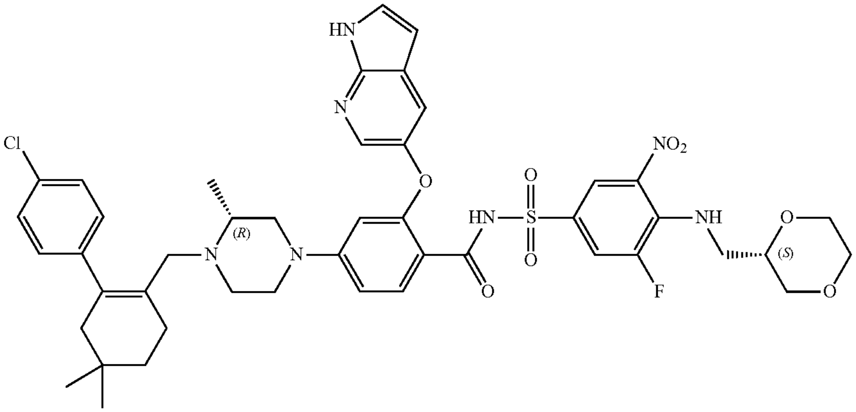 | MS m/z (ESI): 902 & 904 [M + 1]; $^1$H NMR (400 MHz, $CDCl_3$) δ 10.18 (s, 1H), 8.69 (s, 1H), 8.62-8.59 (m, 1H), 8.20 (s, 1H), 7.96-7.91 (m, 2H), 7.70 (s, 1H), 7.48-7.46 (m, 1H), 7.23 (d, J = 8.0 Hz, 2H), 6.91 (d, J = 8.0 Hz, 2H), 6.55-6.53 (m, 2H), 5.98 (s, 1H), 3.85-3.74 (m, 5H), 3.67-3.61 (m, 2H), 3.46-3.42 (m, 1H), 3.28-3.17 (m, 3H), 2.91-2.87 (m, 1H), 2.70-2.65 (m, 3H), 2.32-2.23 (m, 2H), 2.06-1.94 (m, 3H), 1.86-1.74 (m, 2H), 1.41-1.38 (m, 2H), 0.92 (s, 3H), 0.91 (s, 3H), 0.88 (d, J = 6.4 Hz, 3H). |
| Example 7 (S)-2-((1H-pyrrolo[2,3-b]pyridin-5-yl)oxy)-(4-4-((4'-chloro-5,5-dimethyl-3,4,5,6-tetrahydro-[1,1'-biphenyl]-2-yl)methyl)-3-methylpiperazin-1-yl)-N-((3-fluoro-5-nitro-4-(((tetrahydro-2H-pyran-4-yl) methyl)amino)phenyl)sulfonyl) benzamide | 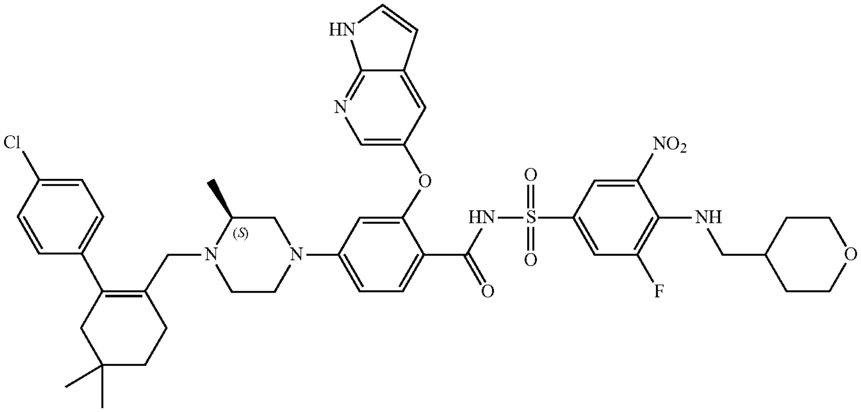 | MS m/z (ESI): 900 & 902 [M + 1]; $^1$H NMR (400 MHz, $CDCl_3$) δ 10.12 (brs, 1H), 9.33 (s, 1H), 8.76-8.67 (m, 1H), 8.53-8.45 (m, 1H), 8.26-8.17 (m, 1H), 8.03-7.91 (m, 2H), 7.73-7.69 (m, 1H), 7.48-7.45 (m, 1H), 7.25-7.19 (m, 2H), 6.95-6.88 (m, 2H), 6.58-6.50 (m, 2H), 5.97 (d, J = 2.0 Hz, 1H), 4.05-3.97 (m, 2H), 3.60-3.52 (m, 2H), 3.44-3.35 (m, 2H), 3.28-3.18 (m, 2H), 3.15-3.05 (m, 1H), 2.88-2.75 (m, 1H), 2.68-2.47 (m, 3H), 2.30-2.13 (m, 2H), 2.03-1.87 (m, 4H), 1.81-1.63 (m, 3H), 1.45-1.37 (m, 4H), 0.95 (s, 3H), 0.94 (s, 3H), 0.89 (d, J = 6.4 Hz, 3H). |

Example 8

(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)-N-((3-nitro-4-(((tetrahydro-2H-pyran-4-yl)methyl)amino)phenyl)sulfonyl)benzamide

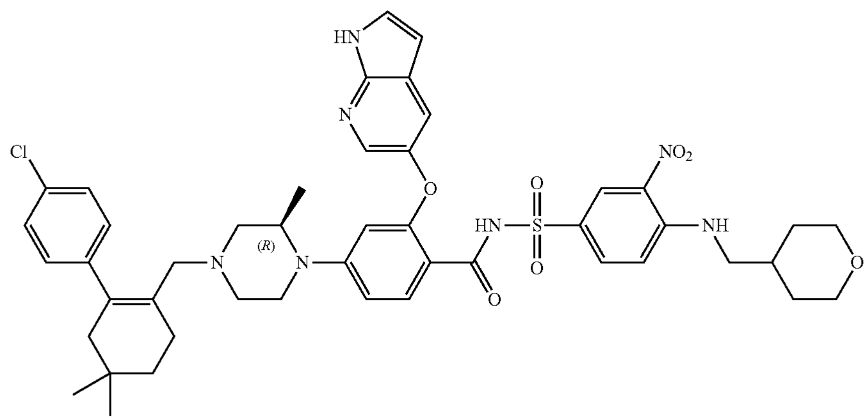

8

Step 1

(R)-tert-Butyl 4-(3-((1H-pyrrolo[2,3-b]pyridin-5-yl)oxy)-4-cyanophenyl)-3-methylpiperazine-1-carboxylate 2-((1H-Pyrrolo[2,3-b]pyridin-5-yl)oxy)-4-fluorobenzonitrile (synthesis can be referred to: WO 2017212431) (0.51 g, 2.00 mmol) and (R)-tert-butyl 3-methylpiperazine-1-carboxylate (1.20 g, 6.00 mmol) were dissolved in dimethyl sulfoxide (15 mL), potassium hydrogen phosphate (1.05 g, 6.00 mmol) was added at room temperature, and stirred at 110° C. for 36 hours. The reaction mixture was cooled to room temperature, diluted with water and extracted with ethyl acetate (30 mL×2). The combined organic phase was washed with brine (30 mL×2), dried and concentrated to obtain a crude product, which was purified by silica gel column chromatography (Petroleum ether:ethyl acetate=3:1) to give (R)-tert-butyl 4-(3-((1H-pyrrolo[2,3-b]pyridin-5-yl)oxy)-4-cyanophenyl)-3-methylpiperazine-1-carboxylate (0.35 g, white solid), Yield: 41%.

MS m/z (ESI): 434[M+1];

$^1$H NMR (400 MHz, $CDCl_3$) δ 9.29 (s, 1H), 8.19 (s, 1H), 7.69 (s, 1H), 7.49 (d, J=8.8 Hz, 1H), 7.42-7.40 (m, 1H), 6.53-6.49 (m, 2H), 6.08 (s, 1H), 40.5-3.83 (m, 3H), 3.21-3.20 (m, 2H), 3.04-2.95 (m, 2H), 1.44 (s, 9H), 1.02 (d, J=6.4 Hz, 3H).

Step 2

(R)-2-((1H-Pyrrolo[2,3-b]pyridin-5-yl)oxy)-4-(2-methylpiperazin-1-yl)benzonitrile (R)-tert-Butyl 4-(3-((1H-pyrrolo[2,3-b]pyridin-5-yl)oxy)-4-cyanophenyl)-3-methylpiperazine-1-carboxylate (0.35 g, 0.81 mmol) was dissolved in a solution of hydrochloric acid in dioxane (4 M, 20.00 mmol, 5 mL) and the mixture was stirred at room temperature for 1 hour. The reaction mixture was evaporated to give crude (R)-2-((1H-pyrrolo[2,3-b]pyridin-5-yl)oxy)-4-(2-methylpiperazin-1-yl)benzonitrile (0.38 g, crude), which was used directly in the next step without purification. MS m/z (ESI): 334 [M+1].

Step 3

(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)benzonitrile (R)-2-((1H-Pyrrolo[2,3-b]pyridin-5-yl)oxy)-4-(2-methylpiperazin-1-yl)benzonitrile (0.38 g, crude) and 4'-chloro-6-(chloromethyl)-3,3-dimethyl-2,3,4,5-tetrahydro-1,1'-biphenyl (0.21 g, 0.80 mmol) (Synthesis can be referred to: US 20100298323) was dissolved in acetonitrile (10 mL) and N,N-diisopropylethylamine (0.31 g, 2.40 mmol) was added. The mixture was stirred at 80° C. for 4 hours and cooled to room temperature, diluted with water, extracted with ethyl acetate (20 mL×2), and the combined organic phase was washed with saturated brine (20 mL). The organic phase was dried and concentrated to give a crude product, which was purified by silica gel column (petroleum ether:ethyl acetate=2:1) to give (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)benzonitrile (0.30 g, white solid), Yield: 66%.

MS m/z(ESI): 566 & 568 [M+1];

$^1$H NMR (400 MHz, $CDCl_3$) δ 9.40 (s, 1H), 8.19 (s, 1H), 7.68 (s, 1H), 7.43 (d, J=8.8 Hz, 1H), 7.42-7.40 (m, 1H), 7.23 (d, J=8.4 Hz, 2H), 6.92 (d, J=8.4 Hz, 2H), 6.52-6.45 (m, 2H), 6.04 (s, 1H), 3.81-3.78 (m, 1H), 3.16-3.13 (m, 1H), 2.98-2.95 (m, 1H), 2.69-2.65 (m, 3H), 2.54-2.51 (m, 1H), 2.21-2.14 (m, 2H), 2.04-1.97 (m, 2H), 1.89-1.76 (m, 2H), 1.43-1.40 (m, 2H), 1.07 (d, J=6.4 Hz, 3H), 0.94 (s, 3H), 0.93 (s, 3H).

Step 4

(R)-2-((1H-Pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)benzoic acid (R)-2-((1H-Pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)benzonitrile (0.11 g, 0.20 mmol) was dissolved in 2-butanol (3 mL) and sodium hydroxide (160 mg, 4.00 mmol) was added at 90° C. The mixture was heated to 105° C. and stirred for 24 hours. The reaction mixture was evaporated under reduced pressure, 1 N aqueous hydrochloric acid (4 mL) was added to the residue, extracted with ethyl acetate (10 mL×2). The combined organic phase was washed with brine (10 mL), dried and concentrated to give crude product, which was purified by preparative silica gel plate (dichloromethane:methanol=10:1) to give (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)benzoic acid (90 mg, white solid), Yield: 77%. MS m/z (ESI): 585 & 587 [M+1].

Step 5

(R)-2-((1H-Pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)-N-((3-nitro-4-(((tetrahydro-2H-pyran-4-yl)methyl)amino)phenyl)sulfonyl)benzamide The synthesis is carried out according to the last step of the procedure of Example 1, the desired product (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)-N-((3-nitro-4-(((tetrahydro-2H-pyran-4-yl)methyl) amino)phenyl) sulfonyl)benzamide 8 was obtained.

MS m/z (ESI): 882 & 884 [M+1];

1H NMR (400 MHZ, $CDCl_3$) δ 10.13 (s, 1H), 9.29 (s, 1H), 8.88 (s, 1H), 8.53-8.50 (m, 1H), δ 8.22-8.16 (m, 2H), 7.94 (d, J=8.8 Hz, 1H), 7.70 (s, 1H), 7.47-7.45 (m, 1H), 7.22 (d, J=8.0 Hz, 2H), 6.93-6.89 (m, 3H), 6.56-6.49 (m, 2H), 5.94 (s, 1H), 4.05-4.01 (m, 2H), 3.78-3.74 (m, 1H), 3.45-3.39 (m, 2H), 3.28-3.25 (m, 2H), 3.15-3.12 (m, 1H), 2.96-2.89 (m, 1H), 2.73-2.62 (m, 3H), 2.51-2.48 (m, 1H), 2.20-2.11 (m, 2H), 1.99-1.95 (m, 3H), 1.86-1.83 (m, 1H), 1.79-1.72 (m, 3H), 1.45-1.39 (m, 4H), 1.03 (d, J=6.4 Hz, 3H), 0.93 (s, 3H), 0.92 (s, 3H).

The synthetic procedures of Examples 9 to 13 can be referred to the procedure of Example 8.

| Example and name | structure | MS & $^1$H NMR |
|---|---|---|
| Example 9 (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)-N-((3-nitro-4-(((1-(3-oxetan-yl)piperidin-4-yl)methyl)amino)phenyl)sulfonyl) benzamide | 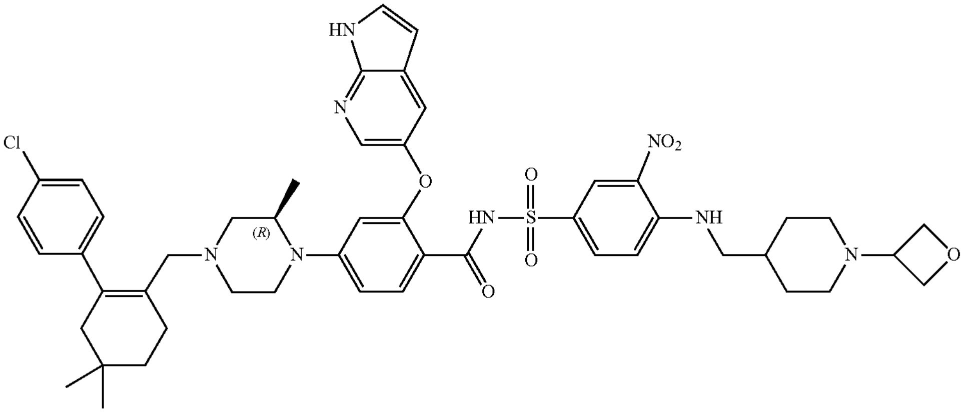 | MS m/z (ESI): 937 & 939 [M + 1]; $^1$H NMR (400 MHz, $CDCl_3$) δ 8.87 (s, 1H), 8.54-8.52 (m, 1H), 8.13-8.06 (m, 2H), 7.91 (d, J = 8.8 Hz, 1H), 7.71 (s, 1H), 7.47-7.45 (m, 1H), 7.23 (d, J = 8.0 Hz, 2H), 6.94-6.91 (m, 3H), 6.53-6.51 (m, 2H), 5.94 (s, 1H), 4.78-4.70 (m, 4H), 3.77-3.67 (m, 3H), 3.41-3.26 (m, 3H), 3.17-3.13 (m, 1H), 2.95-2.65 (m, 5H), 2.54-2.47 (m, 2H), 2.21-2.18 (m, 2H), 2.02-1.97 (m, 3H), 1.90-1.85 (m, 3H), 1.63-1.57 (m, 2H), 1.37-1.33 (m, 3H), 1.05 (d, J = 6.4 Hz, 3H), 0.93 (s, 3H), 0.92 (s, 3H). |
| Example 10 (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)-N-((3-fluoro-5-nitro-4-(((1-(3-oxetanyl) piperidin-4-yl)methyl)amino)phenyl) sulfonyl)benzamide | 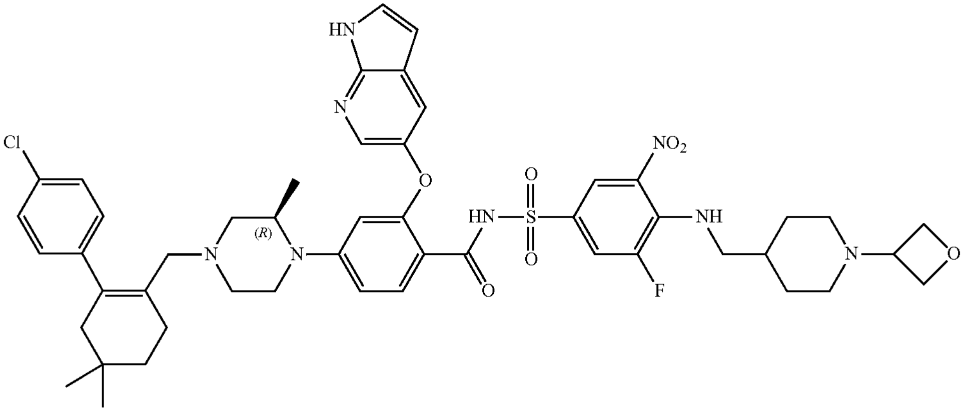 | MS m/z (ESI): 955 & 957 [M + 1]; $^1$H NMR (400 MHz, $CDCl_3$) δ 8.70 (s, 1H), 8.52-8.49 (m, 1H), 8.17 (s, 1H), 7.94-7.89 (m, 2H), 7.74 (s, 1H), 7.46-7.44 (m, 1H), 7.23 (d, J = 8.0 Hz, 2H), 9.62 (d, J = 8.0 Hz, 2H), 6.57-6.52 (m, 2H), 5.93 (s, 1H), 4.68-4.62 (m, 4H), 3.77-3.73 (m, 3H), 3.58-3.49 (m, 3H), 3.17-3.14 (m, 1H), 2.95-2.91 (m, 2H), 2.83-2.81 (m, 3H), 2.54-2.51 (m, 2H), 2.20-2.17 (m, 2H), 1.98-1.95 (m, 3H), 1.87-1.82 (m, 3H), 1.68-1.62 (m, 2H), 1.41-1.37 (m, 3H), 1.04 (d, J = 6.4 Hz, 3H), 0.93 (s, 3H), 0.92 (s, 3H). |

-continued

| Example and name | structure | MS & $^1$H NMR |
|---|---|---|
| Example 11 (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)-N-((3-fluoro-5-nitro-4-(((tetrahydro-2H-pyran-4-yl)methyl)amino)sulfonyl)benzamide | 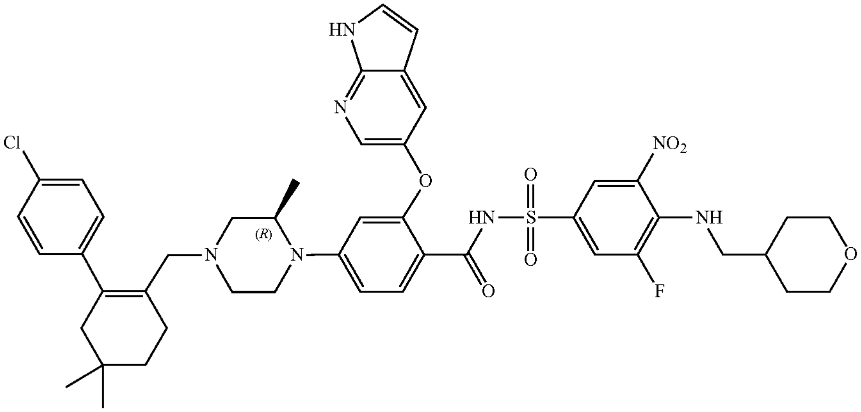 | MS m/z (ESI): 900 & 902 [M + 1]; $^1$H NMR (400 MHz, $CDCl_3$) δ 10.14 (s, 1H), 9.69 (s, 1H), 8.71 (s, 1H), 8.51-8.48 (m, 1H), 8.22 (s, 1H), 7.97-7.93 (m, 2H), 7.72 (s, 1H), 7.48-7.46 (m, 1H), 7.21 (d, J = 8.0 Hz, 2H), 6.91 (d, J = 8.0 Hz, 2H), 6.56-6.51 (m, 2H), 5.94 (s, 1H), 4.03-3.99 (m, 2H), 3.78-3.75 (m, 1H), 3.56-3.54 (m, 2H), 3.44-3.38 (m, 2H), 3.16-3.13 (m, 1H), 2.96-2.91 (m, 1H), 2.71-2.63 (m, 3H), 2.52-2.49 (m, 1H), 2.19-2.15 (m, 2H), 1.97-1.95 (m, 2H), 1.86-1.69 (m, 5H), 1.42-1.34 (m, 4H), 1.04 (d, J = 6.4 Hz, 3H), 0.92 (s, 3H), 0.91 (s, 3H). |
| Example 12 N-((4-((((S)-1,4-dioxan-2-yl)methyl)amino)-3-nitrophenyl)sulfonyl)-2-((1H-pyrrolo[2,3-b]pyridin-5-yl)oxy)-4-((R)-4-((4'-chloro-5,5-dimethyl-3,4,5,6-tetrahydro-[1,1'-biphenyl]-2-yl)methyl)-2-methylpiperazin-1-benzamide | 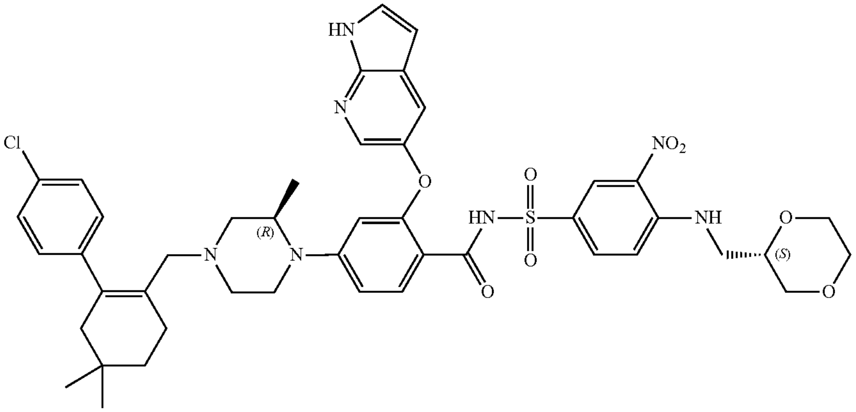 | MS m/z (ESI): 884 & 886 [M + 1]; $^1$H NMR (400 MHz, $CDCl_3$) δ 10.03 (s, 1H), 9.40 (s, 1H), 8.81 (s, 1H), 8.53 (s, 1H), 8.12-8.08 (m, 2H), 7.87 (d, J = 9.2 Hz, 1H), 7.62 (s, 1H), 7.38 (s, 1H), 7.14 (d, J = 8.4 Hz, 2H), 6.85-6.80 (m, 3H), 6.46-6.42 (m, 2H), 5.87 (s, 1H), 3.85-3.55 (m, 8H), 3.43-3.27 (m, 3H), 3.08-3.05 (m, 1H), 2.87-2.82 (m, 1H), 2.68-2.55 (m, 3H), 2.42-2.40 (m, 1H), 2.17-2.13 (m, 3H), 1.79-1.68 (m, 4H), 0.96 (d, J = 6.4 Hz, 3H), 0.86 (s, 3H), 0.84 (s, 3H). |

-continued
| Example and name | structure | MS & $^1$H NMR |
| --- | --- | --- |
| Example 13 (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)-2-methylpiperazin-1-yl)-N-((3-nitro-4-(((tetrahydro-2H-pyran-4-yl)methyl)amino)phenyl)sulfonyl)benzamide | 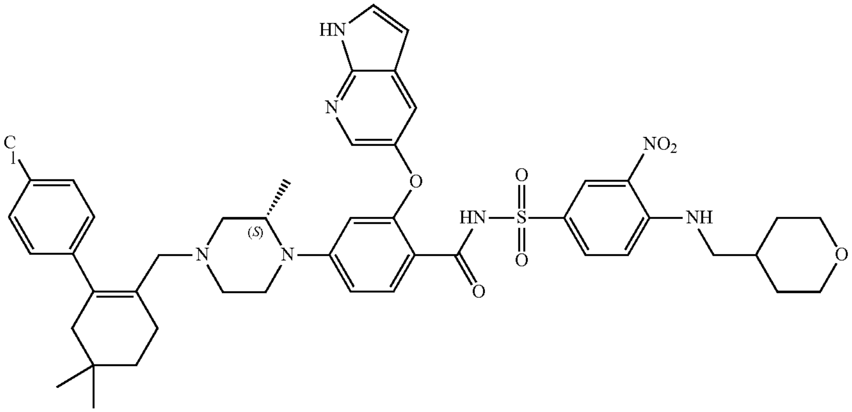 | MS m/z (ESI): 882 & 884 [M + 1]; $^1$H NMR (400 MHz, $CDCl_3$) δ 10.09 (brs, 1H), 8.93-8.88 (d, J = 4.0 Hz, 1H), 8.52 (t, J = 4.0 Hz, 1H), 8.23-8.12 (m, 2H), 8.03-7.96 (m, 1H), 7.73-7.69 (m, 1H), 7.48-7.45 (m, 1H), 7.38-7.30 (m, 3H), 6.95-6.90 (m, 2H), 6.62-6.50 (m, 2H), 5.98 (d, J = 2.0 Hz, 1H), 4.07-3.98 (m, 2H), 3.92-3.69 (m, 4H), 3.47-3.37 (m, 3H), 3.32-3.22 (m, 3H), 2.88-2.70 (m, 3H), 2.66-2.46 (m, 3H), 2.31-2.26 (m, 1H), 1.82-1.70 (m, 2H), 1.46-1.36 (m, 5H), 0.96 (s, 3H), 0.94 (s, 3H), 0.84 (d, J = 6.0 Hz, 3H). |

The synthetic procedures of Examples 14 to 22 can be referred to the procedure of Example 1.

| Example and name | structure | MS & $^1$H NMR |
| --- | --- | --- |
| Example 14 2-((1H-pyrrolo[2,3-b]pyridin-5-yl)oxy)-4-((R)-4-(((S)-4'-chloro-5-methyl-3,4,5,6-tetrahydro-[1,1'-biphenyl]-2-yl)methyl-3-methylpiperazin-1-yl)-N-((3-fluoro-5-nitro-4-(((tetrahydro-2H-pyran-4-yl)methyl)amino)phenyl) sulfonyl)benzamide | 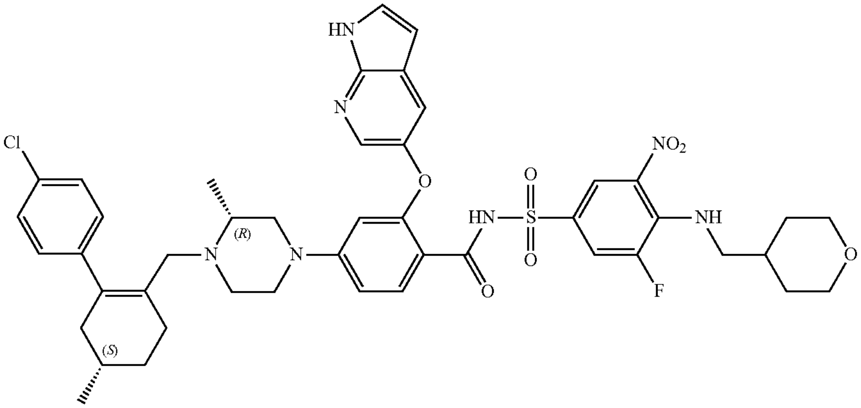 | MS m/z (ESI): 886 & 888 [M + 1]; $^1$H NMR (400 MHz, $CDCl_3$) δ 12.15 (s, 1H), 9.85~9.77 (bs, 1H), 8.66 (s, 1H), 8.56-8.49 (m, 1H), 8.13-8.05 (m, 2H), 7.98 (d, , J = 8.8 Hz, 1H), 7.90 (dd, , J = 13.2 & 2.0 Hz, 1H), 7.62 (d, , J = 2.0 Hz, 1H), 7.31 (d, , J = 8.0 Hz, 2H), 6.96 (d, , J = 8.0 Hz, 2H), 6.76-6.68 (m, 1H), 6.60 (d, , J = 8.0 Hz, 1H), 5.98 (s, 1H), 4.04-3.93 (m, 3H), 3.62-3.54 (m, 4H), 3.52-3.36 (m, 4H), 3.32-3.18 (m, 2H), 2.42-2.13 (m, 5H), 1.96-1.75 (m, 4H), 1.71 (d, J = 12.8 Hz, 3H), 1.47-1.33 (m, 5H), 0.97 (d, J = 6.4 Hz, 3H). |
| Example 15 2-((1H-pyrrolo[2,3-b]pyridin-5-yl)oxy)-4-((R)-4-(((S)-4'-chloro-5-methyl-3,4,5,6-tetrahydro-[1,1'-biphenyl]-2-yl)methyl)-3-methylpiperazin-1-yl)-N-((3-nitro-4-(((tetrahydro-2H-pyran-4-yl)methyl)amino)-phenyl)sulfonyl)benzamide | 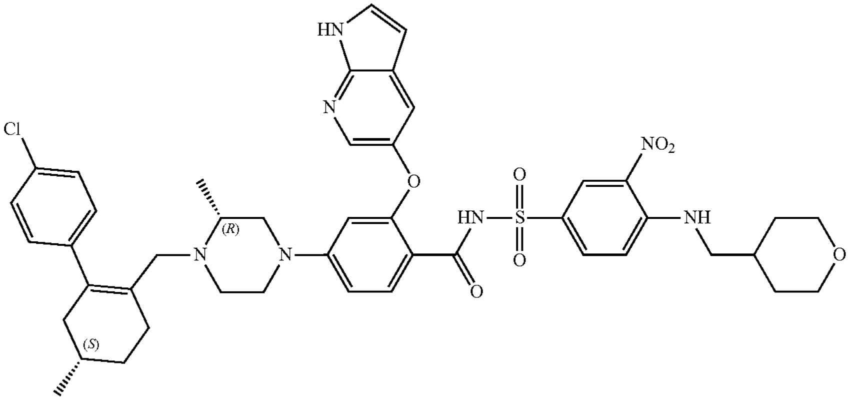 | MS m/z (ESI): 868 & 870 [M + 1]; $^1$H NMR (400 MHz, $CDCl_3$) δ 12.19 (s, 1H), 9.82-9.65 (brs, 1H), 8.81 (d, J = 2.0 Hz, 1H), 8.59-8.51 (m, 1H), 8.21-8.03 (m, 3H), 7.95 (d, J = 9.2 Hz, 1H), 7.61 (d, J = 2.0 Hz, 1H), 7.31 (d, J = 8.0 Hz, 2H), 6.96 (d, J = 8.0 Hz, 2H), 6.92 (d, J = 9.2 Hz, 1H), 6.76-6.67 (m, 1H), 6.60 (d, J = 8.4 Hz, 1H), 5.99 (s, 1H), 4.24-3.95 (m, 3H), 3.56-3.37 (m, 7H), 3.32-3.20 (m, 4H), 2.43-2.28 (m, 4H), 2.05-1.78 (m, 4H), 1.75-1.72 (m, 3H), 1.51-1.35 (m, 5H), 0.97 (d, J = 6.4 Hz, 3H). |

-continued

| Example and name | structure | MS & $^1$H NMR |
| --- | --- | --- |
| Example 16 N-((4-((((S)-1,4-dioxan-2-yl)methyl) amino)-3-nitrophenyl)sulfonyl)-2-((1H-pyrrolo[2,3-b]pyridin-5-yl)oxy)-4-((R)-4-(((S)-4'-chloro-5-methyl-3,4,5,6-tetrahydro-[1,1'-biphenyl]-2-yl)methyl)-3-methylpiperazin-1-yl) benzamide | 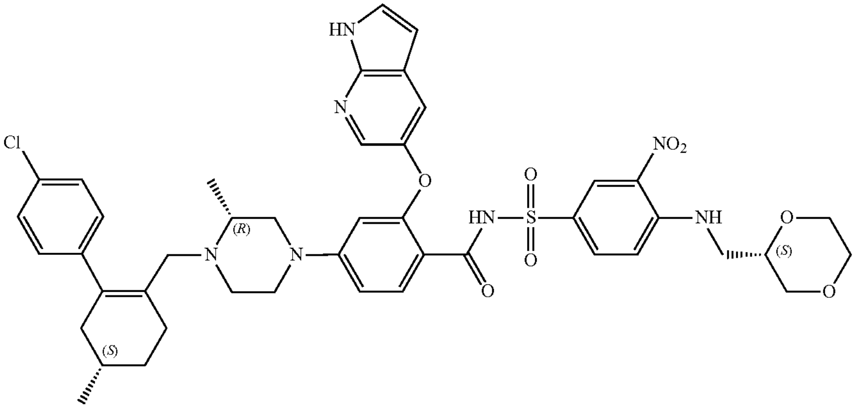 | MS m/z (ESI): 870 & 872 [M + 1]; $^1$H NMR (400 MHz, $CDCl_3$) δ 9.6 (brs, 1H), 8.93-8.82 (m, 1H), 8.66-8.54 (m, 1H), 8.26-8.10 (m, 2H), 7.94 (d, J = 8.0 Hz, 1H), 7.73-7.65 (m, 1H), 7.48-7.45 (m, 1H), 7.23-7.19 (m, 2H), 6.95-6.85 (m, 4H), 6.48-6.50 (m, 2H), 5.98 (d, J = 2.0 Hz, 1H), 3.98-3.72 (m, 5H), 3.69-3.63 (m, 1H), 3.52-3.47 (m, 1H), 3.44-3.32 (m, 2H), 3.28-3.18 (m, 2H), 3.14-3.06 (m, 1H), 2.82-2.73 (m, 1H), 2.71-2.64 (m, 1H), 2.61-2.53 (m, 1H), 2.50-2.43 (m, 1H), 2.28-1.97 (m, 6H), 1.30-1.19 (m, 3H), 0.95 (d, J = 6.4 Hz, 3H), 0.88 (d, J = 6.4 Hz, 3H). |
| Example 17 N-((4-((((S)-1,4-dioxan-2-yl)methyl) amino)-3-fluoro-5-nitrophenyl) sulfonyl)-2-((1H-pyrrolo[2,3-b]pyridin-5-yl)oxy)-4-((R)-4-(((S)-4'-chloro-5-methyl-3,4,5,6-tetrahydro-[1,1'-biphenyl]-2-yl)methyl)-3-methylpiperazin-1-yl)benzamide | 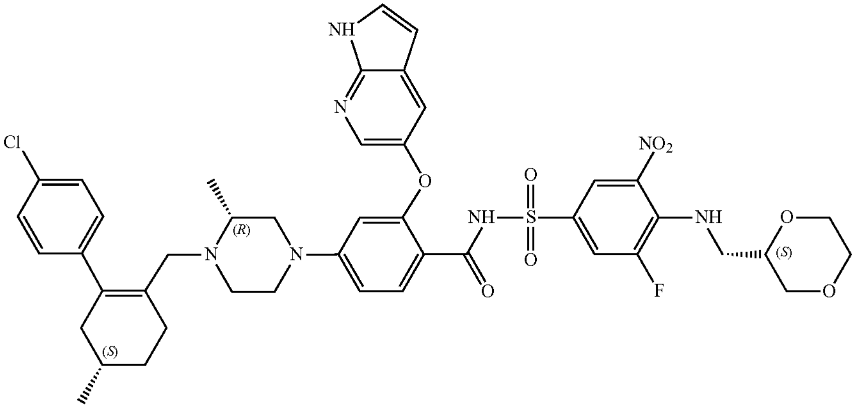 | MS m/z (ESI): 888 & 890 [M + 1]; $^1$H NMR (400 MHz, $CDCl_3$) δ 10.14 (s, 1H), 9.82 (s, 1H), 8.73-8.65 (m, 1H), 8.64-8.57 (m, 1H), 8.25-8.18 (m, 1H), 7.98-7.89 (m, 2H), 7.73-7.66 (m, 1H), 7.50-7.44 (m, 1H), 7.25-7.19 (m, 2H), 6.96-6.88 (m, 2H), 6.58-6.50 (m, 2H), 5.97 (d, J = 2.0 Hz, 1H), 3.91-3.72 (m, 6H), 3.68-3.56 (m, 2H), 3.48-3.40 (m, 1H), 3.30-3.19 (m, 2H), 3.15-3.06 (m, 1H), 2.84-2.74 (m, 1H), 2.72-2.64 (m, 1H), 2.61-2.54 (m, 1H), 2.50-2.43 (m, 1H), 2.28-2.20 (m, 4H), 1.86-1.61 (m, 2H), 1.30-1.19 (m, 3H), 0.95 (d, J = 6.0 Hz, 3H), 0.88 (d, J = 6.0 Hz, 3H). |

-continued

| Example and name | structure | MS & $^1$H NMR |
|---|---|---|
| Example 18<br>2-((1H-Pyrrolo[2,3-b]pyridin-5-yl)oxy)-4-((R)-4-(((S)-4'-chloro-5-methyl-3,4,5,6-tetrahydro-[1,1'-biphenyl]-2-yl)methyl)-2-methylpiperazn-1-yl)-N-((3-nitro-4-((((S)-4-(3-oxetanyl)morpholin-2-yl)methyl)amino)phenyl)sulfonyl)benzamide | 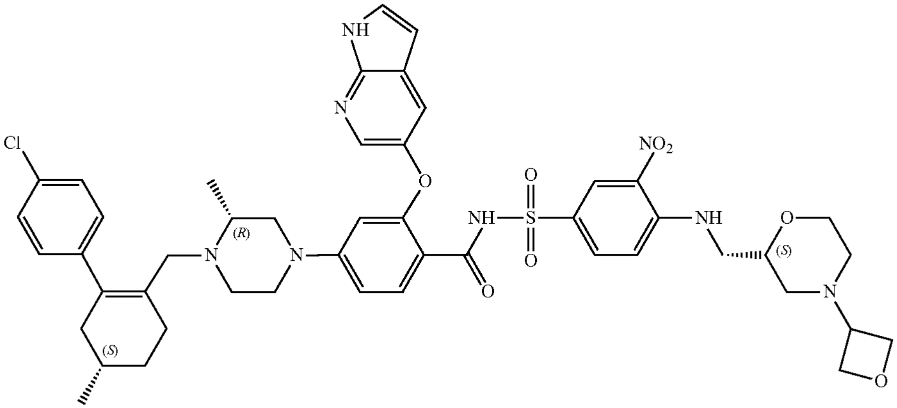 | MS m/z (ESI): 925 & 927 [M + 1];<br>$^1$H NMR (400 MHz, $CDCl_3$) δ 9.56-9.48 (m, 1H), 8.87 (d, J = 4.0 Hz, 1H), 8.64 (t, J = 4.0 Hz, 1H), 8.20-8.08 (m, 2H), 7.93 (d, J = 8.0 Hz, 1H), 7.69 (d, J = 4.0 Hz, 1H), 7.48-7.42 (m, 1H), 7.25-7.20 (m, 2H), 6.96-6.84 (m, 3H), 6.57-6.48 (m, 2H), 5.97 (d, J = 2.0 Hz, 1H), 4.79-4.58 (m, 6H), 4.01-3.86 (m, 2H), 3.81-3.71 (m, 1H), 3.56-3.35 (m, 3H), 3.28-3.18 (m, 2H), 3.15-3.06 (m, 1H), 2.82-2.43 (m, 6H), 2.27-2.01 (m, 5H), 1.99-1.92 (m, 1H), 1.28-1.21 (m, 3H), 0.95 (d, J = 6.0 Hz, 3H), 0.88 (d, J = 6.0 Hz, 3H). |
| Example 19<br>2-((1H-pyrrolo[2,3-b]pyridin-5-yl)oxy)-4-((R)-4-(((R)-4'-chloro-5-methyl-3,4,5,6-tetrahydro-[1,1'-biphenyl]-2-yl)methyl)-3-methylpiperazin-1-yl)-N-((3-nitro-4-(((tetrahydro-2H-pyran-4-yl)methyl)amino)phenyl)sulfonyl)benzamide | 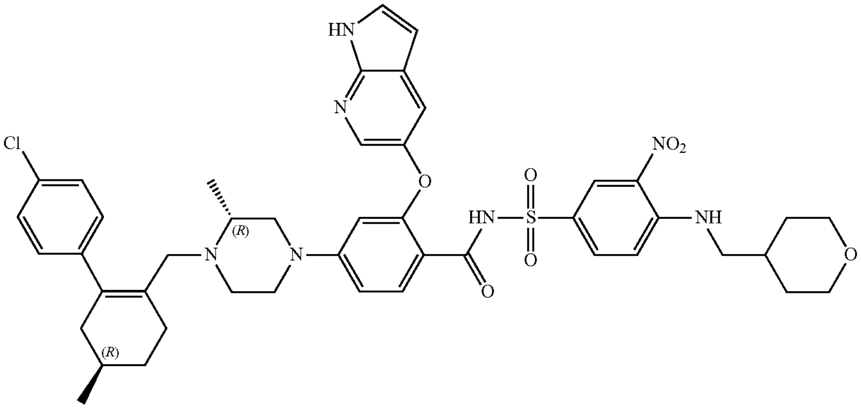 | MS m/z (ESI): 868 & 870 [M + 1];<br>$^1$H NMR (400 MHz, $CDCl_3$) δ 12.32 (s, 1H), 9.80 (s, 1H), 8.79 (s, 1H), 8.53-8.52 (m, 1H), 8.10 (d, J = 7.6 Hz, 2H), 7.91 (d, J = 8.8 Hz, 1H), 7.61 (s, 1H), 7.29 (d, J = 8.0 Hz, 2H), 7.00-6.90 (m, 2H), 6.73 (s, 1H), 6.60 (s, 1H), 6.01 (s, 1H), 4.05-4.02 (m, 2H), 3.98-3.93 (m, 1H), 3.74-3.68 (m, 1H), 3.46-3.23 (m, 8H), 2.99-2.91 (m, 1H), 2.35-2.21 (m, 4H), 2.01-1.98 (m, 3H), 1.79-7.72 (m, 4H), 1.49-1.38 (m, 3H), 1.27-1.20 (m, 3H), 0.96 (d, J = 6.4 Hz, 3H). |

-continued

| Example and name | structure | MS & $^1$H NMR |
| --- | --- | --- |
| Example 20<br>N-((4-((((S)-1,4-dioxan-2-yl)methyl)amino)-3-nitrophenyl)sulfonyl)-2-((1H-pyrrolo[2,3-b]pyridin-5-yl)oxy)-4-((R)-4-(((R)-4'-chloro-5-methyl-3,4,5,6-tetrahydro-[1,1'-biphenyl]-2-yl)methyl)-3-methylpiperazin-1-yl)benzamide | 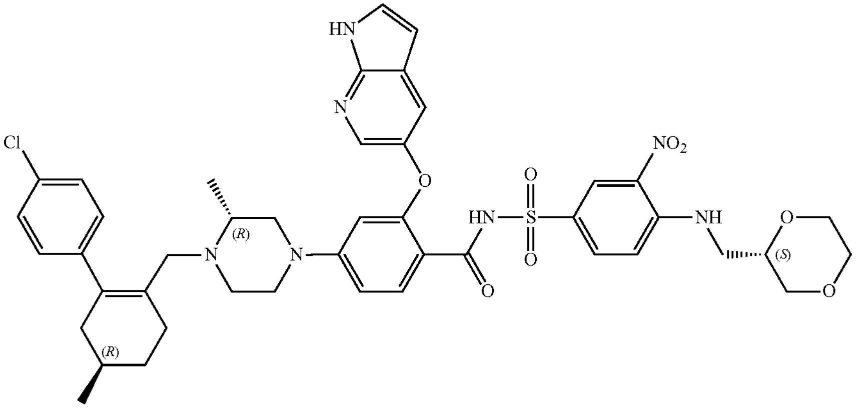 | MS m/z (ESI): 870 & 872 [M + 1]; $^1$H NMR (400 MHz, $CDCl_3$) δ 10.09 (s, 1H), 9.47 (s, 1H), 8.88 (d, J = 2.2 Hz, 1H), 8.62-8.59 (m, 1H), 8.20-8.14 (m, 2H), 7.94 (d, J = 8.8 Hz, 1H), 7.69 (d, J = 2.4 Hz, 1H), 7.46-7.45 (m, 1H), 7.23 (d, J = 8.4 Hz, 2H), 6.94-6.87 (m, 3H), 6.55-6.51 (m, 2H), 5.97 (d, J = 2.0 Hz, 1H), 3.91-3.62 (m, 7H), 3.44-3.34 (m, 3H), 3.22-3.19 (m, 2H), 3.11-3.09 (m, 1H), 2.81-2.76 (m, 1H), 2.60-2.49 (m, 4H), 2.39-2.36 (m, 1H), 2.29-2.15 (m, 2H), 1.81-1.73 (m, 4H), 0.95 (d, J = 6.4 Hz, 3H), 0.87 (d, J = 5.6 Hz, 3H). |
| Example 21<br>2-((1H-pyrrolo[2,3-b]pyridin-5-yl)oxy)-4-((R)-4-(((R)-4'-chloro-5-methyl-3,4,5,6-tetrahydro-[1,1'-biphenyl]-2-yl)methyl)-3-methylpiperazin-1-yl)-N-((3-fluoro-5-nitro-4-(((tetrahydro-2H-pyran-4-yl)methyl)amino)phenyl)sulfonyl)benzamide | 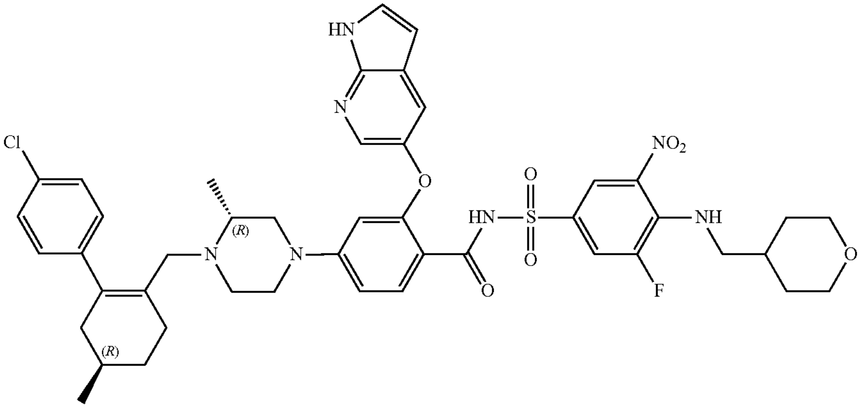 | MS m/z (ESI): 886 & 888 [M + 1]; $^1$H NMR (400 MHz, $CDCl_3$) δ 10.19 (s, 1H), 8.71 (s, 1H), 8.50-8.48 (m, 1H), 8.25 (s, 1H), 7.97-7.92 (m, 2H), 7.72 (s, 1H), 7.49-7.47 (m, 1H), 7.22 (d, J = 8.0 Hz, 2H), 6.93 (d, J = 8.0 Hz, 2H), 6.56-6.53 (m, 2H), 5.97 (s, 1H), 4.03-4.00 (m, 2H), 3.56-3.53 (m, 2H), 3.44-3.38 (m, 2H), 3.26-3.20 (m, 2H), 3.12-3.09 (m, 1H), 2.84-2.79 (m, 1H), 2.63-2.51 (m, 3H), 2.40-2.35 (m, 1H), 2.19-2.15 (m, 2H), 2.05-1.97 (m, 1H), 1.88-1.80 (m, 3H), 1.76-1.69 (m, 5H), 1.44-1.34 (m, 2H), 0.94 (d, J = 6.4 Hz, 3H), 0.88 (d, J = 6.0 Hz, 3H). |

-continued
| Example and name | structure | MS & $^1$H NMR |
|---|---|---|
| Example 22<br>N-((4-((((S)-1,4-dioxan-2-yl)methyl)amino)-3-fluoro-5-nitrophenyl)sulfonyl)-2-((1H-pyrrolo[2,3-b]pyridin-5-yl)oxy)-4-((R)-4-(((R)-4'-chloro-5-methyl-3,4,5,6-tetrahydro-[1,1'-biphenyl]-2-yl)methyl)-3-methylpiperazin-1-benzamide | 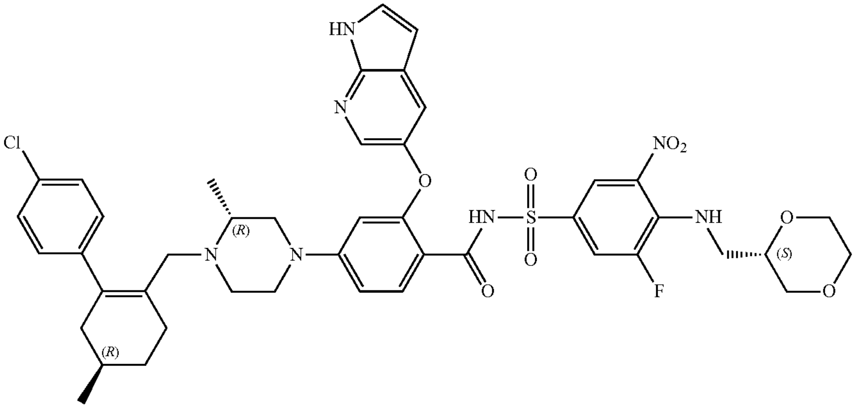 | MS m/z (ESI): 888 & 890 [M + 1];<br>$^1$H NMR (400 MHz, $CDCl_3$) δ 10.09 (s, 1H), 8.69-8.61 (m, 2H), 8.20 (s, 1H), 7.96-7.91 (m, 2H), 7.71 (s, 1H), 7.48-7.46 (m, 1H), 7.23 (d, J = 8.0 Hz, 2H), 6.93 (d, J = 8.0 Hz, 2H), 6.55-6.53 (m, 2H), 5.97 (s, 1H), 3.86-3.74 (m, 5H), 3.67-3.61 (m, 2H), 3.46-3.41 (m, 1H), 3.27-3.23 (m, 2H), 2.86-2.82 (m, 1H), 2.66-2.61 (m, 3H), 2.40-2.36 (m, 1H), 2.21-2.16 (m, 2H), 2.05-2.00 (m, 1H), 1.88-1.84 (m, 2H), 1.76-1.68 (m, 3H), 1.45-1.41 (m, 2H), 1.04 (d, J = 6.4 Hz, 3H), 0.95 (d, J = 6.0 Hz, 3H). |

The synthetic procedures of Examples 23 to 26 can be referred to the procedure of Example 8.

| Example and name | structure | MS & $^1$H NMR |
| --- | --- | --- |
| Example 23 2-((1H-pyrrolo[2,3-b]pyridin-5-yl)oxy)-4-((R)-4-(((R)-4'-chloro-5-methyl-3,4,5,6-tetrahydro-[1,1'-biphenyl]-2-yl)methyl)-2-methylpiperazin-1-yl)-N-((3-nitro-4-(((tetrahydro-2H-pyran-4-yl)methyl)amino)phenyl)sulfonyl)benzamide | 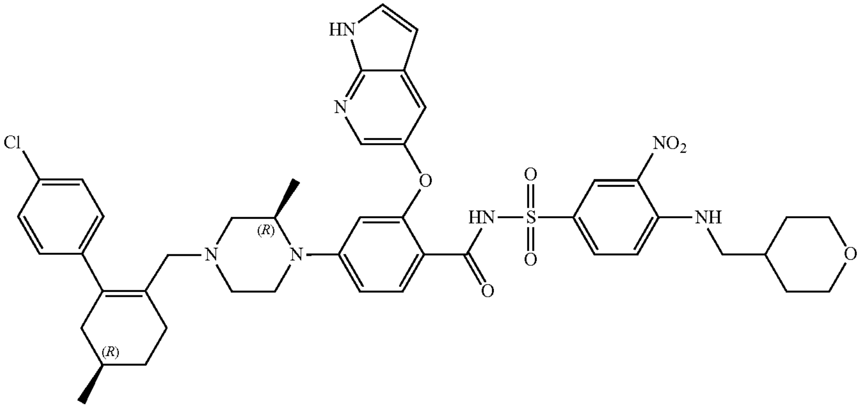 | MS m/z (ESI): 868 & 870 [M + 1]; $^1$H NMR (400 MHz, $CDCl_3$) δ 10.07 (s, 1H), 9.77 (s, 1H), 8.82 (s, 1H), 8.46-8.43 (m, 1H), 8.15-8.08 (m, 2H), 7.87 (d, J = 8.8 Hz, 1H), 7.64 (s, 1H), 7.42-7.40 (m, 1H), 7.14 (d, J = 8.0 Hz, 2H), 6.86-6.82 (m, 3H), 6.48-6.42 (m, 2H), 5.86 (s, 1H), 3.97-3.18 (m, 2H), 3.08-3.05 (m, 1H), 2.87-2.82 (m, 1H), 2.64-2.57 (m, 3H), 2.42-2.39 (m, 1H), 2.25-2.11 (m, 2H), 2.07-1.98 (m, 1H), 1.94-1.87 (m, 1H), 1.81-1.78 (m, 2H), 1.68-1.65 (m, 6H), 1.41-1.30 (m, 2H), 0.96 (d, J = 6.4 Hz, 3H), 0.88 (d, J = 6.0 Hz, 3H). |
| Example 24 N-((4-((((S)-1,4-dioxan-2-yl)methyl)amino)-3-nitrophenyl)sulfonyl)-2-((1H-pyrrolo[2,3-b]pyridin-5-yl)oxy)-4-((R)-4-((R)-4'-chloro-5-methyl-2,3,4,5,6-tetrahydro-[1,1'-biphenyl]-2-yl)methyl)-2-methylpiperazin-1-yl)benzamide | 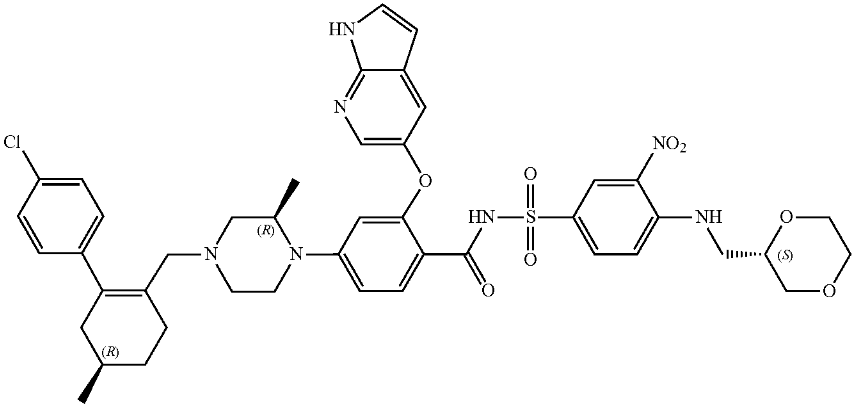 | MS m/z (ESI): 870 & 872 [M + 1]; $^1$H NMR (400 MHz, $CDCl_3$) δ 10.12 (s, 1H), 9.59 (s, 1H), 8.88 (s, 1H), 8.62-8.59 (m, 1H), 8.21-8.15 (m, 2H), 7.94 (d, J = 8.8 Hz, 1H), 7.70 (s, 1H), 7.46-7.44 (m, 1H), 7.22 (d, J = 8.0 Hz, 2H), 6.94-6.88 (m, 3H), 6.54-6.49 (m, 2H), 5.94 (s, 1H), 3.89-3.75 (m, 5H), 3.69-3.62 (m, 1H), 3.50-3.31 (m, 3H), 3.15-3.12 (m, 1H), 2.94-2.89 (m, 1H), 2.72-2.64 (m, 3H), 2.49-2.46 (m, 1H), 2.32-2.18 (m, 2H), 2.09-2.01 (m, 1H), 1.88-1.82 (m, 2H), 1.76-1.61 (m, 3H), 1.45-1.41 (m, 2H), 1.03 (d, J = 6.4 Hz, 3H), 0.95 (d, J = 6.0 Hz, 3H). |

-continued

| Example and name | structure | MS & $^1$H NMR |
| --- | --- | --- |
| Example 25 2-((1H-pyrrolo[2,3-b]pyridin-5-yl)oxy)-4-((R)-(((R)-4'-chloro-5-methyl-3,4,5,6-tetrahydro-[1,1'-biphenyl]-2-yl)methyl)-2-methylpiperazin-1-yl)-N-((3-fluoro-5-nitro-4-(((tetrahydro-2H-pyran-4-yl)methyl)amino)phenyl)sulfonyl)benzamide | 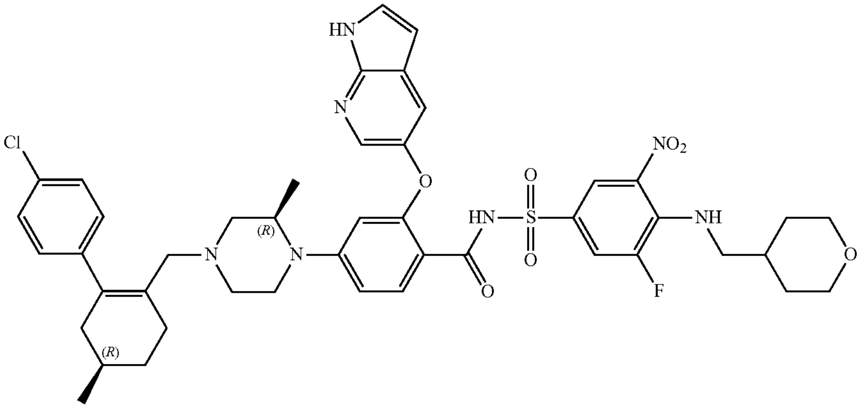 | MS m/z (ESI): 886 & 888 [M + 1]; $^1$H NMR (400 MHz, $CDCl_3$) δ 10.08 (s, 1H), 8.71 (s, 1H), 8.50-8.48 (m, 1H), 8.22 (s, 1H), 7.97-7.93 (m, 2H), 7.71 (s, 1H), 7.49-7.47 (m, 1H), 7.21 (d, J = 8.0 Hz, 2H0, 6.93 (d, J = 8.0 Hz, 2H), 6.55-6.51 (m, 2H), 5.93 (s, 1H), 4.03-4.00 (m, 2H), 3.79-3.75 (m, 1H), 3.58-3.55 (m, 2H), 3.44-3.38 (m, 2H), 3.15-3.13 (m, 1H), 2.95-2.92 (m, 1H), 2.72-2.64 (m, 3H), 2.49-2.47 (m, 1H), 2.32-2.18 (m, 2H), 2.11-2.04 (m, 2H), 1.88-1.82 (m, 3H), 1.77-1.69 (m, 5H), 1.43-1.37 (m, 2H), 1.04 (d, J = 6.4 Hz, 3H), 0.95 (d, J = 6.0 Hz, 3H). |
| Example 26 N-((4-((((S)-1,4-dioxan-2-yl)methyl)amino)-3-fluoro-5-nitrophenyl)sulfonyl)-2-((1H-pyrrolo[2,3-b]pyridin-5-yl)oxy)-4-((R)-4-(((R)-4'-chloro-5-methyl-3,4,5,6-tetrahydro-[1,1'-biphenyl]-2-methyl)-2-methylpiperazin-1-yl)benzamide | 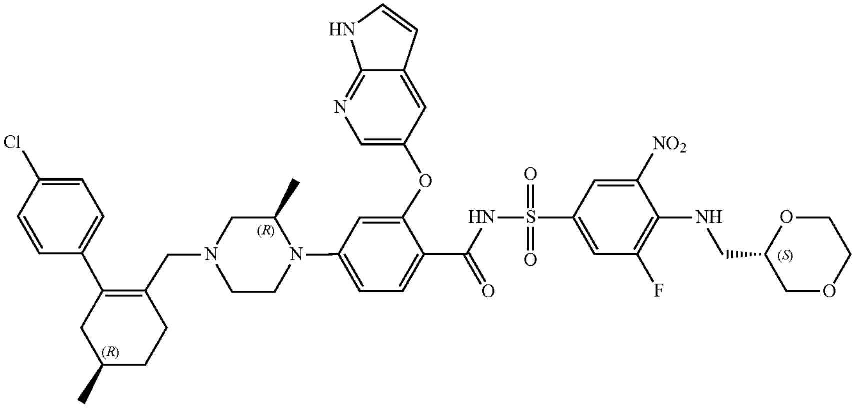 | MS m/z (ESI): 888 & 890 [M + 1]; $^1$H NMR (400 MHz, $CDCl_3$) δ 9.93 (s, 1H), 8.70 (s, 1H), 8.61-8.59 (m, 1H), 8.21 (s, 1H), 7.96-7.93 (m, 2H), 7.71 (s, 1H), 7.48-7.46 (m, 1H), 7.22 (d, J = 8.0 Hz, 2H), 6.93 (d, J = 8.0 Hz, 2H), 6.54-6.51 (m, 2H), 5.94 (s, 1H), 3.88-3.74 (m, 6H), 3.64-3.58 (m, 2H), 3.46-3.41 (m, 1H), 3.15-3.13 (m, 1H), 2.95-2.92 (m, 1H), 2.72-2.64 (m, 3H), 2.50-2.47 (m, 1H), 2.32-2.18 (m, 2H), 2.12-2.09 (m, 1H), 1.88-1.82 (m, 2H), 1.76-1.68 (m, 3H), 1.45-1.41 (m, 2H), 1.04 (d, J = 6.4 Hz, 3H), 0.95 (d, J = 6.0 Hz, 3H). |

The synthetic procedures of Examples 27 to 30 can be referred to the procedure of Example 1.

| Example and name | structure | MS & $^1$H NMR |
|---|---|---|
| Example 27 (R)-2-((1H-pyrrolo[2,3-b]pyridin-5-yl)oxy)-4-(4-((4'-chloro-4,4-dimethyl-3,4,5,6-tetrahydro-[1,1'-biphenyl]-2-yl)methyl)-3-methylpiperazin-1-yl)-N-((3-nitro-4--(((tetrahydro-2H-pyran-4-yl)methyl)amino)-phenyl)sulfonyl)benzamide | 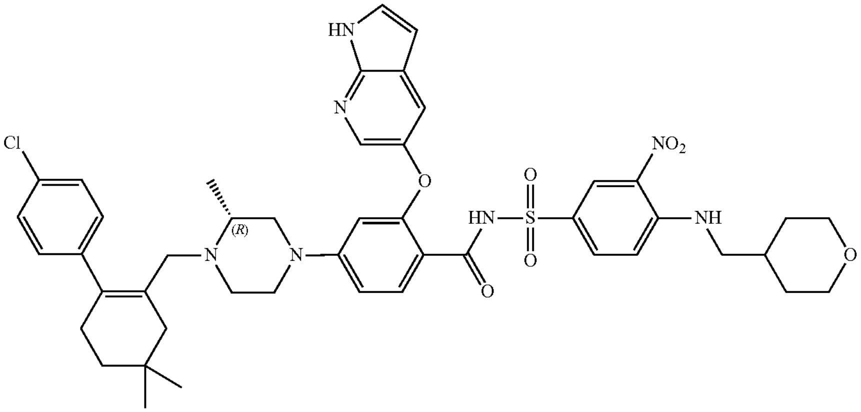 | MS m/z (ESI): 882 & 884 [M + 1]; $^1$H NMR (400 MHz, $CDCl_3$) δ 9.90 (s, 1H), 8.80 (s, 1H), 8.53-8.50 (m, 1H), 8.22-8.14 (m, 2H), 7.94 (d, J = 8.8 Hz, 1H), 7.70 (s, 1H), 7.48-7.46 (m, 1H), 7.23 (d, J = 8.0 Hz, 2H), 6.93-6.89 (m, 3H), 6.55-6.52 (m, 2H), 5.97 (s, 1H), 4.05-4.01 (m, 2H), 3.45-3.39 (m, 2H), 3.26-3.20 (m, 4H), 3.09-3.06 (m, 1H), 2.83-2.78 (m, 1H), 2.69-2.59 (m, 2H), 2.52-2.49 (m, 1H), 2.24-2.14 (m, 3H), 2.05-1.96 (m, 2H), 1.80-1.73 (m, 4H), 1.45-1.39 (m, 4H), 0.93 (s, 3H), 0.92 (s, 3H), 0.88 (d, J = 6.4 Hz, 3H). |
| Example 28 (R)-2-((1H-pyrrolo[2,3-b]pyridin-5-yl)oxy)-4-(4-((4'-chloro-4,4-dimethyl-3,4,5,6-tetrahydro-[1,1'-biphenyl]-2-yl)methyl)-3-methylpiperazin-1-yl)-N-((3-fluoro-5-nitro-4--(((tetrahydro-2H-pyran-4-yl)methyl)amino)phenyl)sulfonyl)benzamide | 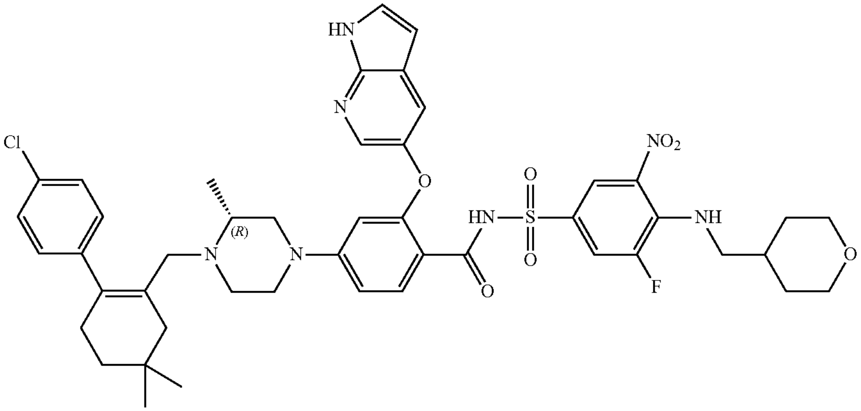 | MS m/z (ESI): 900 & 902 [M + 1]; $^1$H NMR (400 MHz, $CDCl_3$) δ 9.76 (s, 1H), 8.71 (s, 1H), 8.51-8.49 (m, 1H), 8.22 (s, 1H), 7.96-7.92 (m, 2H), 7.71 (s, 1H), 7.48-7.46 (m, 1H), 7.22 (d, J = 8.0 Hz, 2H), 6.92 (d, J = 8.0 Hz, 2H), 6.55-6.52 (m, 2H), 5.97 (s, 1H), 4.03-4.00 (m, 2H), 3.57-3.54 (m, 2H), 3.44-3.38 (m, 2H), 3.25-3.18 (m, 2H), 3.07-3.04 (m, 1H), 2.83-2.78 (m, 1H), 2.68-2.61 (m, 2H), 2.50-2.47 (m, 1H), 2.21-2.14 (m, 3H), 2.06-1.88 (m, 2H), 1.79-1.69 (m, 4H), 1.43-1.34 (m, 4H), 0.93 (s, 3H), 0.92 (s, 3H), 0.89 (d, J = 6.4 Hz, 3H). |

-continued

| Example and name | structure | MS & $^1$H NMR |
| --- | --- | --- |
| Example 29 N-((4-((((S)-1,4-dioxan-2-yl) methyl)amino)-3-nitrophenyl) sulfonyl)-2-((1H-pyrrolo[2,3-b] pyridin-5-yl)oxy)-4-((R)-4-((4'-chloro-4,4-dimethyl-3,4,5,6-tetrahydro-[1,1'-biphenyl]-2-yl) methyl)-3-methylpiperazin-1-yl) benzamide | 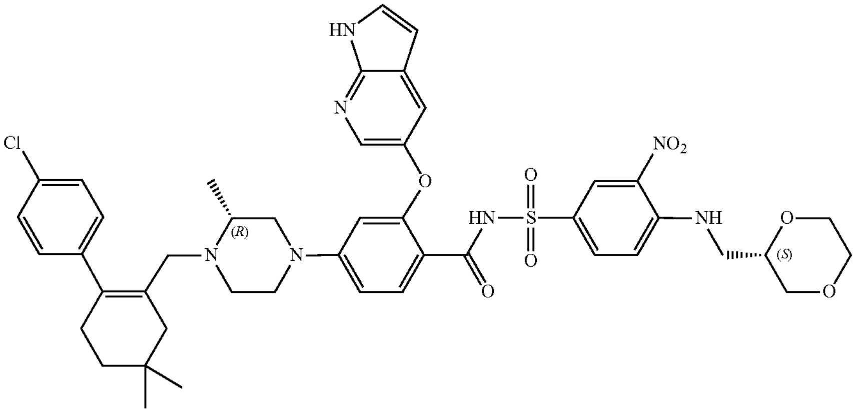 | MS m/z (ESI): 884 & 886 [M + 1]; $^1$H NMR (400 MHz, $CDCl_3$) δ 10.32 (s, 1H), 8.87 (s, 1H), 8.62-8.59 (m, 1H), 8.17-8.12 (m, 2H), 7.93 (d, J = 8.8 Hz, 1H), 7.71 (s, 1H), 7.48-7.46 (m, 1H), 7.23 (d, J = 8.0 Hz, 2H), 6.93 (d, J = 8.0 Hz, 2H), 6.87 (d, J = 8.8 Hz, 1H), 6.54-6.52 (m, 2H), 5.97 (s, 1H), 3.91-3.75 (m, 5H), 3.69-3.65 (m, 1H), 3.50-3.30 (m, 2H), 3.26-3.21 (m, 2H), 3.10-3.07 (m, 1H), 2.84-2.77 (m, 1H), 2.69-2.62 (m, 2H), 2.53-2.49 (m, 1H), 2.23-2.18 (m, 3H), 2.07-2.01 (m, 2H), 1.80-1.76 (m, 2H), 1.42-1.39 (m, 2H), 0.93 (s, 3H), 0.92 (s, 3H), 0.89 (d, J = 6.4 Hz, 3H). |
| Example 30 N-((4-((((S)-1,4-dioxan-2-yl) methyl)amino)-3-fluoro-5-nitrophenyl)sulfonyl)-2-((1H-pyrrolo[2,3-b]pyridin-5-yl)oxy)-4-((R)-4-((4'-chloro-4,4-dimethyl-3,4,5,6-tetrahydro-[1,1'-biphenyl]-2-yl)methyl)-3-methylpiperazin-1-yl)benzamide | 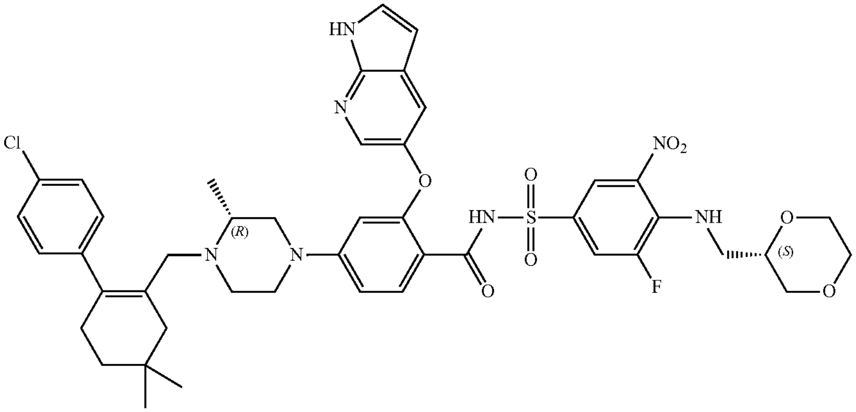 | MS m/z (ESI): 902 & 904 [M + 1]; $^1$H NMR (400 MHz, $CDCl_3$) δ 9.74 (s, 1H), 8.69 (s, 1H), 8.62-8.59 (m, 1H), 8.21 (s, 1H), 7.96-7.92 (m, 2H), 7.70 (s, 1H), 7.48-7.46 (m, 1H), 7.23 (d, J = 8.0 Hz, 2H), 6.93 (d, J = 8.0 Hz, 2H), 6.55-6.53 (m, 2H), 5.97 (s, 1H), 3.88-3.74 (m, 5H), 3.66-3.61 (m, 2H), 3.46-3.42 (m, 1H), 3.26-3.21 (m, 2H), 3.08-3.05 (m, 1H), 2.82-2.78 (m, 1H), 2.68-2.61 (m, 2H), 2.50-2.47 (m, 1H), 2.21-2.15 (m, 4H), 2.06-2.01 (m, 1H), 1.79-1.75 (m, 2H), 1.42-1.39 (m, 2H), 0.93 (s, 3H), 0.92 (s, 3H), 0.88 (d, J = 6.4 Hz, 3H). |

Example 31

(R)-2-((1H-Pyrrolo[2,3-b]pyridin-5-yl)oxy)-4-(4-((6-(4-chlorophenyl)-8,8-dimethylspiro[2.5]oct-5-en-5-yl)methyl)-3-methylpiperazin-1-yl)-N-((3-nitro-4-(((tetrahydro-2H-pyran-4-yl)methyl)amino)phenyl)sulfonyl)benzamide

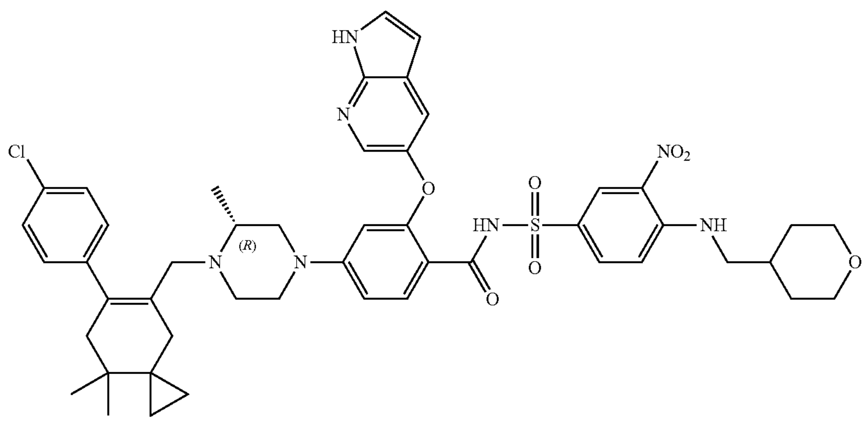

31

Step 1

(R)-Methyl 2-((1H-pyrrolo[2,3-b]pyridin-5-yl)oxy)-4-(4-((6-(4-chlorophenyl)-8,8-dimethylspiro[2.5]oct-5-en-5-yl)methyl)-3-methylpiperazin-1-yl)benzoate 5-(chloromethyl)-6-(4-chlorophenyl)-8,8-dimethylspiro[2.5]oct-5-ene (Intermediate 8) (0.17 g, 0.58 mmol), (R)-methyl 2-((1H-pyrrolo[2,3-b]pyridin-5-yl)oxy)-4-(3-methylpiperazin-1-yl)benzoate and N,N-diisopropylethylamine (0.37 g, 2.90 mmol) were dissolved in acetonitrile (15 mL) and heated to reflux for 3 hours. After cooling, it was concentrated under reduced pressure. The residue was dissolved in ethyl acetate (30 mL), washed with water (30 mL×3) and brine (30 mL) respectively. The organic phase was dried over anhydrous sodium sulfate, filtered, and the filtrate was concentrated under reduced pressure. The residue was purified by silica gel column chromatography (10%-40% ethyl acetate/petroleum ether) to give (R)-methyl 2-((1H-pyrrolo[2,3-b]pyridin-5-yl)oxy)-4-(4-((6-(4-chlorophenyl)-8,8-dimethylspiro[2.5]oct-5-en-5-yl)methyl)-3-methylpiperazin-1-yl)benzoate (0.10 g, white solid). Yield: 27.7%. MS m/z (ESI): 625 & 627 [M+1].

Step 2

(R)-2-((1H-Pyrrolo[2,3-b]pyridin-5-yl)oxy)-4-(4-((6-(4-chlorophenyl)-8,8-dimethylspiro[2.5]oct-5-en-5-yl)methyl)-3-methylpiperazin-1-yl)benzoic acid (R)-Methyl 2-((1H-pyrrolo[2,3-b]pyridin-5-yl)oxy)-4-(4-((6-(4-chlorophenyl)-8,8-dimethylspiro[2.5]oct-5-en-5-yl)methyl)-3-methylpiperazin-1-yl)benzoate (0.10 g, 0.16 mmol) was dissolved in ethanol (3 mL) and aqueous sodium hydroxide (2N, 6.00 mmol, 3 mL). The mixture was heated to 70° C. and stirred for 2 hours. After cooling, water (20 mL) was added to dilute the reaction mixture, and 1N diluted hydrochloric acid was added to adjust the pH to about 5. The aqueous phase was extracted with ethyl acetate (20 mL×2). The combined organic phase was washed with brine (20 mL). The organic phase was dried over anhydrous sodium sulfate, filtered, and the filtrate was concentrated under reduced pressure to give (R)-2-((1H-pyrrolo[2,3-b]pyridin-5-yl)oxy)-4-(4-((6-(4-chlorophenyl)-8,8-dimethylspiro[2.5]oct-5-en-5-yl)methyl)-3-methylpiperazin-1-yl)benzoic acid (80 mg, white solid). Yield: 81.8%. MS m/z (ESI): 611 & 613 [M+1].

Step 3

(R)-2-((1H-Pyrrolo[2,3-b]pyridin-5-yl)oxy)-4-(4-((6-(4-chlorophenyl)-8,8-dimethylspiro[2.5]oct-5-en-5-yl)methyl)-3-methylpiperazin-1-yl)-N-((3-nitro-4-((((tetrahydro-2H-pyran-4-yl)methyl)amino)phenyl)sulfonyl)benzamide (R)-2-((1H-Pyrrolo[2,3-b]pyridin-5-yl)oxy)-4-(4-((6-(4-chlorophenyl)-8,8-dimethylspiro[2.5]oct-5-en-5-yl)methyl)-3-methylpiperazin-1-yl)benzoic acid (20 mg, 0.03 mmol), 3-nitro-4-(((tetrahydro-2H-pyran-4-yl)methyl)amino)benzenemethanesulfonamide (Synthesis can be referred to: WO 2018041248A1) (10 mg, 0.03 mmol), 1-ethyl-(3-dimethylamino) propyl)carbodiimide hydrochloride (31 mg, 0.17 mmol) and 4-dimethylaminopyridine (8 mg, 0.07 mmol) were dissolved in dichloromethane (5 mL) and the mixture was stirred at room temperature overnight. Dichloromethane (20 mL) was added and the reaction mixture was washed with water (20 mL×3) and brine (20 mL) respectively. The organic phase was dried over anhydrous sodium sulfate, filtered, and the filtrate was concentrated under reduced pressure. The residue was purified by preparative thin layer chromatography (dichloromethane/methanol=15/1) to give the target product (R)-2-((1H-pyrrolo[2,3-b]pyridin-5-yl)oxy)-4-(4-((6-(4-chlorophenyl)-8,8-dimethylspiro[2.5]oct-5-en-5-yl)methyl)-3-methylpiperazin-1-yl)-N-((3-nitro-4-(((tetrahydro-2H-pyran-4-yl)methyl)amino)phenyl)sulfonyl)benzamide 31 (16.6 mg, yellow solid), yield: 55.7%

MS m/z(ESI): 908 & 910 [M+1];

$^{1}$H NMR (400 MHz, $CDCl_3$) δ 10.14 (brs, 1H), 9.70 (s, 1H), 8.96-8.82 (m, 1H), 8.57-8.48 (m, 1H), 8.27-8.09 (m, 2H), 8.00-7.90 (m, 1H), 7.75-7.63 (m, 1H), 7.50-7.43 (m, 1H), 7.25-7.19 (m, 2H), 7.01-6.85 (m, 3H), 6.59-6.49 (m, 2H), 5.98 (d, J=2.0 Hz, 1H), 4.10-3.95 (m, 2H), 3.48-3.38 (m, 2H), 3.32-3.17 (m, 4H), 3.12-3.03 (m, 1H)), 2.87-2.73 (m, 1H), 2.70-2.45 (m, 3H), 2.18-2.04 (m, 3H), 2.03-1.83 (m, 3H), 1.50-1.19 (m, 6H), 0.93-0.78 (m, 8H), 0.60-0.48 (m, 2H), 0.15-0.02 (m, 2H).

The synthetic procedures of Examples 32 to 34 can be referred to the procedure of Example 31.

| Example and name | structure | MS & $^1$H NMR |
|---|---|---|
| Example 32 N-((4-((((S)-1,4-dioxan-2-yl) methyl)amino)-3-fluoro-5-nitrophenyl)-sulfonyl)-2-((1H-pyrrolo [2,3-b]pyridin-5-yl)oxy)-4-((R)-4-((6-(4-chlorophenyl)-8,8-dimethylspiro[2.5]oct-5-en-5-yl) methyl)-3-methylpiperazin-1-yl) benzamide | 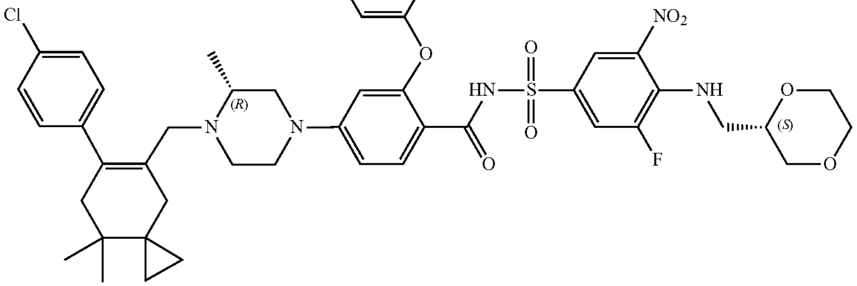 | MS m/z (ESI): 928 & 930 [M + 1]; $^1$H NMR (400 MHz, $CDCl_3$) δ 10.11 (brs, 1H), 9.36 (s, 1H), 8.73-8.58 (m, 2H), 8.25-8.17 (m, 1H), 8.00-7.90 (m, 2H), 7.75-7.63 (m, 1H), 7.50-7.43 (m, 1H), 7.25-7.19 (m, 2H), 7.01-6.92 (m, 2H), 6.59-6.51 (m, 2H), 5.98 (d, J = 2.0 Hz, 1H), 3.90-3.72 (m, 6H), 3.67-3.57 (m, 2H), 3.51-3.40 (m, 2H), 3.28-3.20 (m, 2H), 3.13-3.04 (m, 1H), 2.85-2.75 (m, 1H), 2.67-2.45 (m, 3H), 2.16-2.04 (m, 3H), 1.90-1.75 (m, 2H), 1.32-1.20 (m, 3H), 0.90-0.78 (m, 6H), 0.58-0.49 (m, 2H), 0.13-0.05 (m, 2H). |
| Example 33 (R)-2-((1H-pyrrolo[2,3-b]pyridin-5-yl)oxy)-4-(4-((6-(4-chlorophenyl)-8,8-dimethylspiro[2.5]oct-5-en-5-yl) methyl)-3-methylpiperazin-1-yl)-N-((3-fluoro-5-nitro-4--((((tetrahydro-2H-pyran-4-yl)methyl)amino)phenyl) sulfonyl)benzamide | 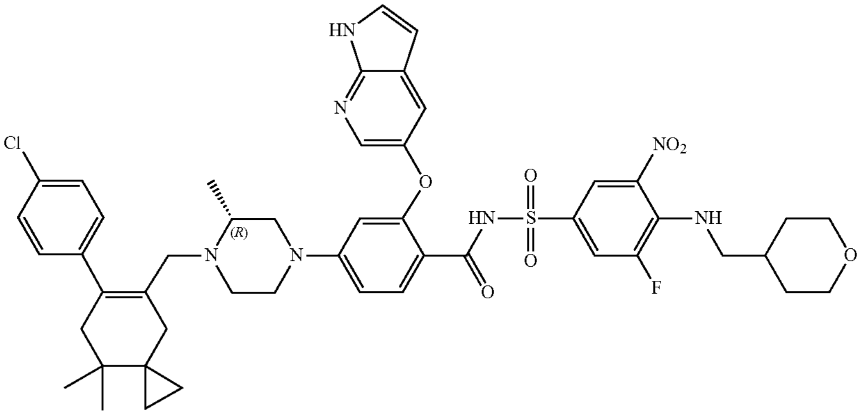 | MS m/z (ESI): 926 & 928 [M + 1]; $^1$H NMR (400 MHz, $CDCl_3$) δ 10.14 (brs, 1H), 9.59 (s, 1H), 8.74-8.67 (s, 1H), 8.53-8.43 (m, 1H), 8.22 (d, J = 4.0 Hz, 1H), 8.00-7.87 (m, 2H), 7.73-7.67 (m, 1H), 7.54-7.42 (m, 1H), 7.25-7.19 (m, 2H), 7.00-6.90 (m, 2H), 6.60-6.48 (m, 2H), 5.97 (d, J = 2.0 Hz, 1H), 4.06-3.95 (m, 2H), 3.60-3.51 (m, 2H), 3.45-3.36 (m, 2H), 3.28-3.17 (m, 2H), 3.12-3.03 (m, 1H), 2.84-2.74 (m, 1H), 2.69-2.44 (m, 3H), 2.19-2.04 (m, 3H), 1.96-1.76 (m, 3H), 1.47-1.12 (m, 6H), 0.93-0.79 (m, 8H), 0.60-0.47 (m, 2H), 0.17-0.04 (m, 2H). |

-continued
| Example and name | structure | MS & $^1$H NMR |
|---|---|---|
| Example 34 N-((4-((((S)-1,4-dioxan-2-yl)methyl) amino)-3-nitrophenyl)sulfonyl)-2-((1H-pyrrolo[2,3-b]pyridin-5-yl)oxy)-4-((R)-4-((6-(4-chlorophenyl)-8,8-dimethylspiro[2.5]oct-5-en-5-yl) methyl)-3-methylpiperazin-1-yl) benzamide | 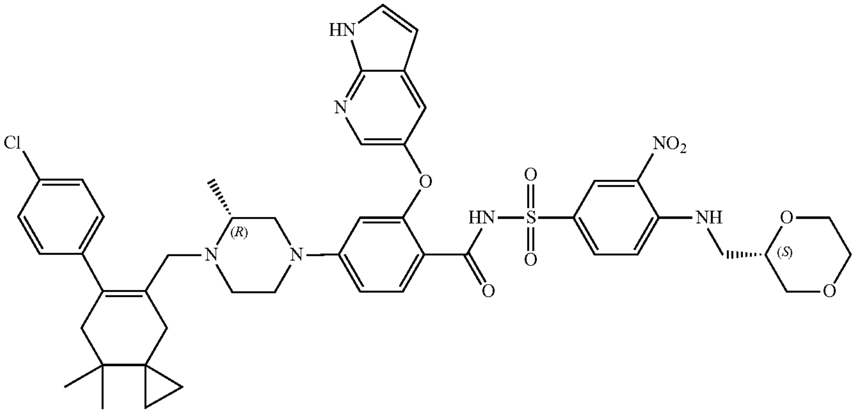 | MS m/z (ESI): 910 & 912 [M + 1]; $^1$H NMR (400 MHz, $CDCl_3$) δ 10.12 (s, 1H), 9.71 (s, 1H), 8.90-8.84 (m, 1H), 8.65-8.53 (m, 1H), 8.26-8.09 (m, 2H), 7.97-7.98 (m, 1H), 7.72-7.65 (m, 1H), 7.50-7.44 (m, 1H), 7.24-7.19 (m, 2H), 6.99-6.92 (m, 2H), 6.88 (d, J = 8.0 Hz, 1H), 6.57-6.48 (m, 2H), 5.98 (d, J = 2.0 Hz, 1H), 3.96-3.73 (m, 5H), 3.69-3.61 (m, 1H), 3.50-3.30 (m, 4H), 3.28-3.19 (m, 2H), 3.13-3.02 (m, 1H), 2.84-2.74 (m, 1H), 2.69-2.44 (m, 3H), 2.17-2.03 (m, 3H), 1.94-1.75 (m, 2H), 1.36-1.18 (m, 3H), 0.88-0.80 (m, 6H), 0.58-0.50 (m, 2H), 0.16-0.04 (m, 2H). |

The synthetic procedures of Examples 35 to 38 can be referred to the procedure of Example 1.

| Example and name | structure | MS & $^1$H NMR |
| --- | --- | --- |
| Example 35 N-((4-((((S)-1,4-dioxan-2-yl) methyl)amino)-3-fluoro-5-nitrophenyl)sulfonyl)-2-((1H-pyrrolo[2,3-b]pyridin-5-yl)oxy)-4-((R)-4-((6-(4-chlorophenyl) spiro[2.5]oct-5-en-5-yl) methyl)-3-methylpiperazin-1-yl)benzamide | 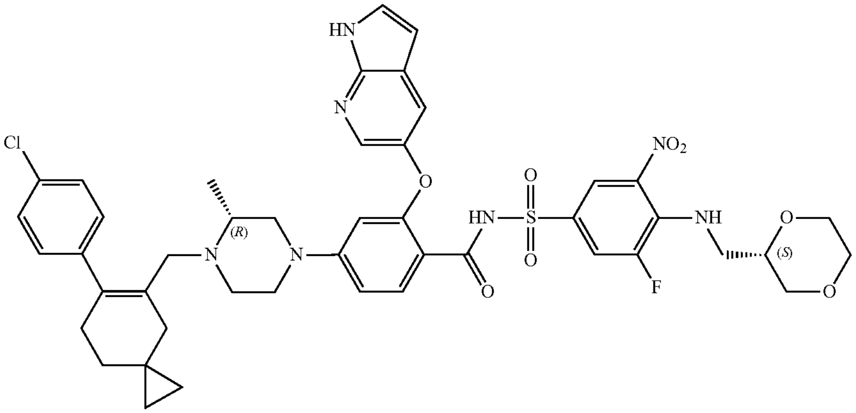 | MS m/z (ESI): 900 & 902 [M + 1]; $^1$H NMR (400 MHz, $CDCl_3$) δ 10.11 (brs, 1H), 9.26 (s, 1H), 8.78-8.57 (m, 2H), 8.24-8.16 (m, 1H), 8.00-7.89 (m, 2H), 7.72-7.65 (m, 1H), 7.49-7.42 (m, 1H), 7.24-7.20 (m, 2H), 7.03-6.93 (m, 2H), 6.63-6.47 (m, 2H), 5.97 (d, J = 2.0 Hz, 1H), 3.93-3.72 (m, 6H), 3.68-3.55 (m, 2H), 3.50-3.39 (m, 1H), 3.29-3.17 (m, 2H), 3.12-3.02 (m, 1H), 2.78-2.74 (m, 1H), 2.69-2.62 (m, 1H), 2.60-2.45 (m, 2H), 2.36-2.19 (m, 2H), 2.17-2.09 (m, 2H), 1.93-1.72 (m, 2H), 1.50-1.40 (m, 2H), 0.86 (d, J = 4.0 Hz, 3H), 0.38-0.25 (m, 4H). |
| | z | |
| Example 36 N-((4-((((S)-1,4-dioxan-2-yl) methyl)amino)-3-nitrophenyl) sulfonyl)-2-((1H-pyrrolo[2,3-b] pyridin-5-yl)oxy)-4-((R)-4-(6-(4-chlorophenyl)spiro[2.5] oct-5-en-5-yl)methyl)-3-methylpiperazin-1-yl)benzamide | 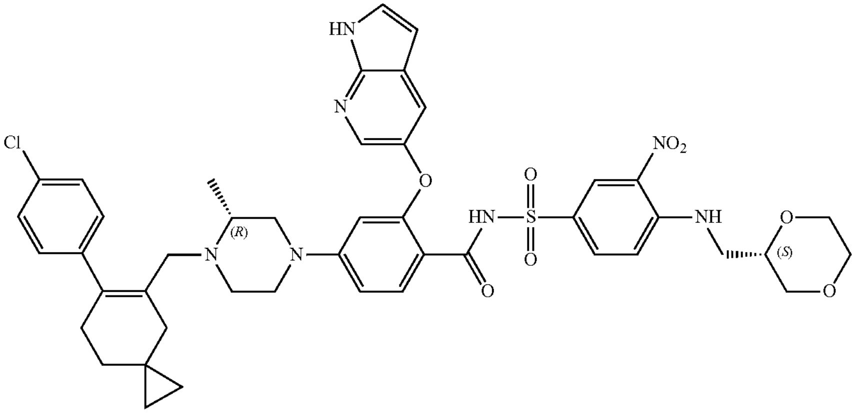 | MS m/z (ESI): 882 & 884 [M + 1]; $^1$H NMR (400 MHz, $CDCl_3$) δ 10.11 (brs, 1H), 9.58 (s, 1H), 8.88 (d, J = 4.0 Hz, 1H), 8.61 (t, J = 4.0 Hz, 1H), 8.22-8.13 (m, 2H), 7.94 (d, J = 8.0 Hz, 1H), 7.73-7.66 (m, 1H), 7.51-7.44 (m, 1H), 7.25-7.20 (m, 2H), 7.00-6.93 (m, 2H), 6.88 (d, J = 8.0 Hz, 1H), 6.58-6.48 (m, 2H), 5.97 (d, J = 2.0 Hz, 1H), 3.98-3.72 (m, 6H), 3.69-3.64 (m, 1H), 3.51-3.28 (m, 2H), 3.26-3.19 (m, 2H), 3.12-3.03 (m, 1H), 2.80-2.74 (m, 1H), 2.69-2.65 (m, 1H), 2.59-2.48 (m, 2H), 2.36-2.19 (m, 2H), 2.18-2.09 (m, 2H), 1.93-1.83 (m, 2H), 1.50-1.42 (m, 2H), 0.86 (d, J = 4.0 Hz, 3H), 0.38-0.25 (m, 4H). |

-continued

| Example and name | structure | MS & $^1$H NMR |
|---|---|---|
| Example 37 (R)-2-((1H-pyrrolo[2,3-b] pyridin-5-yl)-4-(4-((6-(4-chlorophenyl)spiro[2.5]oct-5-en-5-yl)methyl)-3-methylpiperazin-1-yl)-N-((3-fluoro-5-nitro-4--(((tetrahydro-2H-pyran-4-yl)methyl)amino)phenyl) sulfonyl)benzamide | 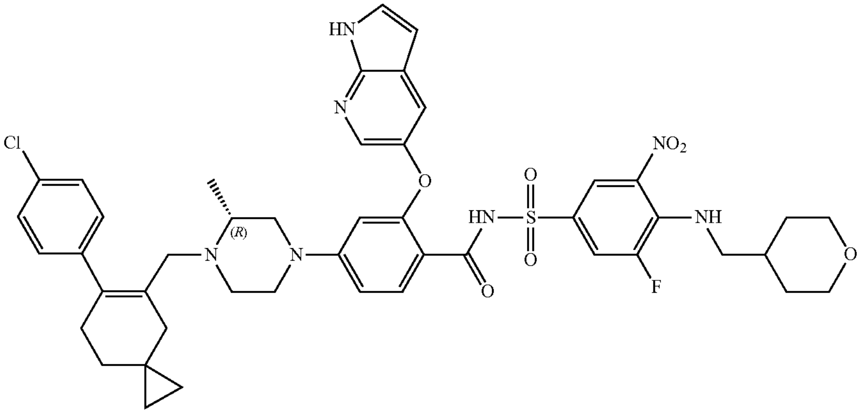 | MS m/z (ESI): 898 & 890 [M + 1]; $^1$H NMR (400 MHz, $CDCl_3$) δ 10.13 (brs, 1H), 9.67 (s, 1H), 8.74-8.68 (m, 1H), 8.55-8.42 (m, 1H), 8.25-8.11 (m, 1H), 8.00-7.90 (m, 2H), 7.72-7.66 (m, 1H), 7.53-7.43 (m, 1H), 7.24-7.00 (m, 2H), 7.02-6.85 (m, 2H), 6.60-6.48 (m, 2H), 5.97 (d, J = 2.0 Hz, 1H), 4.10-3.98 (m, 2H), 3.60-3.51 (m, 2H), 3.31-3.17 (m, 2H), 3.12-3.01 (m, 1H), 2.81-2.64 (m, 2H), 2.61-2.46 (m, 2H), 2.37-2.21 (m, 2H), 2.18-2.06 (m, 2H), 1.96-1.82 (m, 2H), 1.79-1.65 (m, 4H), 1.50-1.34 (m, 5H), 0.86 (d, J = 4.0 Hz, 3H), 0.38-0.25 (m, 4H). |
| Example 38 (R)-2-((1H-pyrrolo[2,3-b] pyridin-5-yl)oxy)-4-((4-((6-(4-chlorophenyl)spiro[2.5]oct-5-en-5-yl)methyl)-3-methylpiperazin-1-yl)-N-((3--nitro-4--(((tetrahydro-2H-pyran-4-yl) methyl)amino)phenyl)sulfonyl) benzamide | 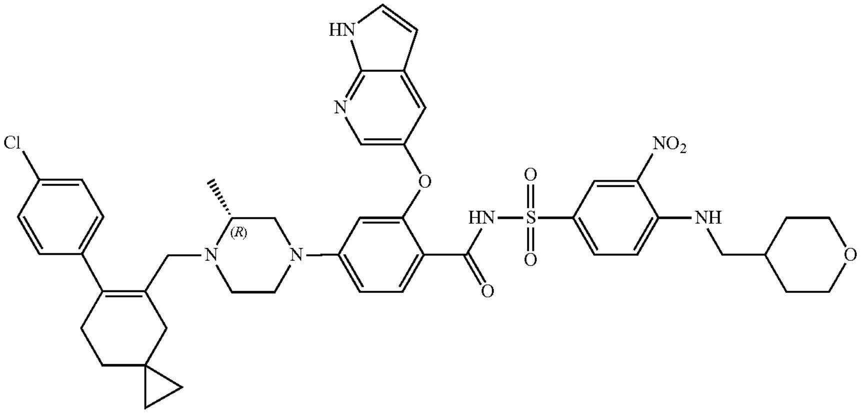 | MS m/z (ESI): 880 & 882 [M + 1]; $^1$H NMR (400 MHz, $CDCl_3$) δ 10.13 (brs, 1H), 9.68 (s, 1H), 8.88 (d, J = 4.0 Hz, 1H), 8.52 (t, J = 4.0 Hz, 1H), 8.25-8.11 (m, 2H), 7.94 (d, J = 8.0 Hz, 1H), 7.72-7.66 (m, 1H), 7.53-7.43 (m, 1H), 7.24-7.20 (m, 2H), 7.02-6.85 (m, 3H), 6.60-6.48 (m, 2H), 5.97 (d, J = 2.0 Hz, 1H), 4.10-3.98 (m, 2H), 3.47-3.39 (m, 2H), 3.31-3.23 (m, 3H), 3.12-3.01 (m, 1H), 2.81-2.64 (m, 2H), 2.61-2.46 (m, 2H), 2.37-2.20 (m, 2H), 2.15-2.06 (m, 2H), 2.05-1.93 (m, 2H), 1.89-1.85 (m, 1H), 1.67-1.55 (m, 2H), 1.43-1.33 (m, 5H), 0.86 (d, J = 4.0 Hz, 3H), 0.38-0.25 (m, 4H). |

The synthetic procedures of Examples 39 to 42 can be referred to the procedure of Example 31.

| Example and name | structure | MS & $^1$H NMR |
|---|---|---|
| Example 39<br>(R)-2-((1H-pyrrolo[2,3-b]pyridin-5-yl)oxy)-4-(4-((4'-chloro-4,4,5,5-tetramethyl-3,4,5,6-tetrahydro-[1,1'-biphenyl]-2-yl)methyl)-3-methylpiperazin-1-yl)-N-((3-nitro-4--(((tetrahydro-2H-pyran-4-yl)methyl)amino)phenyl)sulfonyl)benzamide | 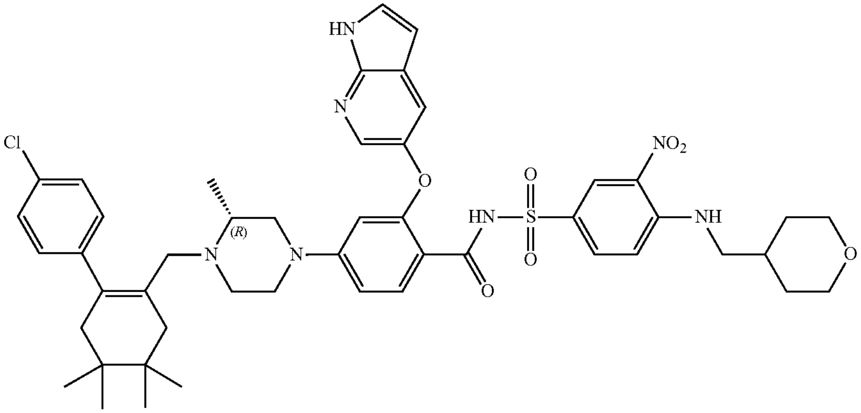 | MS m/z (ESI): 910 & 912 [M + 1];<br>$^1$H NMR (400 MHz, $CDCl_3$) δ 9.03 (brs, 1H), 8.90-8.86 (m, 1H), 8.55-8.47 (m, 1H), 8.25-8.13 (m, 2H), 7.97-7.91 (m, 1H), 7.72-7.66 (m, 1H), 7.47-7.42 (m, 1H), 7.24-7.20 (m, 3H), 6.94-6.88 (m, 3H), 6.57-6.50 (m, 1H), 5.98 (s, 1H), 4.08-3.99 (m, 2H), 3.47-3.37 (m, 2H), 3.30-3.18 (m, 4H), 3.11-3.04 (m, 1H), 2.83-2.76 (m, 1H), 2.66-2.56 (m, 2H), 2.51-2.44 (m, 1H), 1.82-1.70 (m, 6H), 1.49-1.40 (m, 5H), 1.29-1.23 (m, 3H), 0.92-0.86 (m, 12H). |
| Example 40<br>(R)-2-((1H-pyrrolo[2,3-b]pyridin-5-yl)oxy)-4-(4-((4'-chloro-4,4,5,5-tetramethyl-3,4,5,6-tetrahydro-[1,1'-biphenyl]-2-yl)methyl)-3-methylpiperazin-1-yl)-N-((3-fluoro-5-nitro-4--((tetrahydro-2H-pyran-4-yl)methyl)amino)phenyl)sulfonyl)benzamide | 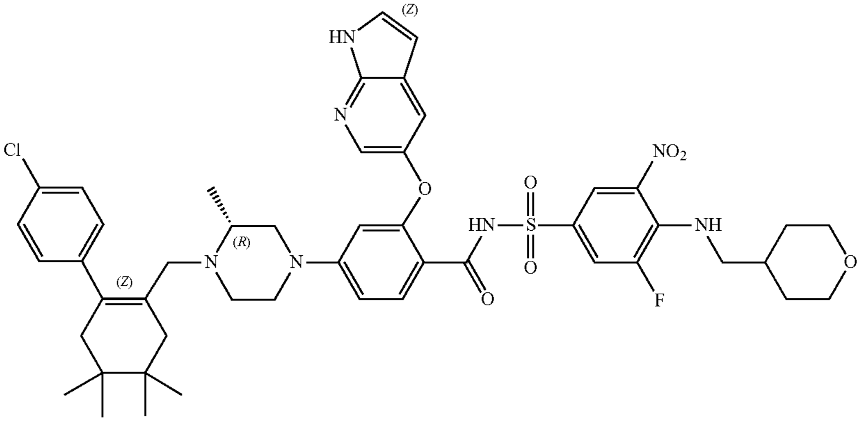 | MS m/z (ESI): 928 & 930 [M + 1];<br>$^1$H NMR (400 MHz, $CDCl_3$) δ 10.90 (brs, 1H), 9.98 (brs, 1H), 8.68 (s, 1H), 8.55-8.48 (m, 1H), 8.17-8.05 (m, 1H), 8.01-7.86 (m, 3H), 7.60-7.52 (m, 1H), 7.34-7.27 (m, 2H), 6.94-6.90 (m, 2H), 6.69-6.66 (m, 1H), 6.60-6.53 (m, 1H), 5.98 (s, 1H), 4.08-3.96 (m, 4H), 3.92-3.74 (m, 1H), 3.61-3.53 (m, 2H), 3.53-3.31 (m, 6H), 3.31-3.19 (m, 2H), 2.14-1.82 (m, 5H), 1.75-1.66 (m, 2H), 1.47-1.23 (m, 5H), 0.90 (m, 12H). |

-continued

| Example and name | structure | MS & $^1$H NMR |
| --- | --- | --- |
| Example 41 N-((4-((((S)-1,4-dioxan-2-yl) methyl)amino)-3-fluoro-5-nitrophenyl)sulfonyl)-2-((1H-pyrrolo[2,3-b]pyridin-5-yl)oxy)-4-((R)-4-((4'-chloro-4,4,5,5-tetramethyl-3,4,5,6-tetrahydro-[1,1'-biphenyl]-2-yl)methyl)-3-methylpiperazin-1-yl)benzamide | 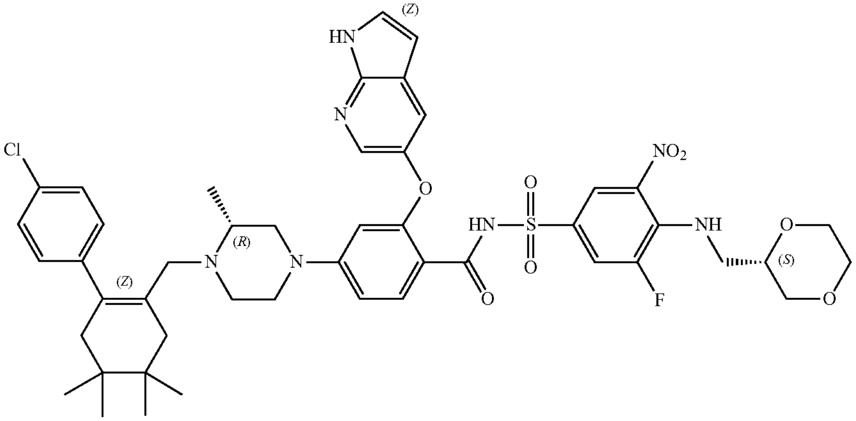 | MS m/z (ESI): 930 & 932 [M + 1]; $^1$H NMR (400 MHz, $CDCl_3$) δ 11.27 (brs, 1H), 9.91 (brs, 1H), 8.74-8.59 (m, 2H), 8.18-8.05 (m, 1H), 8.03-7.85 (m, 3H), 7.60-7.52 (m, 1H), 7.34-7.30 (m, 2H), 6.99-6.88 (m, 2H), 6.71-6.53 (m, 2H), 5.99 (s, 1H), 3.95-3.72 (m, 6H), 3.69-3.58 (m, 2H), 3.54-3.35 (m, 4H), 3.32-3.22 (m, 2H), 3.06-2.80 (m, 4H), 2.03-1.95 (m, 4H), 1.55-1.25 (m, 3H), 1.02-0.76 (m, 12H). |
| Example 42 N-((4-((((S)-1,4-dioxan-2-yl) methyl)amino)-3-nitrophenyl) sulfonyl)-2-((1H-pyrrolo[2,3-b] pyridin-5-yl)oxy)-4-((R)-4-((4'-chloro-4,4,5,5-tetramethyl-3,4,5,6-tetrahydro-[1,1'-biphenyl]-2-yl) methyl)-3-methylpiperazin-1-yl) benzamide | 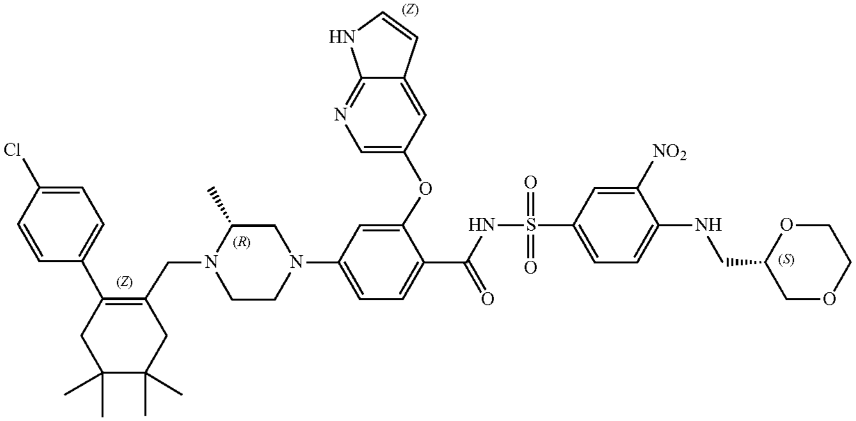 | MS m/z (ESI): 912 & 914 [M + 1]; $^1$H NMR (400 MHz, $CDCl_3$) δ 10.92 (brs, 1H), 9.92 (brs, 1H), 8.87-8.82 (m, 1H), 8.66-8.58 (s, 1H), 8.20-8.05 (m, 2H), 8.01-7.83 (m, 2H), 7.58-7.50 (m, 1H), 7.34-7.30 (m, 2H), 7.00-6.86 (m, 3H), 6.73-6.50 (m, 2H), 5.99 (s, 1H), 4.00-3.73 (m, 6H), 3.72-3.60 (m, 2H), 3.60-3.40 (m, 5H), 3.39-3.16 (m, 5H), 2.16-2.01 (m, 4H), 1.48-1.25 (m, 3H), 1.02-0.76 (m, 12H). |

The synthetic procedures of Examples 43 to 46 can be referred to the procedure of Example 8.

| Example and name | structure | MS & $^1$H NMR |
|---|---|---|
| Example 43 (R)-2-((1H-pyrrolo[2,3-b]pyridin-5-yl)oxy)-4-(4-((4'-chloro-4,4-dimethyl-3,4,5,6-tetrahydro[1,1'-biphenyl]-2-yl)methyl)-2-methylpiperazin-1-yl)-N-((3-fluoro-5-nitro-4--(((tetrahydro-2H-pyran-4-yl)methyl)amino)phenyl)sulfonyl)benzamide | 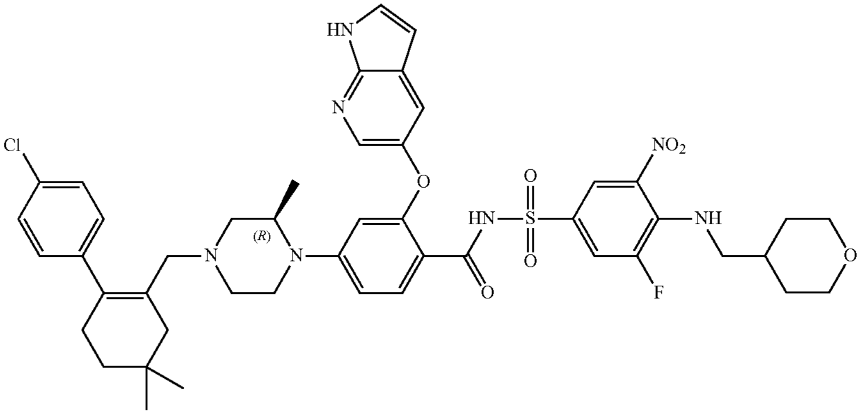 | MS m/z (ESI): 900 & 902 [M + 1]; $^1$H NMR (400 MHz, $CDCl_3$) δ 11.75 (s, 1H), 9.87 (s, 1H), 8.59-8.57 (m, 2H), 8.33-7.78 (m, 4H), 7.62 (s, 1H), 7.43-7.29 (m, 2H), 7.10-6.86 (m, 2H), 6.85-6.69 (m, 1H), 6.59 (s, 1H), 6.00 (s, 1H), 4.30-3.96 (m, 4H), 3.65-3.56 (m, 5H), 3.48-3.19 (m, 6H), 2.70-2.48 (m, 2H), 2.43-2.16 (m, 2H), 2.13-1.81 (m, 3H), 1.76-1.61 (m, 2H), 1.55-1.33 (m, 3H), 1.28-1.14 (m, 2H), 0.94 (s, 3H), 0.93 (s, 3H). |
| Example 44 N-((4-((((S)-1,4-dioxan-2-yl)methyl)amino)-3-nitrophenyl)sulfonyl)-2-((1H-pyrrolo[2,3-b]pyridin-5-yl)oxy)-4-((R)-4-((4'-chloro-4,4-dimethyl-3,4,5,6-tetrahydro-[1,1'-biphenyl]-2-yl)methyl)-2-methylpiperazin-1-yl)benzamide | 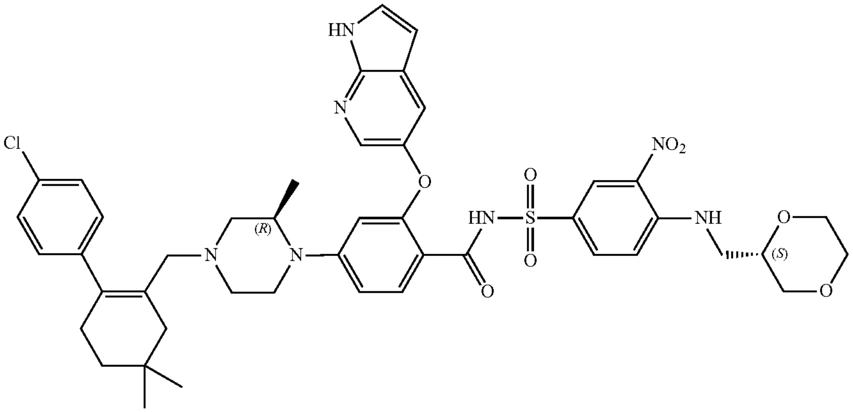 | MS m/z (ESI): 884 & 886 [M + 1]; $^1$H NMR (400 MHz, $CDCl_3$) δ 11.83 (s, 1H), 9.84 (s, 1H), 8.81 (s, 1H), 8.71-8.57 (m, 1H), 8.26-7.90 (m, 4H), 7.59 (s, 1H), 7.42-7.27 (m, 3H), 6.97-6.86 (m, 2H), 6.69 (s, 1H), 6.57 (s, 1H), 5.95 (s, 1H), 4.15-4.01 (m, 1H), 3.96-3.85 (m, 5H), 3.84-3.60 (m, 6H), 3.55-3.18 (m, 5H), 2.65-2.50 (m, 1H), 2.41-2.19 (m, 2H), 2.07-1.88 (m, 2H), 1.54-1.40 (m, 2H), 1.34-1.13 (m, 3H), 0.94 (s, 3H), 0.93 (s, 3H). |

-continued

| Example and name | structure | MS & $^1$H NMR |
|---|---|---|
| Example 45 N-((4-((((S)-1,4-dioxan-2-yl) methyl)amino)-3-fluoro-5-nitrophenyl)sulfonyl)-2-((1H-pyrrolo[2,3-b]pyridin-5-yl)oxy)-4-((R)-4-((4'-chloro-4,4-dimethyl-3,4,5,6-tetrahydro-[1,1'-biphenyl]-2-yl)methyl)-2-methylpiperazin-1-yl)benzamide | 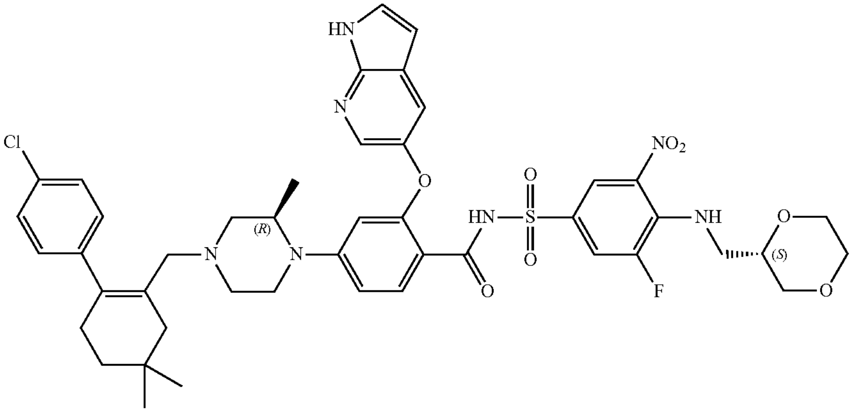 | MS m/z (ESI): 902 & 904 [M + 1]; $^1$H NMR (400 MHz, $CDCl_3$) δ 11.80 (s, 1H), 9.85 (s, 1H), 8.65 (s, 2H), 8.10 (s, 1H), 8.02-7.93 (m, 2H), 7.90 (d, J = 13.2 Hz, 1H), 7.59 (s, 1H), 7.31 (d, J = 8.2 Hz, 2H), 6.94 (d, J = 8.2 Hz, 2H), 6.70 (s, 1H), 6.58 (s, 1H), 5.96 (s, 1H), 4.16-3.98 (m, 1H), 3.91-3.85 (m, 4H), 3.83-3.69 (m, 4H), 3.69-3.55 (m, 3H), 3.54-3.47 (m, 1H), 3.46-3.37 (m, 2H), 3.3-3.20 (m, 2H), 2.64-2.49 (m, 1H), 2.35-2.23 (m, 2H), 2.08-1.91 (m, 2H), 1.50-1.42 (m, 2H), 1.30-1.15 (m, 3H), 0.95 (s, 3H), 0.94 (s, 3H). |
| Example 46 N-((4-((((S)-1,4-dioxan-2-yl) methyl)amino)-3-fluoro-5-nitrophenyl)sulfonyl)-2-((1H-pyrrolo[2,3-b]pyridin-5-yl)oxy)-4-((R)-4-((4'-chloro-5,5-dimethyl-3,4,5,6-tetrahydro-[1,1'-biphenyl-2-yl)methyl)-2-methylpiperazin-1-yl)benzamide | 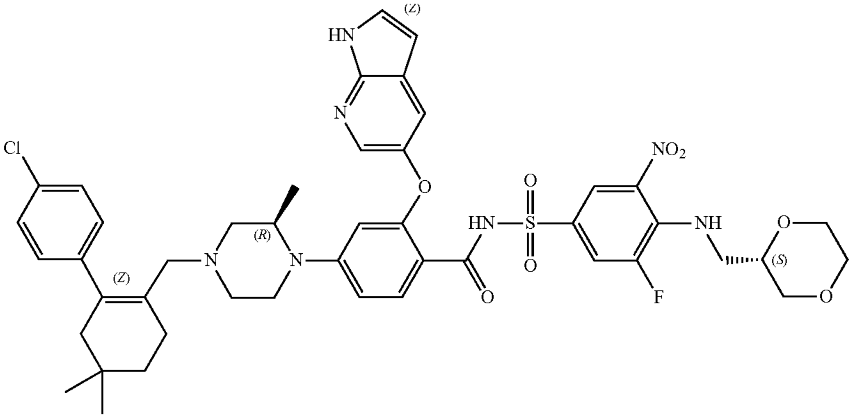 | MS m/z (ESI): 902 & 904 [M + 1]; $^1$H NMR (400 MHz, $CDCl_3$) δ 9.68 (s, 1H), 8.69 (s, 1H), 8.62-8.59 (m, 1H), 8.20 (s, 1H), 7.96-7.91 (m, 2H), 7.70 (s, 1H), 7.48-7.46 (m, 1H), 7.21 (d, J = 8.0 Hz, 2H), 6.91 (d, J = 8.0 Hz, 2H), 6.55-6.53 (m, 2H), 5.98 (s, 1H), 3.88-3.74 (m, 6H), 3.67-3.61 (m, 2H), 3.46-3.42 (m, 1H), 3.16-3.13 (m, 1H), 2.96-2.93 (m, 1H), 2.74-2.63 (m, 3H), 2.52-2.49 (m, 1H), 2.20-1.16 (m, 2H), 1.98-1.94 (m, 2H), 1.78-1.70 (m, 3H), 1.41-1.38 (m, 2H), 1.04 (d, J = 6.4 Hz, 3H), 0.94 (s, 3H), 0.93 (s, 3H). |

The synthetic procedures of Examples 47 to 56 can be referred to the procedure of Example 1.

| Example and name | structure | MS & $^1$H NMR |
|---|---|---|
| Example 47 N-((4-((((S)-1,4-dioxan-2-yl) methyl)amino)-3-fluoro-5-nitrophenyl)sulfonyl)-2-((1H-pyrrolo[2,3-b]pyridin-5-yl)oxy)-4-((S)-4-((4'-chloro-5,5-dimethyl-3,4,5,6-tetrahydro-[1,1'-biphenyl]-2-yl)methyl)-3-methylpiperazin-1-yl) benzamide | 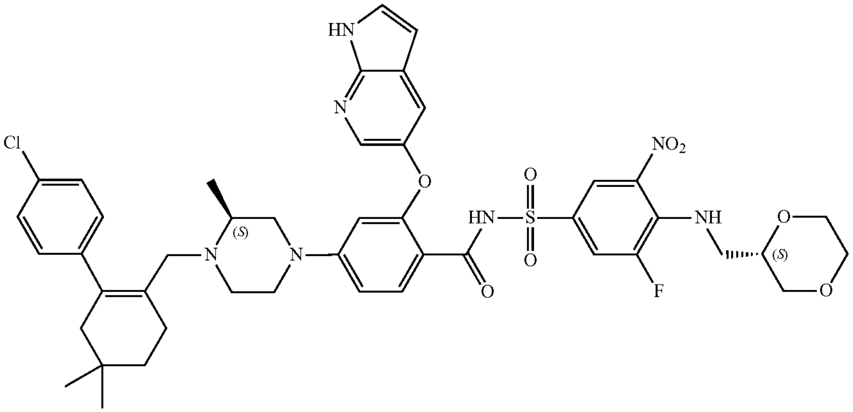 | MS m/z (ESI): 902 & 904 [M + 1]; $^1$H NMR (400 MHz, $CDCl_3$) δ 10.12 (s, 1H), 9.73 (s, 1H), 8.69 (s, 1H), 8.61-8.57 (m, 1H), 8.20 (d, J = 2.4 Hz, 1H), 7.96-7.91 (m, 2H), 7.69 (d, J = 2.4 Hz, 1H), 7.47 (d, J = 2.4 Hz, 1H), 7.22 (d, J = 8.0 Hz, 2H), 6.91 (d, J = 8.0 Hz, 2H), 6.56-6.51 (m, 2H), 5.98 (d, J = 1.6 Hz, 1H), 3.90-3.74 (m, 7H), 3.68-3.60 (m, 2H), 3.49-3.43 (m, 1H), 3.27-3.22 (m, 2H), 3.13-3.07 (m, 1H), 2.83-2.79 (m, 1H), 2.65-2.57 (m, 2H), 2.52-2.49 (m, 1H), 2.29-2.21 (m, 2H), 2.14-2.10 (m, 1H), 1.97-1.95 (m, 3H), 1.79-67 (m, 4H), 0.93 (s, 3H), 0.92 (s, 3H). |
| Example 48 N-((4-((((S)-1,4-dioxan-2-yl) methyl)amino)-3-nitrophenyl) sulfonyl)-2-((1H-pyrrolo[2,3-b] pyridin-5-yl)oxy)-4-((S)-4-((4'-chloro-5,5-dimethyl-3,4,5,6-tetrahydro-[1,1'-biphenyl]-2-yl)methyl)-3-methylpiperazin-1-yl) benzamide | 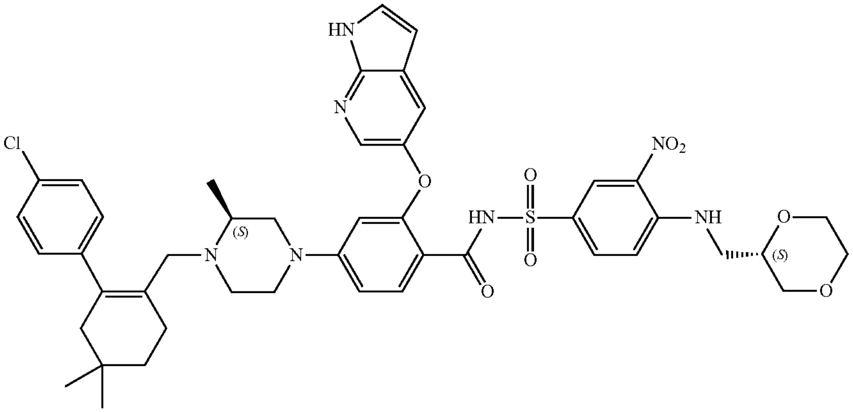 | MS m/z (ESI): 884 & 886 [M + 1]; $^1$H NMR (400 MHz, $CDCl_3$) δ 10.11 (s, 1H), 9.70 (s, 1H), 8.87 (d, J = 2.0 Hz, 1H), 8.62-8.59 (m, 1H), 8.20 (d, J = 2.0 Hz, 1H), 8.17-8.14 (m, 1H), 7.95 (d, J = 8.8 Hz, 1H), 7.69 (d, J = 2.0 Hz, 1H), 7.47-7.45 (m, 1H), 7.27-7.25 (m, 1H), 7.22 (d, J = 8.0 Hz, 2H), 6.91 (d, J = 8.0 Hz, 2H), 6.54-6.52 (m, 2H), 5.97 (d, J = 1.6 Hz, 1H), 3.91-3.75 (m, 7H), 3.68-3.62 (m, 1H), 3.50-3.48 (m, 2H), 3.25-3.22 (m, 2H), 3.13-3.08 (m, 1H), 2.82-2.77 (m, 1H), 2.65-2.58 (m, 2H), 2.51-2.48 (m, 1H), 2.29-2.21 (m, 2H), 2.16-2.13 (m, 1H), 1.96-1.94 (m, 3H), 1.79-67 (m, 4H), 0.93 (s, 3H), 0.92 (s, 3H). |

-continued

| Example and name | structure | MS & $^1$H NMR |
| --- | --- | --- |
| Example 49 N-((4-((((S)-1,4-dioxan-2-yl) methyl)amino)-3-nitrophenyl) sulfonyl)-2-((1H-pyrrolo[2,3-b]pyridin-5-yl)oxy)-4-((S)-4-((4'-chloro-4,4-dimethyl-3,4,5,6-tetrahydro-[1,1'-biphenyl]-2-yl)methyl)-3-methylpiperazin-1-yl) benzamide | 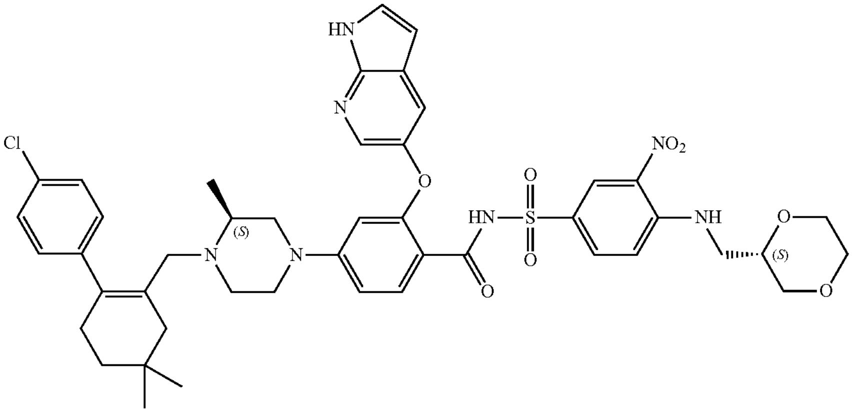 | MS m/z (ESI): 884 & 886 [M + 1]; $^1$H NMR (400 MHz, $CDCl_3$) δ 10.02 (s, 1H), 9.04 (s, 1H), 8.80 (d, J = 2.2 Hz, 1H), 8.58-8.52 (m, 1H), 8.17-8.06 (m, 2H), 7.87 (d, J = 9.1 Hz, 1H), 7.61 (d, J = 2.4 Hz, 1H), 7.39-7.35 (m, 1H), 6.89-6.55 (m, 4H), 6.50-6.44 (m, 2H), 5.90 (d, J = 2.1 Hz, 1H), 3.89-3.73 (m, 4H), 3.74-3.66 (m, 2H), 3.68-3.60 (m, 2H), 3.37-3.31 (m, 2H), 3.33-3.23 (m, 2H), 3.17 (d, J = 9.2 Hz, 2H), 2.99-2.91 (m, 1H), 2.72-2.62 (m, 1H), 2.63-2.49 (m, 2H), 2.41-2.38 (m, 2H), 2.34-2.22 (m, 2H), 2.21-2.02 (m, 2H), 2.02-1.90 (d, J = 3.5 Hz, 3H), 0.95 (s, 3H), 0.94 (s, 3H). |
| Example 50 (S)-2-((1H-pyrrolo[2,3-b] pyridin-5-yl)oxy)-4-(4-((4'-chloro-5,5-dimethyl-3,4,5,6-tetrahydro-[1,1'-biphenyl]-2-yl) methyl)-3-methylpiperazin-1-yl)-N-((3-nitro-4--(((tetrahydro-2H-pyran-4-yl)methyl) amino)phenyl)sulfonyl) benzamide | 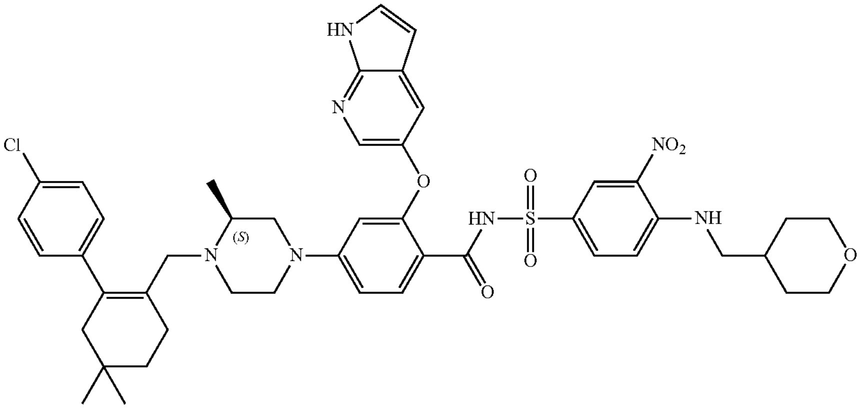 | MS m/z (ESI): 882 & 884 [M + 1]; $^1$H NMR (400 MHz, $CDCl_3$) δ 10.09 (brs, 1H), 9.04 (s, 1H), 8.88 (d, J = 4.0 Hz, 1H), 8.53-8.51 (m, 1H), 8.23-8.12 (m, 2H), 7.94 (d, J = 8.0 Hz, 1H), 7.69 (d, J = 4.0 Hz, 1H), 7.49-7.41 (m, 1H), 7.23 (d, J = 8.0 Hz, 2H), 6.93-6.88 (m, 2H), 6.59-6.48 (m, 2H), 5.97 (d, J = 2.0 Hz, 1H), 4.03-3.98 (m, 2H), 3.48-3.37 (m, 2H), 3.29-3.20 (m, 3H), 3.15-3.06 (m, 1H), 2.84-2.75 (m, 1H), 2.66-2.46 (m, 3H), 2.31-2.10 (m, 3H), 2.06-1.93 (m, 4H), 1.82-1.70 (m, 2H), 1.46-1.36 (m, 5H), 0.95 (s, 3H), 0.94 (s, 3H), 0.84 (d, J = 6.4 Hz, 3H). |

-continued

| Example and name | structure | MS & $^1$H NMR |
| --- | --- | --- |
| Example 51 N-((4-((((R)-1,4-dioxan-2-yl) methyl)amino)-3-nitrophenyl) sulfonyl)-2-((1H-pyrrolo[2,3-b]pyridin-5-yl)oxy)-4-((S)-4-((4'-chloro-5,5-dimethyl-3,4,5,6-tetrahydro-[1,1'-biphenyl]-2-yl)methyl)-3-methylpiperazin-1-yl) benzamide | 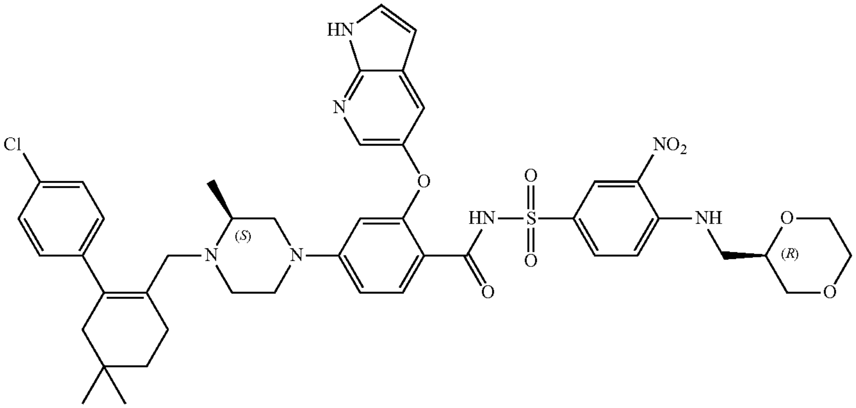 | MS m/z (ESI): 884 & 886 [M + 1]; $^1$H NMR (400 MHz, $CDCl_3$) δ 10.10 (s, 1H), 9.32 (s, 1H), 8.87 (d, J = 1.6 Hz, 1H), 8.62-8.60 (m, 1H), 8.20 (d, J = 2.0 Hz, 1H), 8.19-8.18 (m, 1H), 8.15 (d, J = 8.8 Hz, 1H), 7.94 (d, J = 8.8 Hz, 1H), 7.69 (d, J = 1.6 Hz, 1H), 7.50-7.48 (m, 1H), 7.25-7.21 (m, 1H), 6.92-6.88 (m, 3H), 6.54-6.52 (m, 2H), 5.97 (d, J = 1.6 Hz, 1H), 3.91-3.75 (m, 6H), 3.68-3.63 (m, 2H), 3.50-3.34 (m, 2H), 3.25-3.22 (m, 2H), 3.13-3.09 (m, 1H), 2.80-2.77 (m, 1H), 2.65-2.56 (m, 2H), 2.51-2.48 (m, 1H), 2.27-2.22 (m, 2H), 2.16-2.13 (m, 1H), 1.96-1.94 (m, 3H), 1.78-1.63 (m, 4H), 0.93 (s, 3H), 0.92 (s, 3H). |
| Example 52 N-((4-((((R)-1,4-dioxan-2-yl) methyl)amino)-3-nitrophenyl) sulfonyl)-2-((1H-pyrrolo [2,3-b]pyridin-5-yl)oxy)-4-((R)-4-((4'-chloro-5,5-dimethyl-3,4,5,6-tetrahydro-[1,1'-biphenyl]-2-yl)methyl)-3-methylpiperazin-1-yl) benzamide | 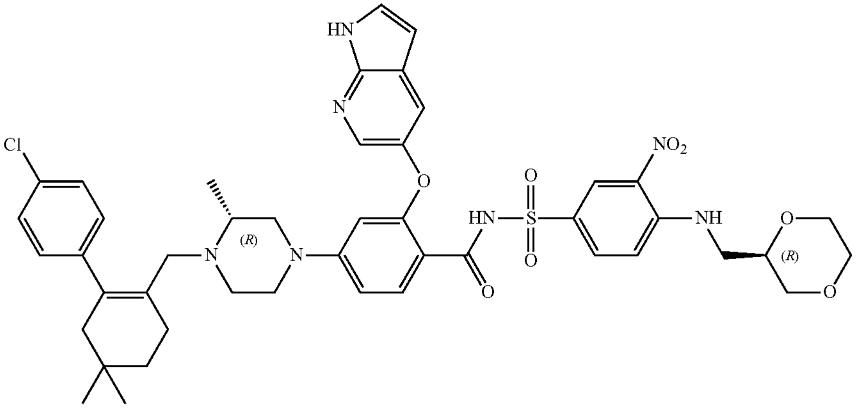 | MS m/z (ESI): 884 & 886 [M + 1]; $^1$H NMR (400 MHz, $CDCl_3$) δ 10.12 (brs, 1H), 9.41 (s, 1H), 8.73-8.52 (m, 2H), 8.18 (d, J = 2.2 Hz, 1H), 8.01-7.87 (m, 2H), 7.69 (d, J = 2.2 Hz, 1H), 7.52-7.42 (m, 1H), 7.25-7.20 (m, 2H), 6.96-6.88 (m, 2H), 6.62-6.50 (m, 2H), 5.98 (d, J = 2.0 Hz, 1H), 3.93-3.73 (m, 6H), 3.70-3.57 (m, 2H), 3.46-3.39 (m, 2H), 3.30-3.19 (m, 2H), 3.16-3.06 (m, 1H), 2.86-2.74 (m, 1H), 2.70-2.45 (m, 3H), 2.33-2.10 (m, 3H), 2.02-1.93 (m, 2H), 1.49-1.36 (m, 2H), 0.93 (s, 3H), 0.92 (s, 3H), 0.89 (d, J = 5.2 Hz, 3H). |

-continued

| Example and name | structure | MS & $^{1}$H NMR |
| --- | --- | --- |
| Example 53 N-((4-((((R)-1,4-dioxan-2-yl)methyl)amino)-3-nitrophenyl)sulfonyl)-2-((1H-pyrrolo[2,3-b]pyridin-5-yl)oxy)-4-((S)-4-((4'-chloro-4,4-dimethyl-3,4,5,6-tetrahydro-[1,1'-biphenyl]-2-yl)methyl)-3-methylpiperazin-1-yl)benzamide | 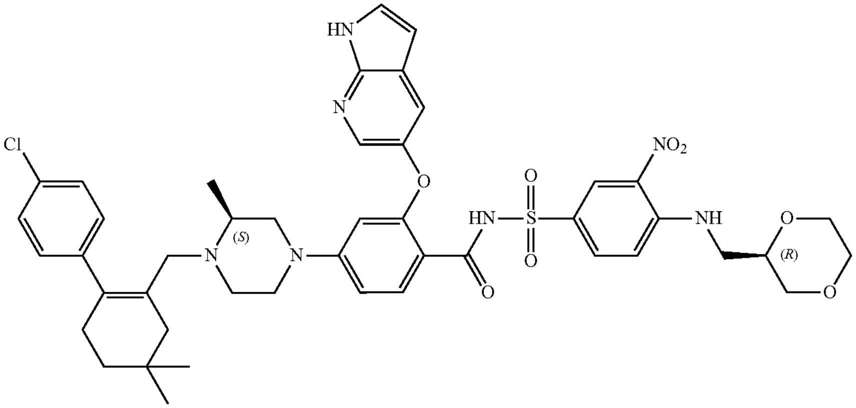 | MS m/z (ESI): 884 & 886 [M + 1]; $^{1}$H NMR (400 MHz, $CDCl_3$) δ 12.58 (s, 1H), 9.76 (s, 1H), 8.78-8.70 (m, 1H), 8.63-8.60 (m, 1H), 8.25-8.05 (m, 3H), 7.87 (d, J = 8.7 Hz, 1H), 7.64 (s, 1H), 7.35-7.30 (m, 1H), 7.05-6.85 (m, 3H), 6.70-6.62 (m, 1H), 6.59 (d, J = 8.1 Hz, 1H), 6.10-5.95 (m, 1H), 4.0-3.80 (m, 4H), 3.75-3.64 (m, 2H), 3.52-3.36 (m, 4H), 3.34-3.21 (m, 4H), 2.29-2.23 (m, 2H), 2.19-2.10 (m, 2H), 1.55-1.41 (m, 4H), 1.35-1.20 (m, 5H), 0.96 (s, 3H), 0.93 (s, 3H). |
| Example 54 N-((4-((((R)-1,4-dioxan-2-yl)methyl)amino)-3-nitrophenyl)sulfonyl)-2-((1H-pyrrolo[2,3-b]pyridin-5-yl)oxy)-4-((R)-4-((4'-chloro-4,4-dimethyl-3,4,5,6-tetrahydro-[1,1'-biphenyl]-2-yl)methyl)-3-methylpiperazin-1-yl)benzamide | 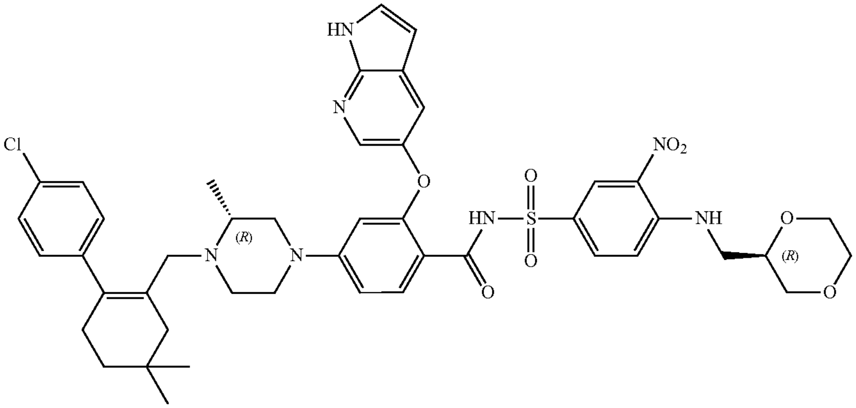 | MS m/z (ESI): 884 & 886 [M + 1]; $^{1}$H NMR (400 MHz, $CDCl_3$) δ 11.95 (s, 1H), 9.85 (s, 1H), 8.81-8.75 (m, 1H), 8.63-8.60 (m, 1H), 8.25-7.97 (m, 3H), 7.91 (d, J = 8.7 Hz, 1H), 7.59 (s, 1H), 7.35-7.30 (m, 1H), 7.15-6.90 (m, 3H), 6.70-6.62 (m, 1H), 6.59 (d, J = 8.1 Hz, 1H), 6.08-5.95 (m, 1H), 3.95-3.80 (m, 4H), 3.70-3.61 (m, 2H), 3.48-3.35 (m, 4H), 3.34-3.20 (m, 4H), 2.29-2.20 (m, 2H), 2.19-2.09 (m, 2H), 1.52-1.40 (m, 4H), 1.35-1.20 (m, 5H), 0.96 (s, 3H), 0.93 (s, 3H). |

-continued

| Example and name | structure | MS & $^1$H NMR |
|---|---|---|
| Example 55 N-((4-((((R)-1,4-dioxan-2-yl) methyl)amino)-3-fluoro-5-nitrophenyl)sulfonyl)-2-((1H-pyrrolo[2,3-b]pyridin-5-yl)oxy)-4-((R)-4-((4'-chloro-5,5-dimethyl-3,4,5,6-tetrahydro-[1,1'-biphenyl]-2-yl)methyl)-3-methylpiperazin-1-yl)benzamide | 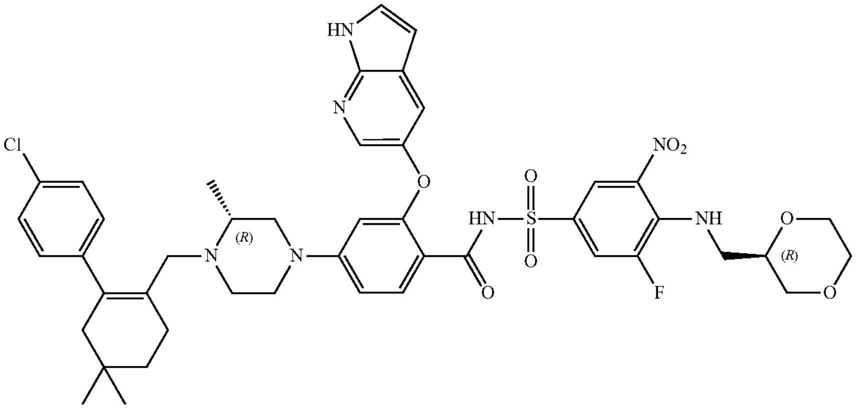 | MS m/z (ESI): 902 & 904 [M + 1]; $^1$H NMR (400 MHz, $CDCl_3$) δ 10.11 (brs, 1H), 9.46 (s, 1H), 8.92-8.82 (d, J = 1.8 Hz, 1H), 8.67-8.54 (m, 1H), 8.24-8.09 (m, 2H), 7.94 (d, J = 9.0 Hz, 1H), 7.75-7.63 (m, 1H), 7.50-7.40 (m, 1H), 7.25-7.19 (m, 2H), 6.97-6.82 (m, 2H), 6.61-6.40 (m, 2H), 5.98 (s, 1H), 4.01-3.72 (m, 5H), 3.71-3.60 (m, 1H), 3.54-3.30 (m, 3H), 3.30-3.04 (m, 3H), 2.89-2.76 (m, 1H), 2.70-2.44 (m, 3H), 2.34-1.89 (m, 6H), 1.45-1.36 (m, 2H), 0.93 (s, 3H), 0.92 (s, 3H), 0.89 (d, J = 5.2 Hz, 3H). |
| Example 56 N-((4-((((R)-1,4-dioxan-2-yl) methyl)amino)-3-fluoro-5-nitrophenyl)sulfonyl)-2-((1H-pyrrolo[2,3-b]pyridin-5-yl)oxy)-4-((S)-4-((4'-chloro-5,5-dimethyl-3,4,5,6-tetrahydro-[1,1'-biphenyl]-2-yl)methyl)-3-methylpiperazin-1-yl) benzamide | 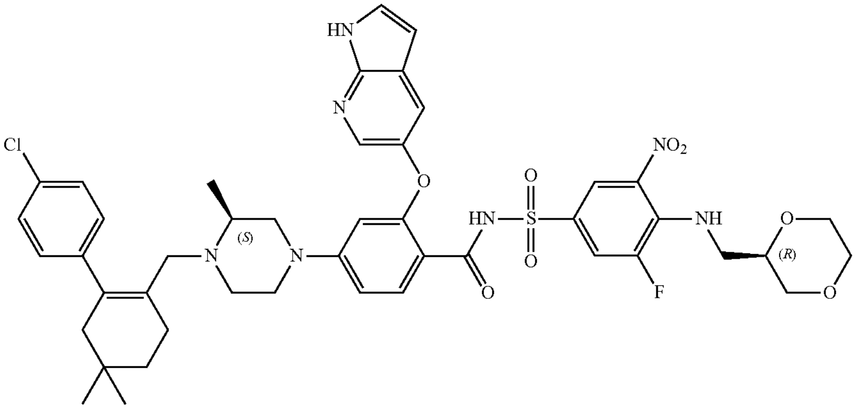 | MS m/z (ESI): 902 & 904 [M + 1]; $^1$H NMR (400 MHz, $CDCl_3$) δ 10.13 (s, 1H), 9.65 (s, 1H), 8.69 (s 1H), 8.61-8.58 (m, 1H), 8.19 (d, J = 2.4 Hz, 1H), 7.96-7.91 (m, 2H), 7.69 (d, J = 2.4 Hz, 1H), 7.47-7.46 (m, 1H), 7.22 (d, J = 8.8 Hz, 2H), 6.91 (d, J = 8.8 Hz, 2H), 6.55-6.54 (m, 2H), 5.97 (d, J = 1.6 Hz, 1H), 3.86-3.74 (m, 6H), 3.67-3.56 (m, 2H), 3.46-3.40 (m, 1H), 3.26-3.22 (m, 2H), 3.13-3.10 (m, 1H), 2.83-2.78 (m, 1H), 2.65-2.57 (m, 2H), 2.52-2.49 (m, 1H), 2.29-2.24 (m, 2H), 2.16-2.13 (m, 1H), 2.03-2.01 (m, 3H), 1.90-1.69 (m, 5H), 0.93 (s, 3H), 0.92 (s, 3H). |

Example 57

2-((1H-Pyrrolo[2,3-b]pyridin-5-yl)oxy)-4-((4aR,8aR)-4-((4'-chloro-5,5-dimethyl-3,4,5,6-tetrahydro-[1,1'-biphenyl]-2-yl)methyl)octahydroquinoxalin-1(2H)-yl)-N-((3-nitro-4-(((tetrahydro-2H-pyran-4-yl)methyl)amino)phenyl)sulfonyl)benzamide

57

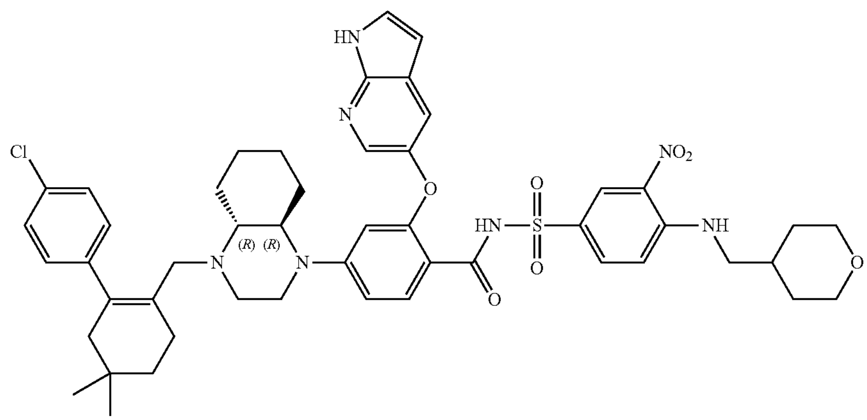

The synthesis of Example 57 was carried out referring to the synthetic procedure of Example 1, wherein in step 2, (R)-2-methylpiperazine was replaced by (4aR,8aR)-decahydroquinoxaline (Synthesis can be referred to: European Journal of Organic Chemistry, 2012(34), 6752-6759; 2012) to give the target compound 2-((1H-pyrrolo[2,3-b]pyridin-5-yl)oxy)-4-((4aR,8aR)-4-((4'-chloro-5,5-dimethyl-3,4,5,6-tetrahydro-[1,1'-biphenyl]-2-yl)methyl)octahydroquinoxalin-1(2H)-yl)-N-((3-nitro-4-(((tetrahydro-2H-pyran-4-yl)methyl)amino)phenyl)sulfonyl)benzamide 57.

MS m/z(ESI): 822 & 824 [M+1];

$^1$H NMR (400 MHz, $CDCl_3$) δ 10.21 (s, 1H), 8.93-8.92 (m, 1H), 8.88-8.87 (m, 1H), 8.57-8.53 (m, 1H), 8.20-8.18 (m, 2H)), 8.01 (d, J=8.4 Hz, 1H), 7.71 (d, J=1.6 Hz, 1H), 7.46-7.44 (m, 1H), 7.20 (d, J=8.0 Hz, 2H), 6.93 (m, 1H), 6.89 (d, J=8.0 Hz, 2H), 6.73-6.70 (m, 1H), 6.57-6.56 (m, 1H), 6.17 (d, J=1.6 Hz, 1H), 4.06-4.02 (m, 2H), 3.45-3.41 (m, 3H), 3.29-3.26 (m, 2H), 3.19-3.16 (m, 1H), 3.04-3.01 (m, 1H), 2.81-2.69 (m, 2H), 2.49-2.43 (m, 2H), 2.22-2.19 (m, 1H), 1.98-1.96 (m, 4H), 1.96-1.92 (m, 4H), 1.85-1.82 (m, 1H), 1.76-1.73 (m, 3H), 1.47-1.44 (m, 3H), 1.41-1.35 (m, 4H), 0.96 (s, 3H), 0.93 (s, 3H).

Example 58

2-((1H-Pyrrolo[2,3-b]pyridin-5-yl)oxy)-4-((2R,5R)-4-((4'-chloro-5,5-dimethyl-3,4,5,6-tetrahydro-[1,1'-biphenyl]-2-yl)methyl)-2,5-dimethylpiperazin-1-yl)-N-((3-nitro-4-(((tetrahydro-2H-pyran-4-yl)methyl)amino)phenyl)sulfonyl)benzamide

58

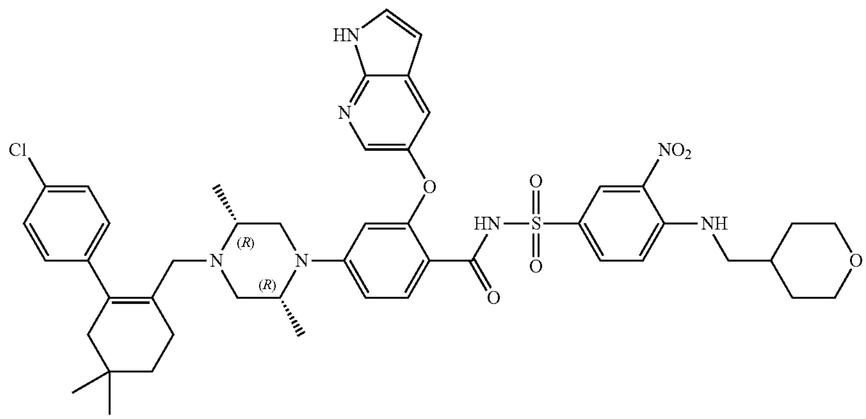

The synthesis of Example 58 was carried out referring to the synthetic procedure of Example 1, wherein in step 2, (R)-2-methylpiperazine is replaced by (2R,5R)-2,5-dimethylpiperazine (synthesis can be referred to: Organic Chemistry Frontiers, 5(23), 3402-3405; 2018) to give the target compound 2-((1H-pyrrolo[2,3-b]pyridin-5-yl)oxy)-4-((2R,5R)-4-((4'-chloro-5,5-dimethyl-3,4,5,6-tetrahydro-[1,1'-biphenyl]-2-yl)methyl)-2,5-dimethylpiperazin-1-yl)-N-((3-nitro-4-(((tetrahydro-2H-pyran-4-yl)methyl)amino)phenyl)sulfonyl)benzamide 58.

MS m/z(ESI): 896 & 898 [M+1];

$^1$H NMR (400 MHz, $CDCl_3$) δ 10.10 (s, 1H), 9.25 (s, 1H), 8.88 (d, J=2.2 Hz, 1H), 8.53-8.51 (m, 1H), 8.20 (d, J=2.5 Hz, 1H), 8.19-8.02 (m, 1H), 7.94 (d, J=9.2 Hz, 1H), 7.70 (d, J=2.4 Hz, 1H), 7.48-7.42 (m, 1H), 7.22 (d, J=8.4 Hz, 2H), 6.99-6.87 (m, 2H), 6.59-6.52 (m, 1H), 6.50-6.40 (m, 1H), 5.95 (d, J=2.2 Hz, 1H), 4.10-4.01 (m, 2H), 3.70-3.60 (m, 2H), 3.47-3.37 (m, 2H), 3.33-3.21 (m, 2H), 3.19-3.03 (m, 2H), 2.59-2.50 (m, 2H), 2.39-2.31 (m, 2H), 1.97-1.90 (m, 3H), 1.82-1.71 (m, 2H), 1.46-1.33 (m, 3H), 1.28-1.20 (m, 3H), 1.25-1.15 (m, 4H), 1.02-1.00 (m, 2H), 0.95 (s, 3H), 0.93 (s, 3H).

Example 59

N-((4-((((S)-1,4-Dioxan-2-yl)methyl)amino)-3-nitrophenyl)sulfonyl)-2-((1H-pyrrolo [2,3-b]pyridin-5-yl)oxy)-4-((3R,5R)-4-((4'-chloro-5,5-dimethyl-3,4,5,6-tetrahydro-[1,1'-biphenyl]-2-yl)methyl)-3,5-dimethylpiperazin-1-yl)benzamide

59

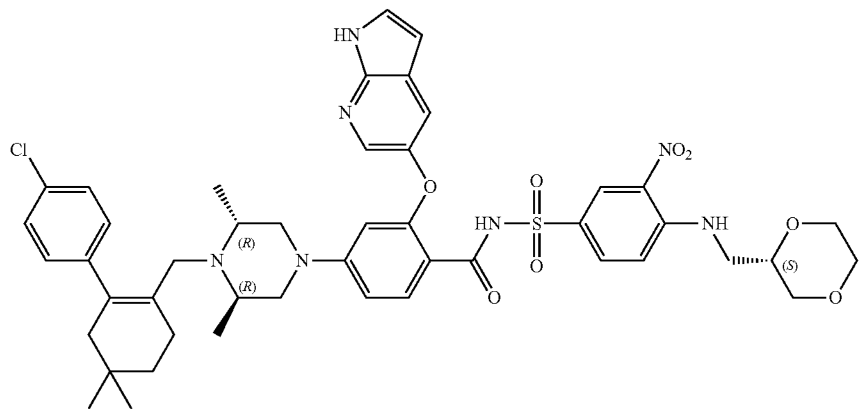

The synthesis of Example 59 was carried out referring to the synthetic procedure of Example 1, wherein in step 2, (R)-2-methylpiperazine was replaced by (2R,6R)-2,6-dimethylpiperazine to give the target compound N-((4-((((S)-1,4-dioxan-2-yl)methyl)amino)-3-nitrophenyl)sulfonyl)-2-((1H-pyrrolo [2,3-b]pyridin-5-yl)oxy)-4-((3R,5R)-4-((4'-chloro-5,5-dimethyl-3,4,5,6-tetrahydro-[1,1'-biphenyl]-2-yl)methyl)-3,5-dimethylpiperazin-1-yl)benzamide 59.

MS m/z(ESI): 898 & 890 [M+1];

$^1$H NMR (400 MHz, $CDCl_3$) δ 9.16 (s, 1H), 8.86 (d, J=2.2 Hz, 1H), 8.61 (s, 1H), 8.22-8.13 (m, 2H), 7.91 (d, J=9.1 Hz, 1H), 7.67-7.60 (m, 1H), 7.44 (s, 1H), 7.23 (d, J=8.3 Hz, 2H), 6.93 (d, J=8.3 Hz, 2H), 6.88 (d, J=9.2 Hz, 1H), 6.60-6.48 (m, 2H), 5.94-5.90 (m, 1H), 3.97-3.85 (m, 2H), 3.85-3.74 (m, 2H), 3.67-3.60 (m, 2H), 3.55-3.29 (m, 3H), 3.13-3.02 (m, 2H), 2.79-2.70 (m, 2H), 2.69-2.59 (m, 2H), 2.24-2.15-(m, 2H), 2.12-2.05 (m, 4H), 2.05-1.86 (m, 2H), 0.93-0.91 (m, 6H), 0.69 (s, 3H), 0.67 (s, 3H).

Biological Tests

Test for Inhibition of BCL-2 Biological Activity

Fluorescence polarization assay was used to evaluate the effect of the compounds of the present invention on the biological activity of BCL-2.

The experimental method was summarized as follows:

The effects of the compounds on the biological activity of BCL-2 were evaluated by determining the effects of the compounds on the binding activity of BCL-2 to leukemia pro-apoptotic protein (BIM) using an affinity assay method based on the principle of fluorescence polarization. The reaction buffer comprises the following components: PBS (pH 7.4, 3 mM $Na_2HPO_4$, 155 mM NaCl, 1 mM $KH_2PO_4$), 1 mM DTT; human recombinant Bcl-2 protein (Item No. 10195-H08E) (purchased from Beijing Yiqiao Shenzhou Biotechnology Co., Ltd.) was diluted to 5 nM with the reaction buffer; FITC-labeled BIM polypeptide (purchased from Nanjing GenScript Biotechnology Co., Ltd.) was diluted to 5 nM with the reaction buffer.

The compounds were dissolved in 100% DMSO and diluted to 0.1, 1, 10 μM, followed by 4-fold serial dilutions with DMSO to a minimum concentration of 0.0061, 0.061, 0.61 nM, each concentration point was further diluted 50-fold with the reaction buffer.

3 μL of solution containing the compound and 12 μL of solution containing BCL-2 were added to the black 384-well assay plate, mixed well, and incubated at room temperature for 15 minutes. Subsequently, 15 μL of FITC-BIM solution was added, and the reaction mixture was incubated at room temperature for 30 minutes in dark place, and then the fluorescence polarization was detected immediately on an Envision multi-mode reader (Perkin Elmer), with 480 nm as the excitation wavelength and 535 nm as the emission wavelength. In this experiment, the group without BCL-2 protein was used as a negative control (100% inhibition), and the group with BCL-2 protein but without the compound was used as a positive control (0% inhibition). The inhibition percentage of the compound to the affinity of BCL-2 can be calculated using the following equation:

The $IC_{50}$ of the compound was calculated from 8 concentration points using XLfit (ID Business Solutions Ltd., UK) software by the following equation:

$$Y=\text{Bottom}+(\text{Top}-\text{Bottom})/(1+10\hat{}((\log IC_{50}-X)*\text{slope factor}))$$

where Y is the inhibition percentage, X is the logarithm of the concentration of the compound to be tested, Bottom is the maximum inhibition percentage, Top is the minimum inhibition percentage, and slope factor is the slope coefficient of the curve.

Test for Inhibition of BCL-XL Biological Activity

Fluorescence polarization assay was used to evaluate the effect of the compounds of the present invention on the biological activity of BCL-XL.

The experimental method was summarized as follows:

The effects of the compounds on the biological activity of BCL-XL were evaluated by detecting the effects of the compounds on the binding activity of BCL-XL to BIM using an affinity assay method based on the principle of fluorescence polarization. The reaction buffer contains the following components: PBS (pH 7.4, 3 mM $Na_2HPO_4$, 155 mM NaCl, 1 mM $KH_2PO_4$), 1 mM DTT; human recombinant Bcl-XL protein (Item No. 10455-H08E) (purchased from Beijing Yiqiao Shenzhou Biotechnology Co., Ltd.) was diluted to 10 nM with reaction buffer; FITC-labeled BIM polypeptide (purchased from Nanjing GenScript Biotechnology Co., Ltd) was diluted to 10 nM with reaction buffer.

The compounds were dissolved in 100% DMSO and diluted to 1 μM, followed by 4-fold serial dilutions in DMSO to a minimum concentration of 0.061 nM, each concentration point was further diluted 50-fold with reaction buffer.

3 μL of solution containing the compound and 12 μL of solution containing BCL-XL were added to the black 384-well assay plate, mixed well, and incubated at room temperature for 15 minutes. Subsequently, 15 μL of FITC-BIM solution was added, and the reaction mixture was incubated at room temperature for 30 minutes in the dark place, and then the fluorescence polarization was detected immediately on an Envision multi-plate reader (Perkin Elmer), with 480 nm as the excitation wavelength and 535 nm as the emission wavelength. In this experiment, the group without BCL-XL protein was used as a negative control (100% inhibition), and the group with BCL-XL protein but without the compound was added as a positive control (0% inhibition). The inhibition percentage of the compound to the affinity of BCL-XL can be calculated using the following equation:

The $IC_{50}$ of the compound was calculated from 8 concentration points using XLfit (ID Business Solutions Ltd., UK) software by the following equation:

$$Y=Bottom+(Top-Bottom)/(1+10^{\wedge}((\log IC_{50}-X)*slope\ factor))$$

where Y is the inhibition percentage, X is the logarithm of the concentration of the compound to be tested, Bottom is the maximum inhibition percentage, Top is the minimum inhibition percentage, and slope factor is the slope coefficient of the curve.

Determination of the Half Effective Inhibitory Concentration $IC_{50}$ of RS4:11 Cells (Acute Lymphoblastic Leukemia Cells)

The effects of the compounds of the present invention on the proliferation of RS4;11 cells were evaluated using a luminescence cell viability assay.

The experimental method was summarized as follows:

A CellTiter-Glo (CTG) Assay Kit is used to detect ATP, a key indicator of the metabolism of living cells, through a unique, highly sensitive and stable luciferase. The luminescent signal generated in the assay is proportional to the number of the viable cells in the medium, therefore the cell proliferation of RS4;11 can be determined.

CellTiter-Glo reagent (Promega, G7572) is composed of CellTiter-Glo lyophilized powder and CellTiter-Glo buffer, and the lyophilized powder can be dissolved in the buffer for use.

RS4;11 cells (ATCC, CRL-1873) were cultured in RPM11640 complete medium (Thermofisher, 72400-047) containing 10% FBS (GBICO, 10099-141) and 100 units/ml penicillin-streptomycin solution (Thermofisher, 15140122)), when the cells covered 80-90% in the culture vessel, they were digested and dispersed with 0.25% trypsin (containing EDTA) (Thermofisher, 25200056) and then planted in a white 384-well plate (Thermofisher, 164610), and then the 384-well plate was incubated overnight in a 37° C., 5% $CO_2$ incubator. Compounds were dissolved in 100% DMSO and diluted to 5 mM, followed by 4-fold serial dilutions with DMSO to a minimum concentration of 0.061 μM, and each concentration point was further diluted 50-fold with FBS-free RPM11640 medium. If the $IC_{50}$ of the compound is very low, the initial concentration of the compound can be reduced. After overnight, 3 μL of the compound diluted in the medium was added to each well, and the mixture was gently centrifuged to mix. The group without cells was used as a negative control (100% inhibition), and the group with 0.2% DMSO was used as a positive control (0% inhibition). The 384-well plate was placed in a 37° C., 5% $CO_2$ incubator for further cultivation. After 48 hours, the plate was taken out and equilibrated to room temperature. 15 μl of CTG reagent was added to each well, the plate was shaken gently for 3 minutes to make sure that the cell lysis was carried out thoroughly, then the plate was kept for 10 minutes to stabilize the luminescence signal, then the luminescence signal was read by EnVision (Perkin Elmer).

The inhibition percentage of the compounds to RS4;11 cell proliferation can be calculated using the following equation:

$$Inhibition\ Percentage=100-100*(signal\ compound-signal\ negative\ control)/(signal\ positive\ control-signal\ negative\ control)$$

The $IC_{50}$ of the compound was calculated from 8 concentration points using XLfit (ID Business Solutions Ltd., UK) software by the following equation:

$$Y=Bottom+(Top-Bottom)/(1+10^{\wedge}((Log\ IC_{50}-X)*slope\ factor))$$

wherein, Y is the inhibition percentage, Bottom is the bottom plateau of the curve (the bottom plateau value of the S-shaped curve), Top is the top plateau of the curve (the top plateau value of the S-shaped curve), and X is the logarithm of the concentration of the compound to be tested.

The results of the above-mentioned in vitro BCL-2 and BCL-XL protein activity assay are shown in Table 1 below, The results of the cell experiments are shown in Table 2.

TABLE 1

Detection results of BCL-2 and BCL-XL protein activity

| Number of the compound | FP BCL-2 $IC_{50}$ (nM) | FP BCL-XL $IC_{50}$ (nM) |
|---|---|---|
| 1 | 2.05 | >1000 |
| 2 | 2.56 | >1000 |
| 3 | 3.06 | >1000 |
| 4 | 2.29 | 742.8 |
| 5 | 1.54 | >1000 |
| 6 | 0.90 | >1000 |
| 7 | >100 | >1000 |
| 8 | 4.55 | >1000 |
| 9 | 5.03 | >1000 |

TABLE 1-continued

| Detection results of BCL-2 and BCL-XL protein activity | | |
|---|---|---|
| Number of the compound | FP BCL-2 $IC_{50}$ (nM) | FP BCL-XL $IC_{50}$ (nM) |
| 10 | 8.21 | >1000 |
| 11 | 12.8 | >1000 |
| 12 | 4.89 | >1000 |
| 13 | >100 | >1000 |
| 14 | 2.35 | >1000 |
| 15 | 5.99 | >1000 |
| 16 | 3.41 | >1000 |
| 17 | 1.46 | 952.96 |
| 18 | 1.32 | >1000 |
| 19 | 2.13 | >1000 |
| 20 | 2.57 | >1000 |
| 21 | 1.97 | >1000 |
| 22 | 1.49 | >1000 |
| 23 | 9.37 | >1000 |
| 24 | 6.3 | >1000 |
| 25 | 2.71 | >1000 |
| 26 | 1.63 | >1000 |
| 27 | 5.12 | >1000 |
| 28 | 1.37 | >1000 |
| 29 | 1.6 | >1000 |
| 30 | 0.84 | 830.51 |
| 31 | 3.57 | >1000 |
| 32 | 1.8 | >1000 |
| 33 | 3.16 | >1000 |
| 34 | 3.33 | >1000 |
| 35 | 2.96 | >1000 |
| 36 | 4.78 | >1000 |
| 37 | 3.15 | >1000 |
| 38 | 5.24 | >1000 |
| 39 | 2.68 | >1000 |
| 40 | 1.77 | >1000 |
| 41 | 1.28 | >1000 |
| 42 | 1.53 | >1000 |
| 43 | 6.33 | >1000 |
| 44 | 4.98 | >1000 |
| 45 | 4.22 | >1000 |
| 46 | 1.09 | >1000 |
| 47 | >100 | >1000 |
| 48 | 63.79 | >1000 |
| 49 | >100 | >1000 |
| 50 | >100 | >1000 |
| 51 | >100 | >1000 |
| 52 | 1.9 | >1000 |
| 53 | >100 | >1000 |
| 54 | 11 | >1000 |
| 55 | 2.3 | >1000 |
| 56 | 82 | >1000 |
| 57 | >500 | >1000 |
| 58 | 29.86 | >1000 |
| 59 | 73.22 | >1000. |

TABLE 2

| RS4; 11 cellular assay results | |
|---|---|
| Number of the compounds | RS4; 11 $IC_{50}$ (nM) |
| 1 | 4.73 |
| 2 | 11.07 |
| 3 | 6.4 |
| 4 | 5.8 |
| 5 | 2.75 |
| 6 | 2.37 |
| 7 | >500 |
| 8 | 6.2 |
| 9 | 26 |
| 10 | 68 |
| 11 | 42 |
| 12 | 16 |
| 13 | >500 |
| 14 | 3.8 |
| 15 | 19 |
| 16 | 8.8 |
| 17 | 3.1 |
| 18 | 2.4 |
| 19 | 4.25 |
| 20 | 8.8 |
| 21 | 8.8 |
| 22 | 4.1 |
| 23 | 51 |
| 24 | 24 |
| 25 | 32 |
| 26 | 14 |
| 27 | 16 |
| 28 | 6.55 |
| 29 | 4.2 |
| 30 | 2.3 |
| 31 | 8.1 |
| 32 | 6.6 |
| 33 | 16 |
| 34 | 6.6 |
| 35 | 17 |
| 36 | 21 |
| 37 | 22 |
| 38 | 32 |
| 39 | 14.5 |
| 40 | 15 |
| 41 | 8 |
| 42 | 10 |
| 43 | 161 |
| 44 | 54 |
| 45 | 52 |
| 46 | 18 |
| 47 | 486 |
| 48 | 229 |
| 49 | >500 |
| 50 | >500 |
| 51 | >500 |
| 52 | 5.1 |
| 53 | >500 |
| 54 | 25 |
| 55 | 5.7 |
| 56 | 224 |
| 57 | >1000 |
| 58 | 141.94 |
| 59 | 193 |
| Venetoclax | 5.5 |

It can be seen from the above test results that the compounds of the examples of the present invention can effectively and selectively inhibit the activity of BCL-2, but have weak inhibition on BCL-XL. These compounds can be used to treat a variety of cancers caused by abnormal overexpression of BCL-2 family proteins: hematological malignancies (especially acute lymphoblastic leukemia), lung cancer, breast cancer, ovarian cancer, rectal cancer, prostate cancer, pancreatic cancer, brain glioma. Toxic side effects caused by BCL-XL inhibition could be avoided, such as thrombocytopenia. Some compounds can also effectively inhibit RS4; 11 acute lymphocyte proliferation and have strong inhibitory effects on malignant blood diseases such as acute lymphoblastic leukemia.

It will be apparent to those skilled in the art that the present disclosure is not limited to the above-described illustrative embodiments, and that it may be realized in other specific forms without departing from the essential characteristics of the present disclosure. Therefore, it is intended that these embodiments be considered in all respects to be illustrative and non-restrictive, reference should be made to the appended claims, rather than the above-described embodiments, and all changes within the meaning and scope of equivalence of the claims are included in the protection scope of the present application.

The invention claimed is:

1. A compound of formula (I), or an isomer, prodrug, solvate, stable isotopic derivative or pharmaceutically acceptable salt thereof:

(I)

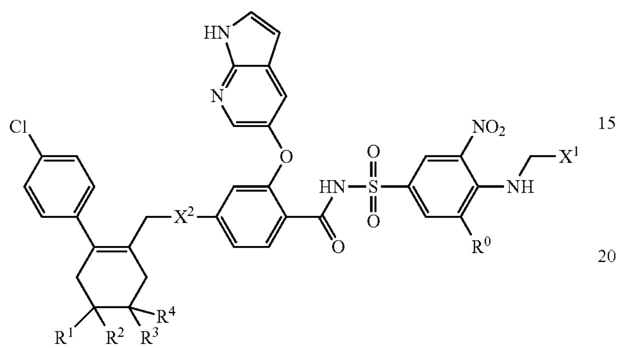

wherein:

$X^1$ is selected from 1,4-dioxanyl, tetrahydropyranyl, N-oxetanylpiperidinyl, and N-oxetanylmorpholinyl;

$X^2$ is selected from

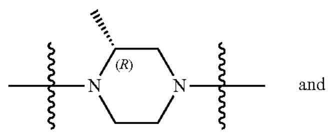

and

-continued

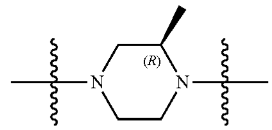

;

$R^0$ is selected from hydrogen and fluorine; and $R^1$, $R^2$, $R^3$, $R^4$ are each independently selected from hydrogen and methyl; provided that $R^1$, $R^2$, $R^3$, $R^4$ are not all hydrogen; wherein $R^1$ and $R^2$ or $R^3$ and $R^4$ together with the carbon atoms to which they are attached may form a cyclopropyl group.

2. The compound of formula (I) according to claim 1, or an isomer, prodrug, solvate, stable isotopic derivative or pharmaceutically acceptable salt thereof, wherein:

$X^1$ is selected from (S)-1,4-dioxan-2-yl, (R)-1,4-dioxan-2-yl, tetrahydropyran-4-yl, 1-(oxetan-3-yl)piperidin-4-yl, and (S)-4-(oxetan-3-yl)morpholin-2-yl; and $R^1$, $R^2$, $R^3$, $R^4$ are each independently selected from hydrogen and methyl; provided that $R^1$, $R^2$, $R^3$, $R^4$ are not all hydrogen; wherein $R^3$ and $R^4$ together with the carbon atoms to which they are attached may form a cyclopropyl group.

3. The compound of formula (I) according to claim 1, or an isomer, prodrug, solvate, stable isotopic derivative or pharmaceutically acceptable salt thereof, which is selected from the group consisting of:

1

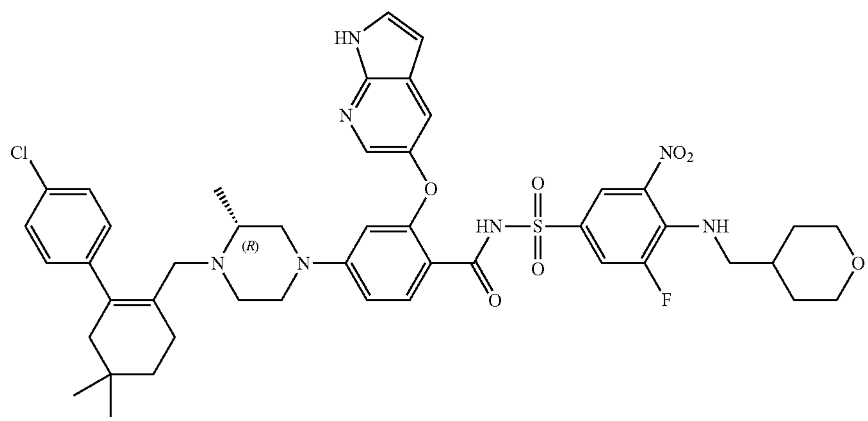

-continued
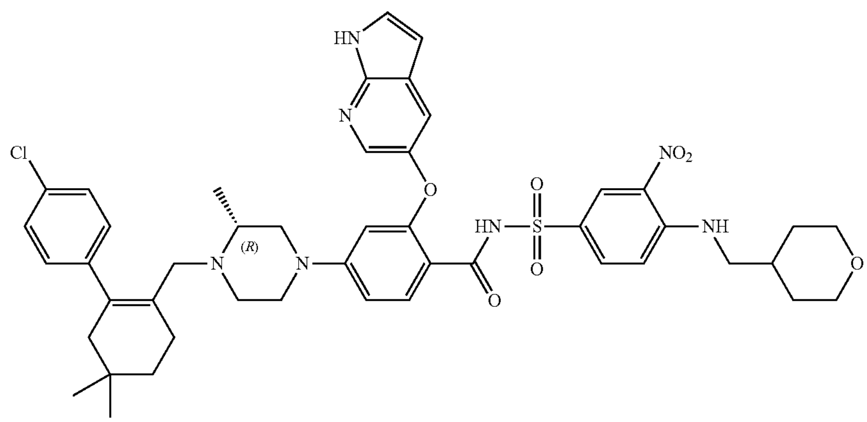
2
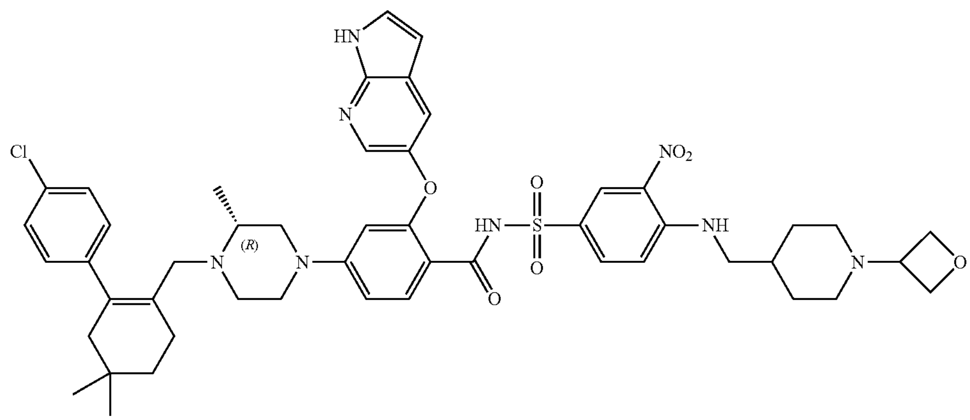
3
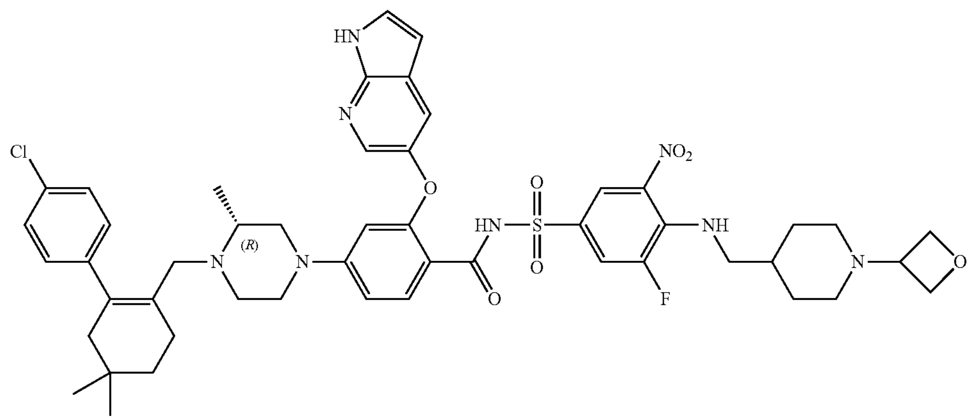
4

-continued
5
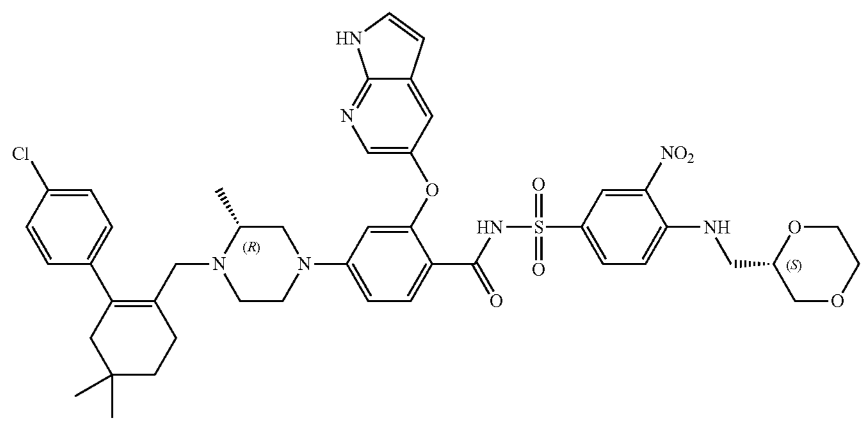
6
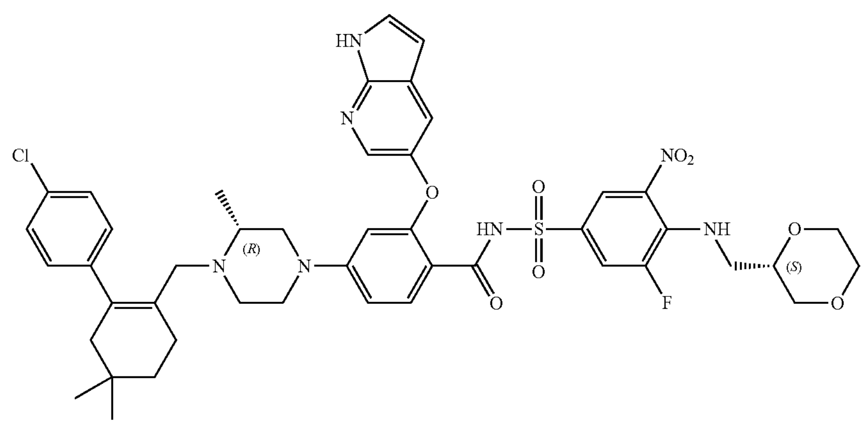
8
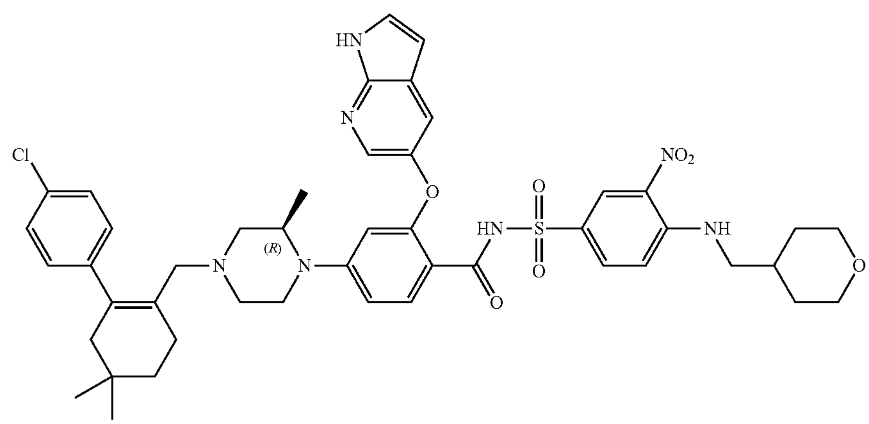

-continued
9
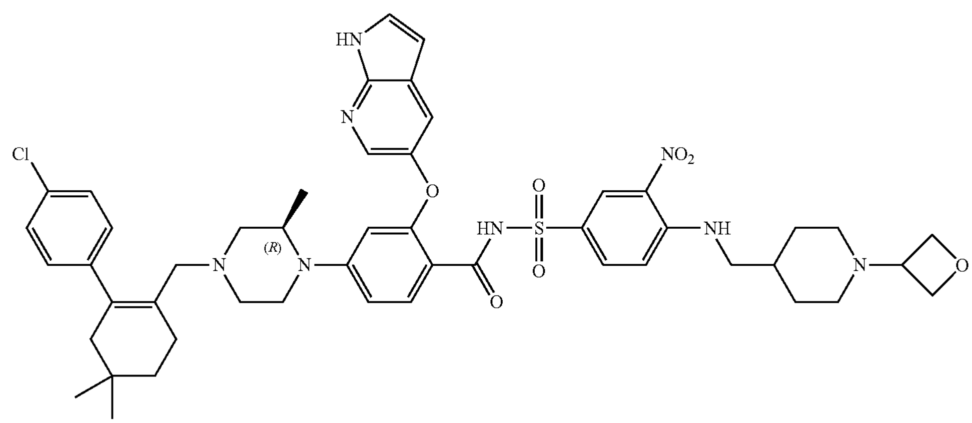
10
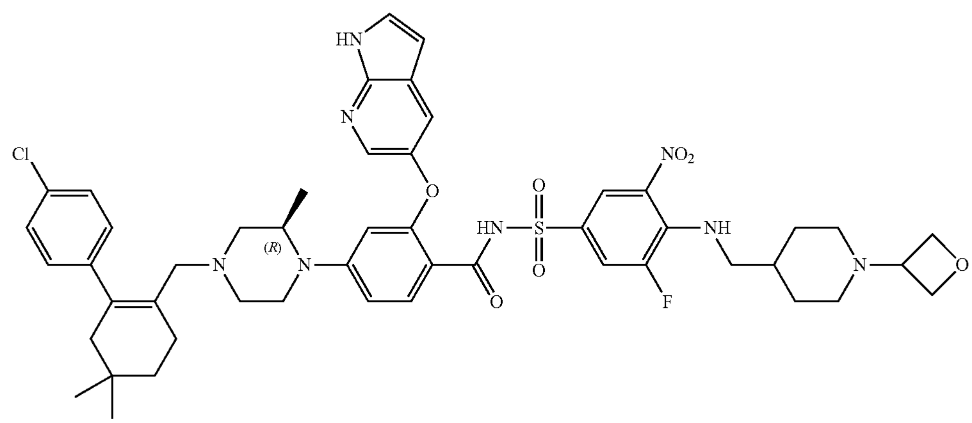
11
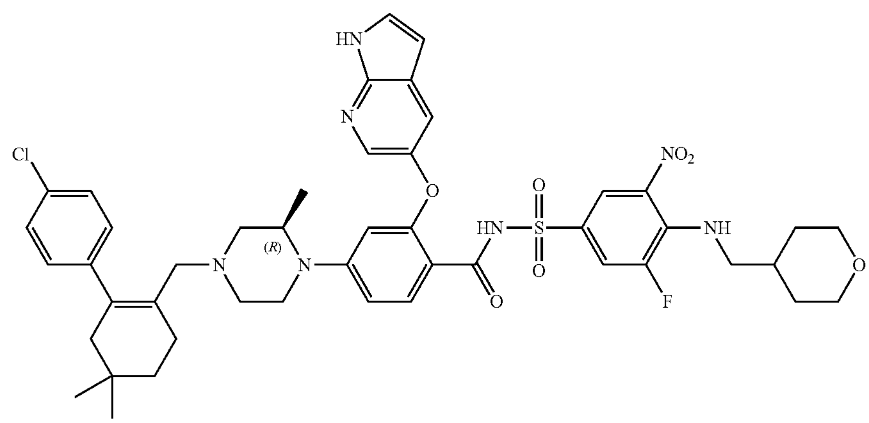

-continued
12
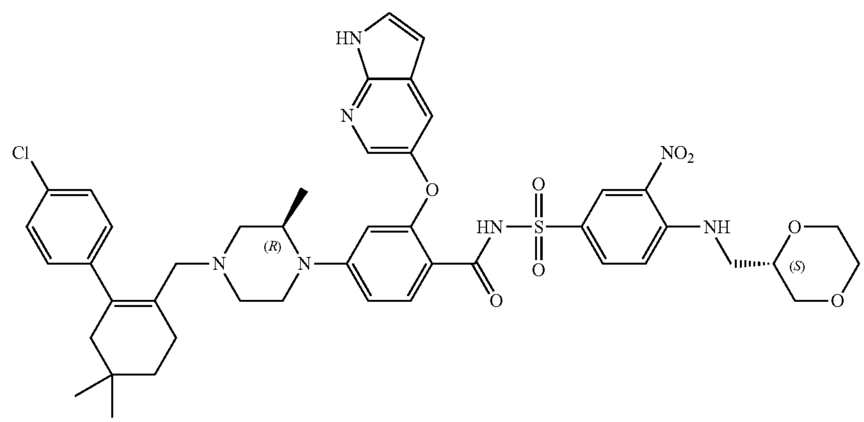
14
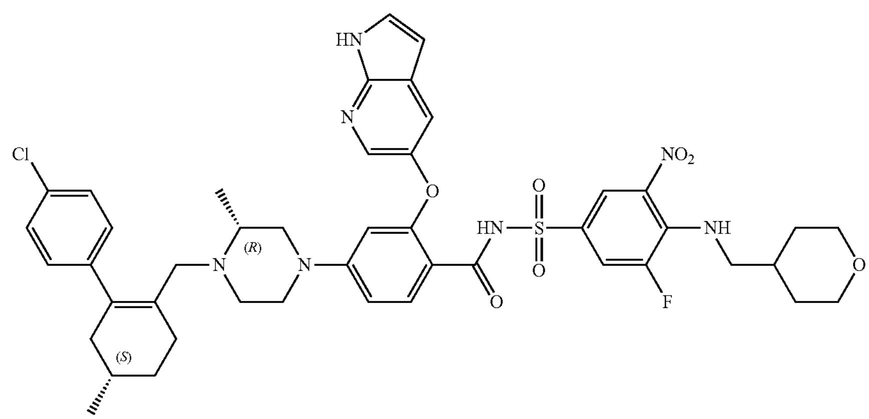
15
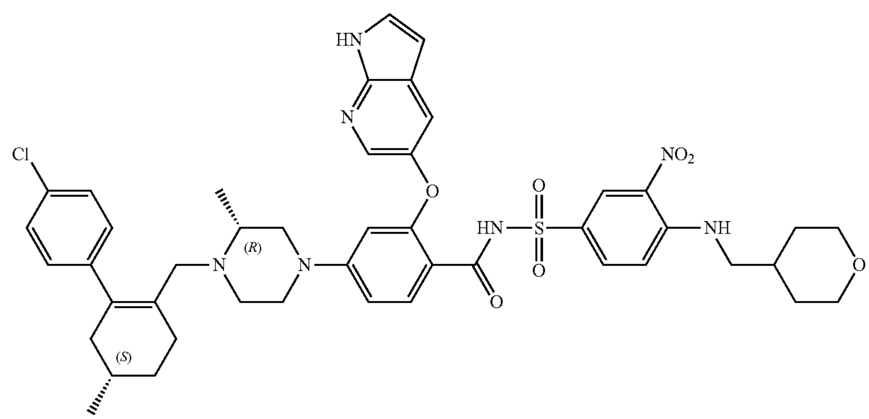

-continued
16
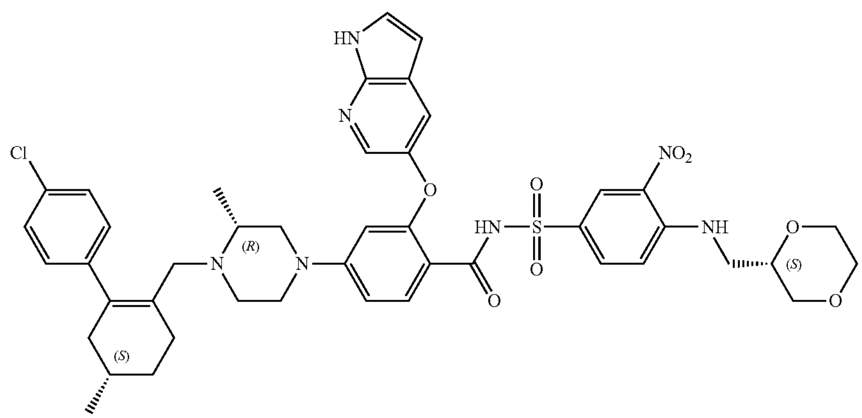
17
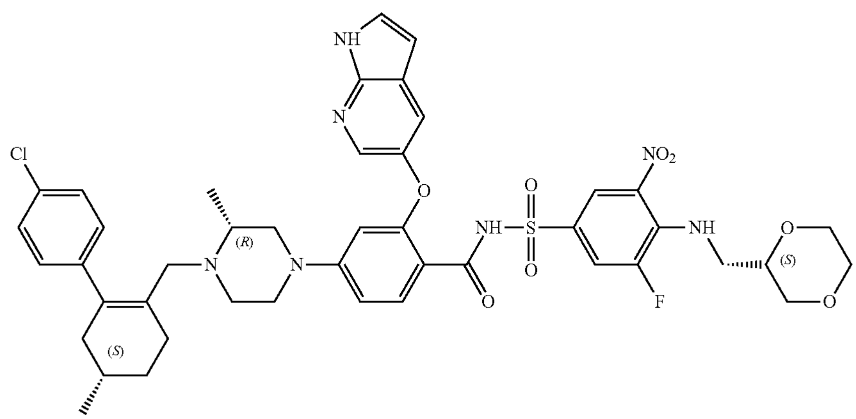
18
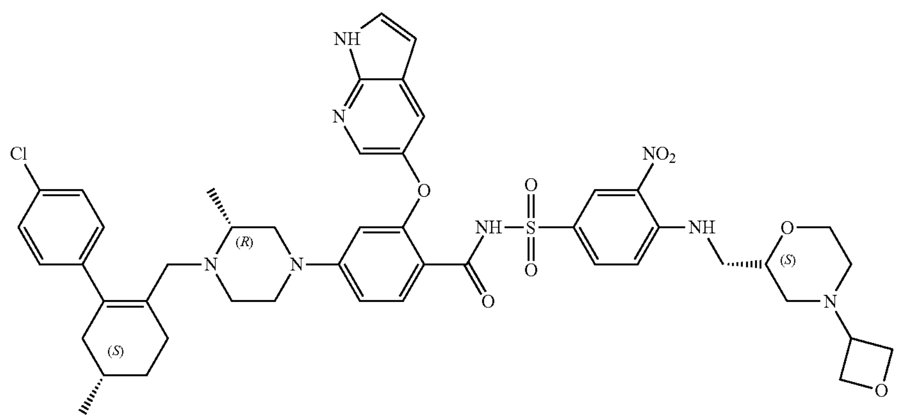
19
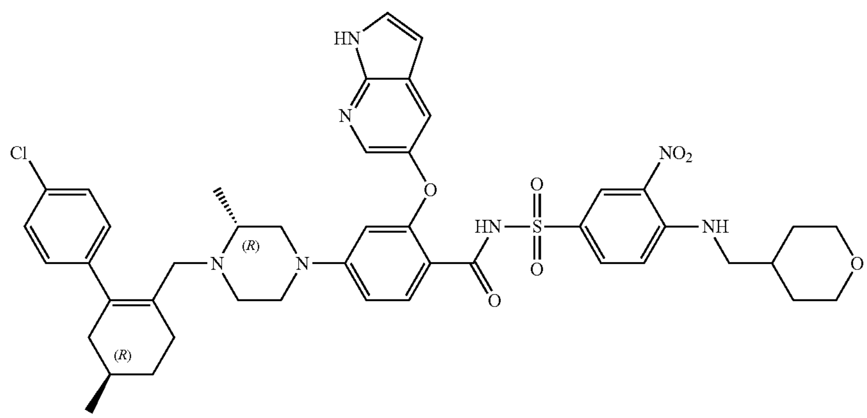

-continued
20
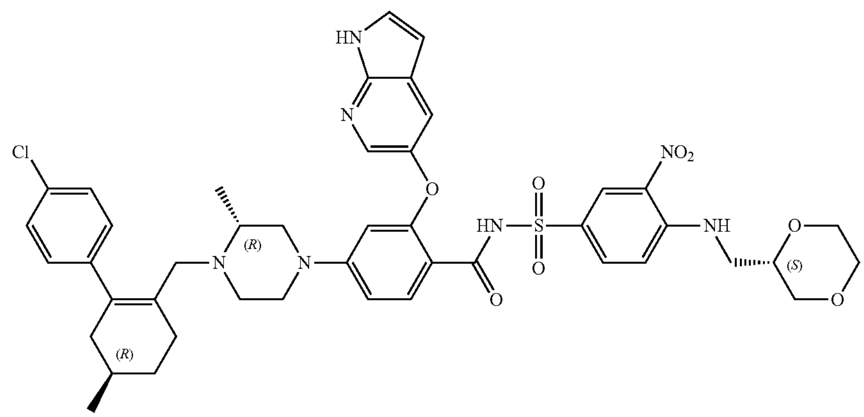
21
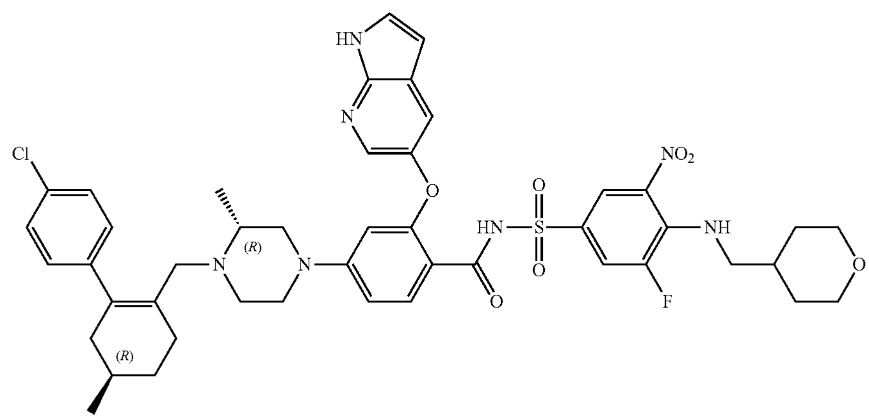
22
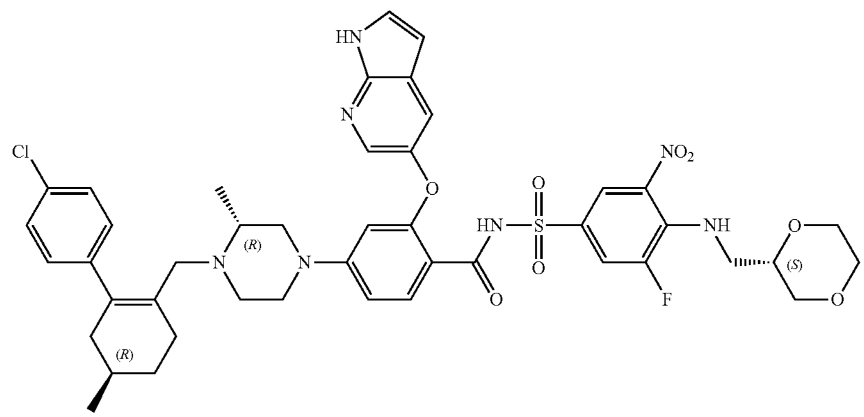

-continued
23
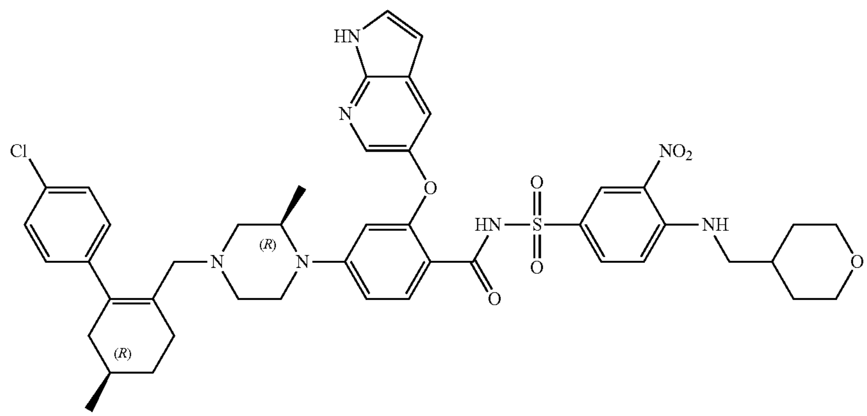
24
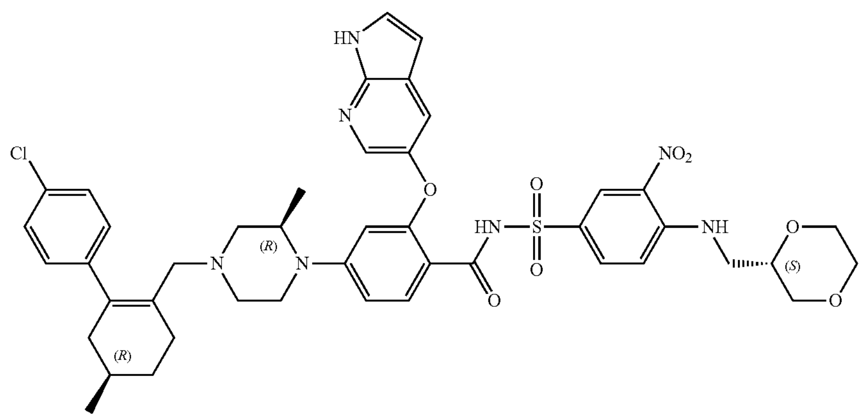
25
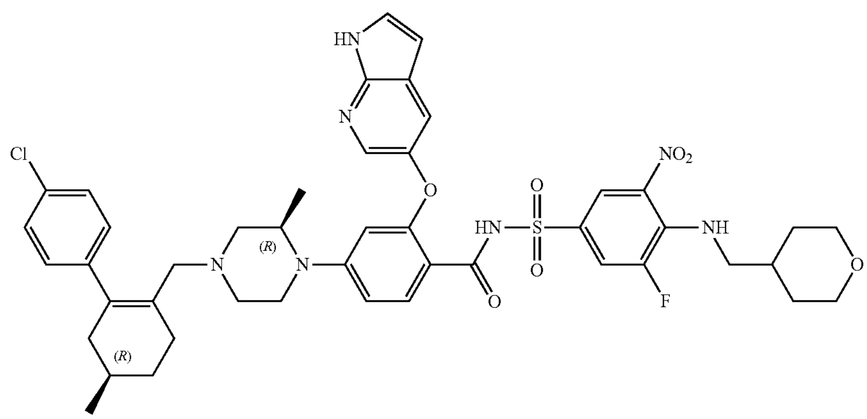
26
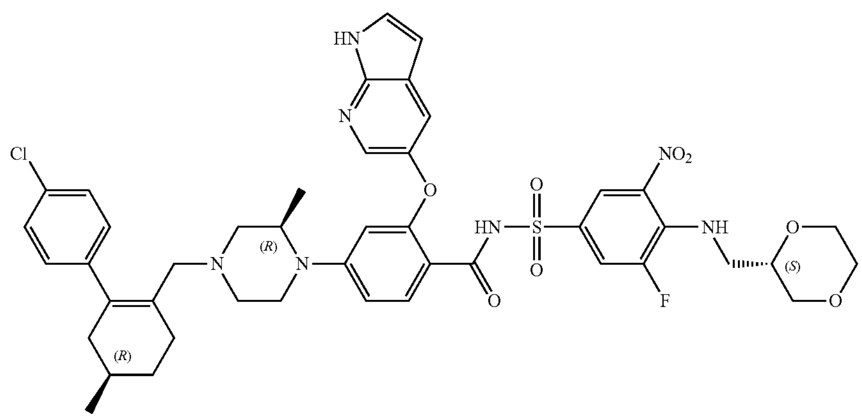

-continued
27
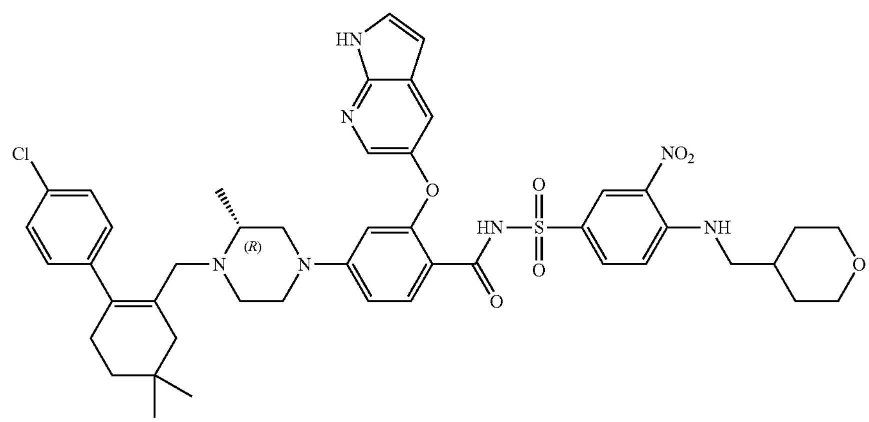
28
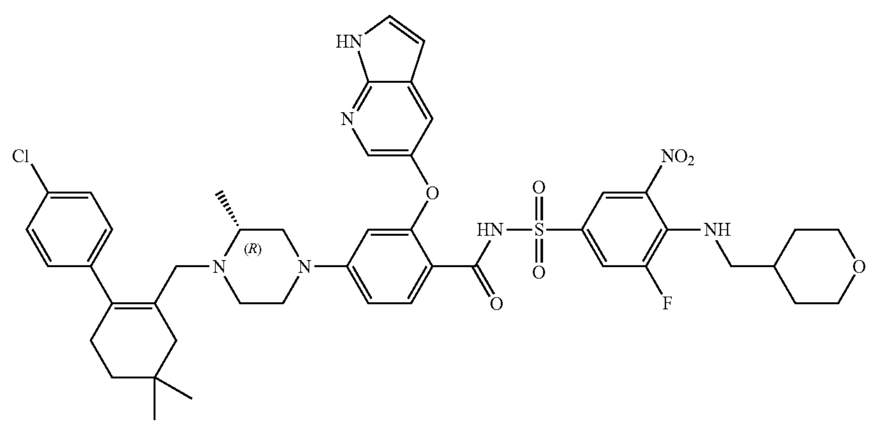
29
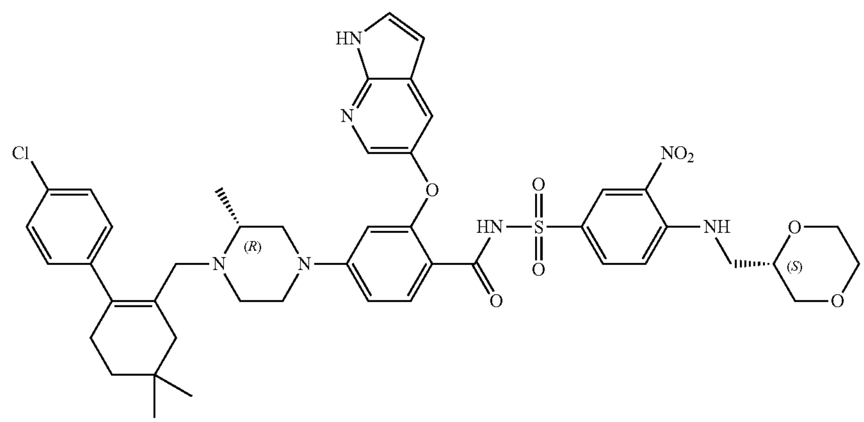

-continued
30
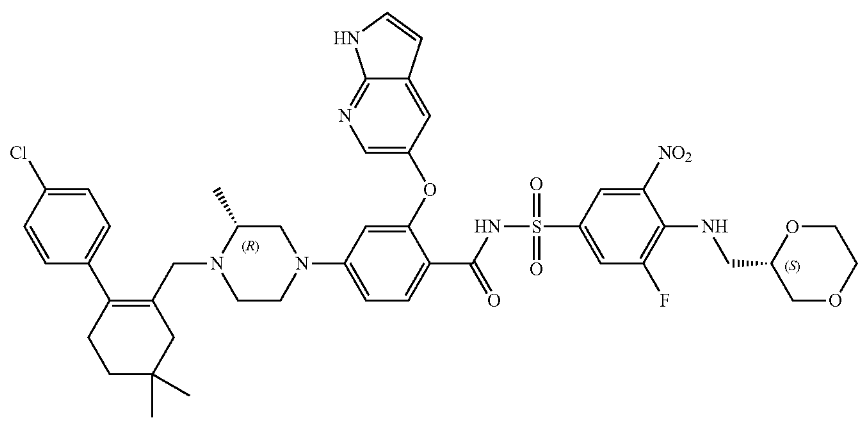
31
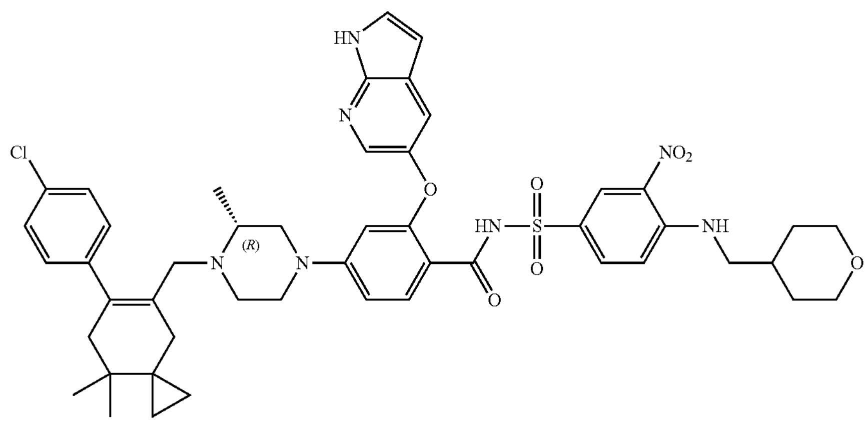
32
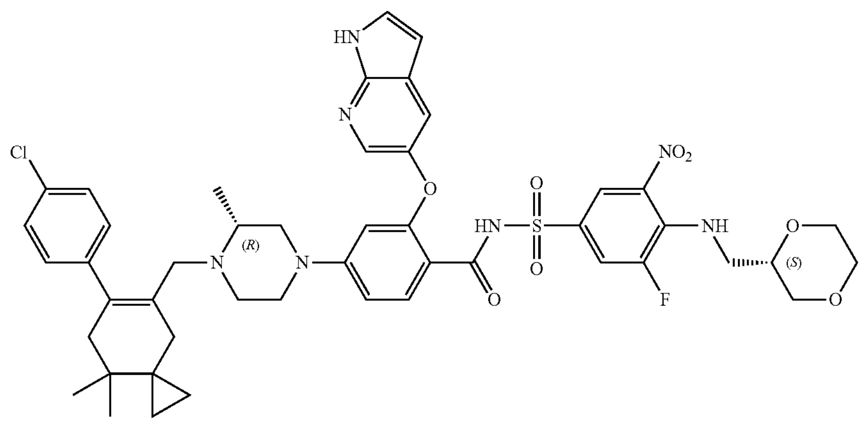

-continued
33
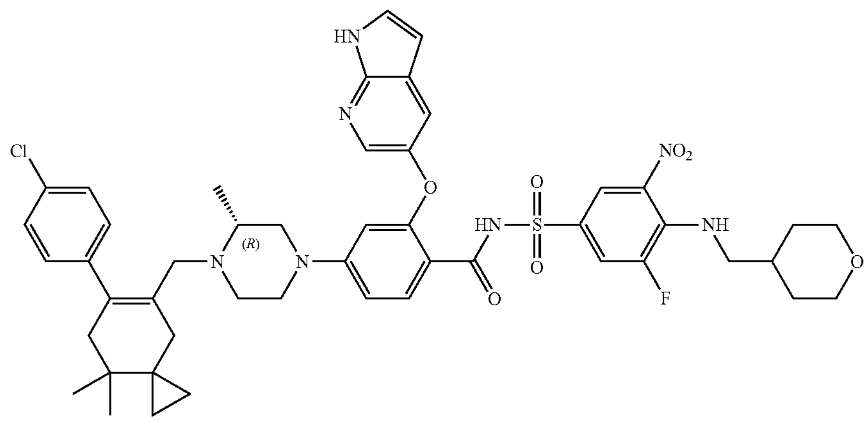
34
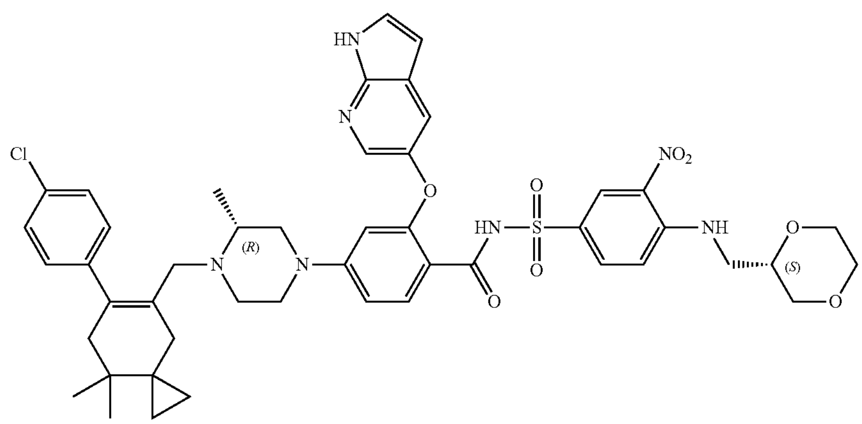
35
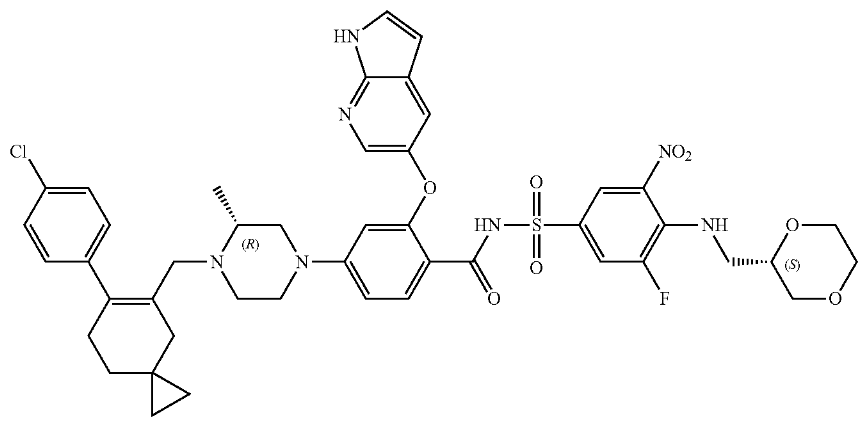

-continued
36
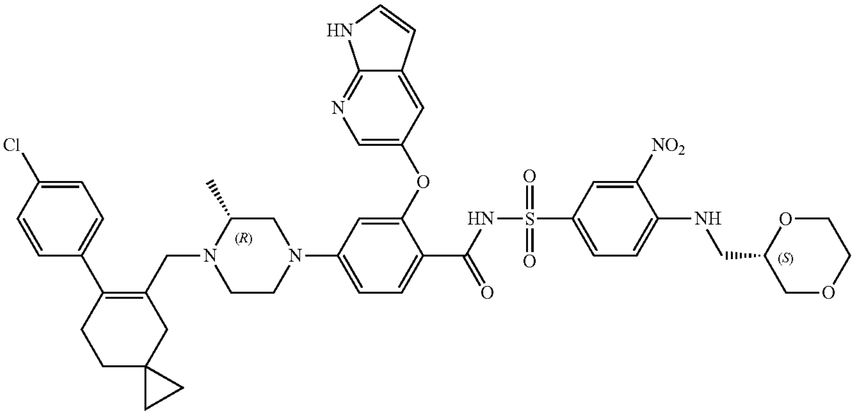
37
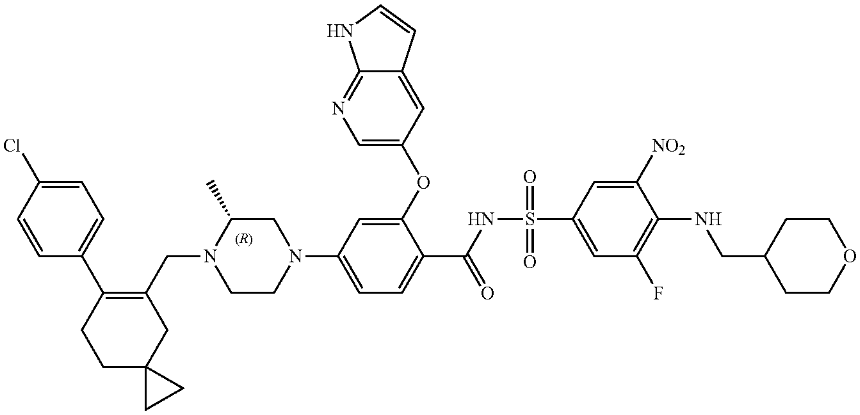
38
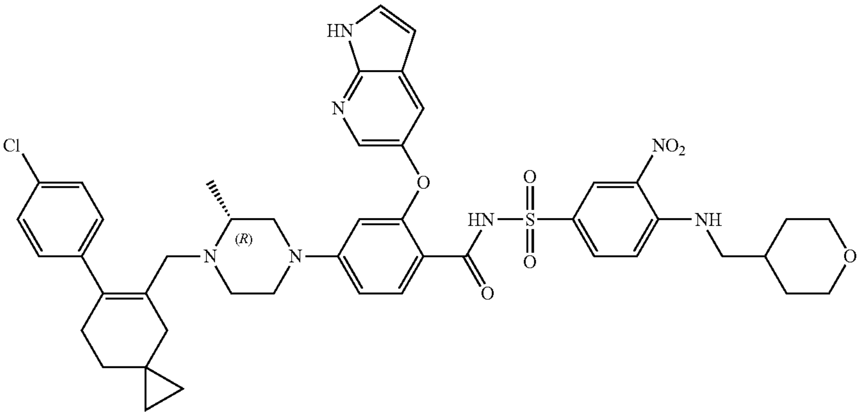

-continued
39
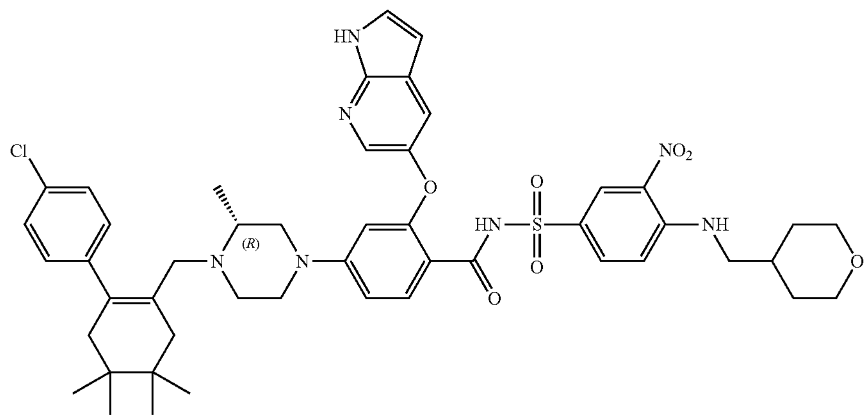
40
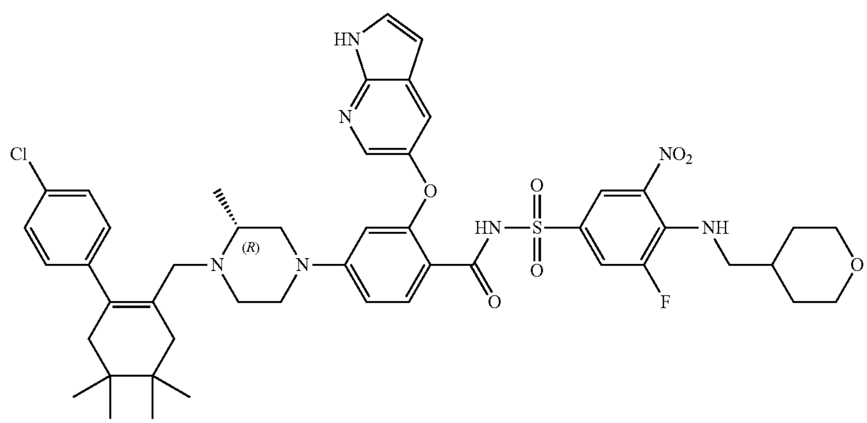
41
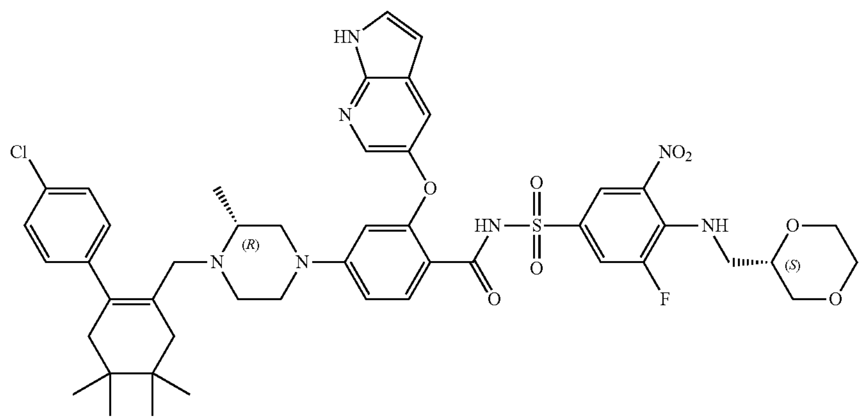

-continued
42
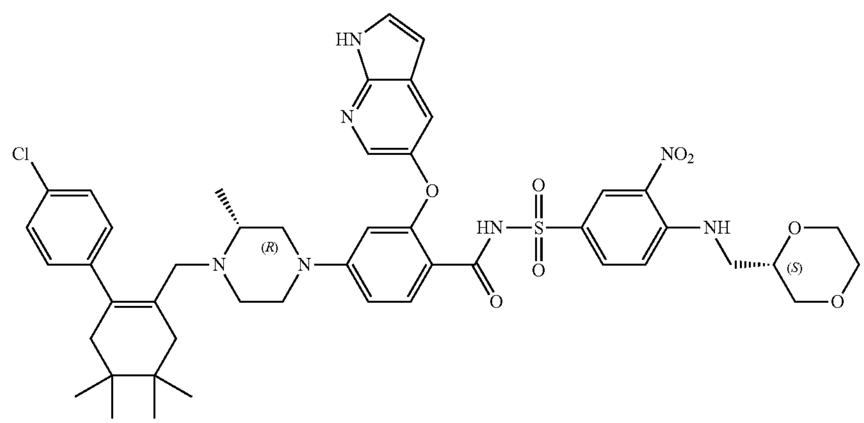
43
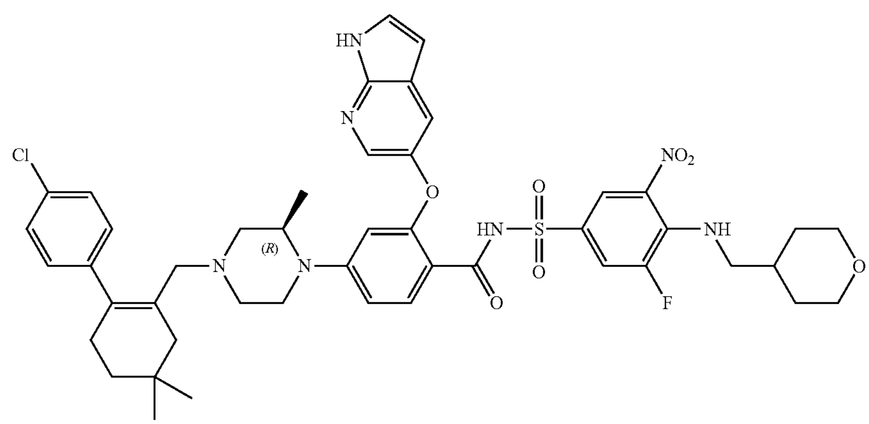
44
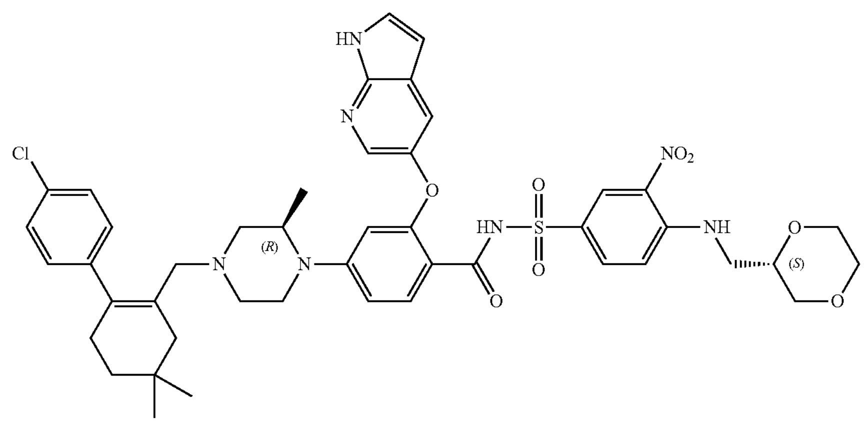

-continued
45
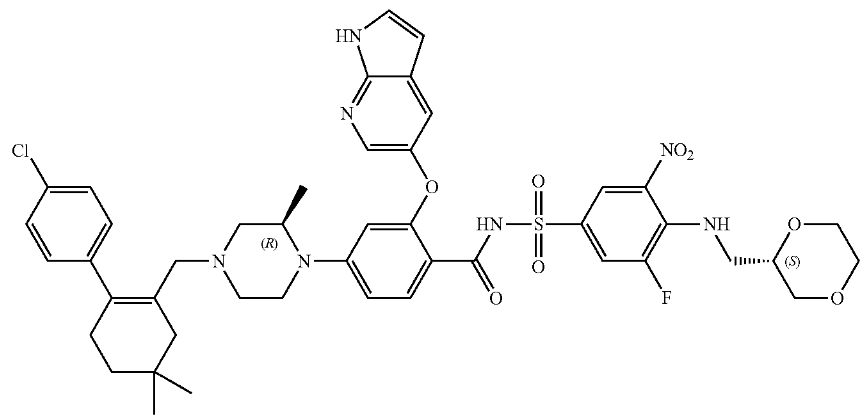
46
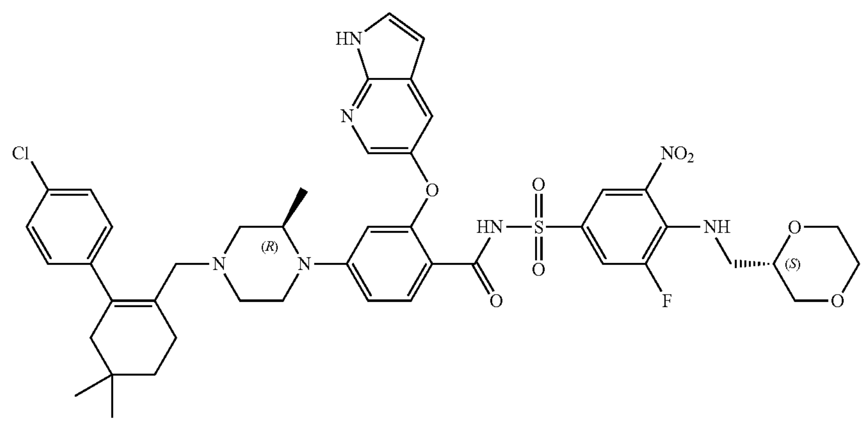
52
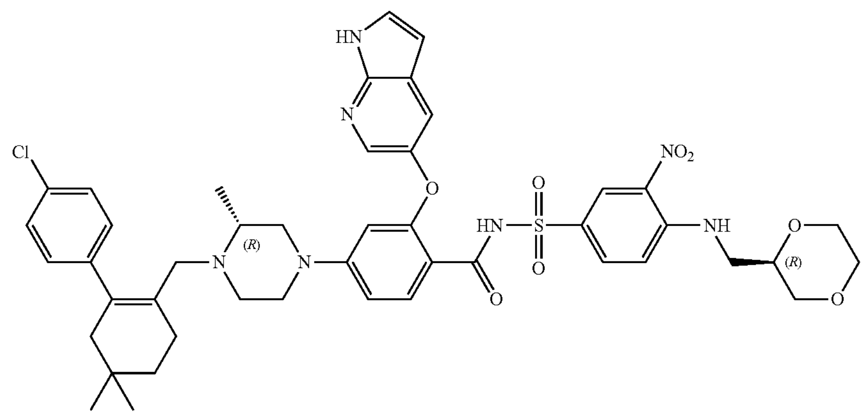

-continued

54

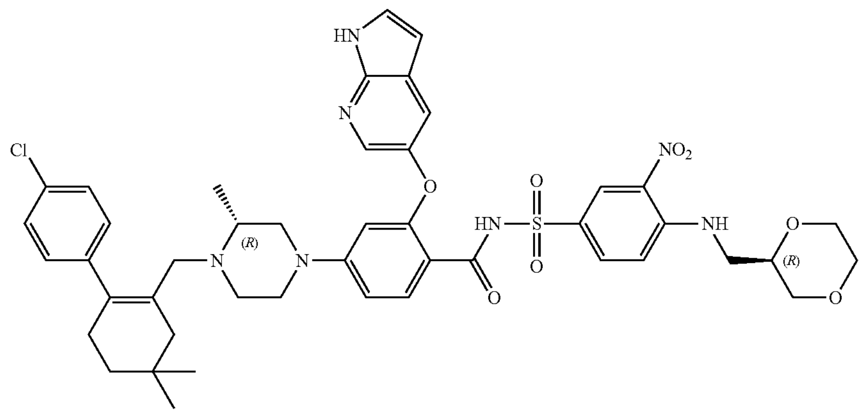

55

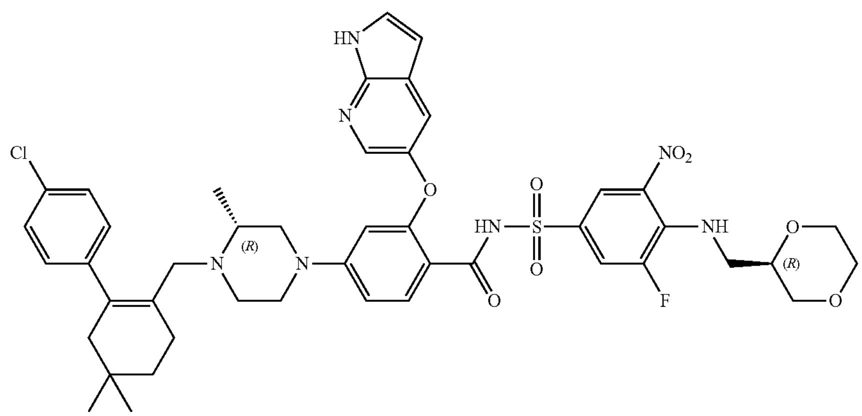

4. A method of inhibiting B-cell lymphoma-2 (BCL-2), comprising administering to a subject in need thereof an effective amount of a compound according to claim 1, or an isomer, prodrug, solvate, stable isotope derivative or pharmaceutically acceptable salt thereof.

5. A method of treating tumors comprising acute lymphoblastic leukemia, lung cancer, breast cancer, ovarian cancer, rectal cancer, prostate cancer, pancreatic cancer, glioma; comprising administering to a subject in need thereof a therapeutically effective amount of a compound according to claim 1, or an isomer, prodrug, solvate, stable isotope derivative or pharmaceutically acceptable salt thereof.

6. A pharmaceutical composition comprising a compound according to claim 1, or an isomer, prodrug, solvate, stable isotopic derivative or pharmaceutically acceptable salt thereof, optionally one or more other BCL-2 inhibitors, and one or more pharmaceutically acceptable carriers, diluents and excipients.

* * * * *